United States Patent
Stiles et al.

(10) Patent No.: US 6,403,082 B1
(45) Date of Patent: Jun. 11, 2002

(54) BACTERIOCINS, TRANSPORT AND VECTOR SYSTEM AND METHOD OF USE THEREOF

(76) Inventors: Michael E. Stiles, 11623-33 Avenue, Edmonton, Alberta (CA), T6J 3G9; John C. Vederas, 9247 96 Street, Edmonton, Alberta (CA), T6C 3Y5; Marius J. Van Belkum, De Vennen 12, 7921 HT Zuidwolde (NL); Randy W. Worobo; Rodney J. Worobo, both of Box 247, Consort, Alberta (CA), T0C 1B0; John K. McCormick, 34 Evergreen Drive, Nepean, Ontario (CA), K2H 6C8; G. Gordon Greer, 5316 51 Avenue, Lacombe, Alberta (CA), T4L 1J6; Lynn M. McMullen, 10528 75 Avenue, Edmonton, Alberta (CA), T6E 1J4; Jorgen J. Leisner, 210, Blok 4, Pangsapuri, PKNS, Jalan 7/1 43300 Seri, Kembangan, Selangor D.E. (MY); Alison Poon, 10908 40th Avenue, Edmonton, Alberta (CA), T6J 0P8; Charles M. A. P. Franz, Hofacker Street 50, Karlfruhe 76139 (DE)

( * ) Notice: Subject to any disclaimer, the term of this patent is extended or adjusted under 35 U.S.C. 154(b) by 0 days.

(21) Appl. No.: 08/924,629

(22) Filed: Sep. 5, 1997

Related U.S. Application Data

(60) Provisional application No. 60/026,257, filed on Sep. 5, 1996.

(51) Int. Cl.$^7$ .......................... A01N 63/00; A23L 3/00; C12N 1/21
(52) U.S. Cl. ......................... 424/93.2; 426/9; 426/61; 435/69.1; 435/69.7; 435/69.8; 435/252.3
(58) Field of Search ................. 426/61, 9; 424/93.2, 424/93.4; 514/12; 536/23.7; 435/252.3, 252.1, 69.1, 69.7, 69.8

(56) References Cited

U.S. PATENT DOCUMENTS 5,186,962 A * 2/1993 Hutkins et al. ............... 426/61

OTHER PUBLICATIONS

Siragusa et al, Applied and Environmental Microbiology 59:2326–2328, Jul. 1993.*
McCormick et al, Applied and Environmental Microbiology 62:4095–4099, Nov. 1996.*
Worobo et al, Journal of Bacteriology 177:3143–3149, Jun. 1995.*
Poon, Alison M.S. Thesis, University of Alberta. Dissertation Abstracts Online, vol. 34/04, p. 1590, 1995.*
Chikindas et al (Letters in Applied Microbiology 21:183–189, 1995), 1995.*
Hasting, J.W. et al., "Characterization of Leucocin A–UAL 187 and cloning of the Bacteriocin gene from Leuconostoc gelidum", Dec. 1991, Jln. of Bacteriology, 173(23): 7491–7500.
Greer, G.G., et al., "Freezing effects on quality, bacteriology and retail–case life of pork", 1991, Jln. Of Food Science, 56(4):891–894.
Hastings, J.W., et al., "Antibiosis of Leuconostoc gelidum isolated from meat", 1991, Jln. of Applied Bacteriology, 70:127–134.
Henderson, J.T., et al., "Purification and primary structure of pediocin PA–1 produced by *Pediococcus acidilactici* PAC–1.0", May 1992, Archives of Biochemistry and Biophysics, 295(1):5–12.
Allison, G.E. et al., "Heterologous expression of Lactacin F peptides by *Carnobacterium piscicola* LV17",0 Apr. 1995, Applied and Environmental Microbiology, 61(4):1371–1377.
Gilson, L., et al., "Genetic analysis of an MDR–like export system: the secretion of colicin V", The EMBO Jln., 9(12):3875–3884.
Franz et al., "Production and characterization of enterocin 900, a bacteriocin produced by *Enterococcus faecium* BFE 900 from black olives", Abstract *International Journal of Food Microbiology*, vol. 29, No. 2–3, 1996, pp. 255–270 (Abstract Only).
Abstract, McMullen et al., "*Leuconostoc gelidum* UAL 187 Extends the Storage Life of Inoculated Vacuum Packaged Ground Beef", Dept. of Agricultural, Good and Nutritional Science (1996), University of Alberta, Edmonton Can.

* cited by examiner

*Primary Examiner*—Mary E. Mosher

(57) ABSTRACT

New bacteriocins capable of inhibiting the growth of bacteria are disclosed, along with methods of obtaining secretion of proteins from lactic acid bacteria, and methods for protecting foodstuffs.

3 Claims, 14 Drawing Sheets

SEQUENCE LISTING

<160> NUMBER OF SEQ ID NOS: 80

<210> SEQ ID NO 1
<211> LENGTH: 184
<212> TYPE: DNA
<213> ORGANISM: Divergicin A
<220> FEATURE:
<221> NAME/KEY: RBS
<222> LOCATION: (24)..(28)
<223> OTHER INFORMATION:
<221> NAME/KEY: CDS
<222> LOCATION: (38)..(184)
<223> OTHER INFORMATION:
<221> NAME/KEY: sig_peptide
<222> LOCATION: (38)..(125)
<223> OTHER INFORMATION:
<221> NAME/KEY: primer_bind
<222> LOCATION: (114)..(144)
<223> OTHER INFORMATION:
<221> NAME/KEY: misc_feature
<222> LOCATION: (114)..(119)
<223> OTHER INFORMATION: label= restriction_ site

<400> SEQUENCE: 1

```
atcttggtat cacaaactaa tttggaggtt ggtatat atg aaa aaa caa att tta        55
                                        Met Lys Lys Gln Ile Leu
                                         1               5 aaa ggg ttg gtt ata gtt gtt tgt tta tct g gg gca aca ttt ttc tca       103
Lys Gly Leu Val Ile Val Val Cys Leu Ser G ly Ala Thr Phe Phe Ser
           10              15                   20 aca cca caa caa gct tct gct gta aat tat g gt aat ggt gtt tct tgc       151
Thr Pro Gln Gln Ala Ser Ala Val Asn Tyr G ly Asn Gly Val Ser Cys
        25                  30                  35 agt aaa aca aaa tgt tca gtt aac tgg gga c aa                            184
Ser Lys Thr Lys Cys Ser Val Asn Trp Gly G ln
    40                  45
```

<210> SEQ ID NO 2
<211> LENGTH: 49
<212> TYPE: PRT
<213> ORGANISM: Divergicin A

```
<220> FEATURE:
<221> NAME/KEY: misc_feature
<222> LOCATION: (114)..(119)
<223> OTHER INFORMATION: label= restriction_ site

<400> SEQUENCE: 2

Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala Val Asn Tyr
            20                  25                  30

Gly Asn Gly Val Ser Cys Ser Lys Thr Lys Cys Ser Val Asn Trp Gly
        35                  40                  45

Gln

<210> SEQ ID NO 3
<211> LENGTH: 49
<212> TYPE: PRT
<213> ORGANISM: Leuconostoc lactis

<400> SEQUENCE: 3

Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala Val Asn Tyr
            20                  25                  30

Gly Asn Gly Val Ser Cys Ser Lys Thr Lys Cys Ser Val Asn Trp Gly
        35                  40                  45

Gln

<210> SEQ ID NO 4
<211> LENGTH: 4290
<212> TYPE: DNA
<213> ORGANISM: Leucocin A gene;

<400> SEQUENCE: 4 aattttttgcc catgctgcat gatattttga ctaccaaaaa atatgcgtgt t gcgtacttc     60
aatgttgata atttttttaa agataattcc tctgacaaag ctagttatat t aatttcttt    120
caagagttaa atatttctca actgccttct ttaatttta ctaatggaaa c atggactat    180
aaacgattat caatttatac aattaaaaca ccaataaatg catggattac t gctattaat    240
gacgaattaa tttcaaaaca ttccaagcaa tcatcaacaa attaaaaatg g ttaaggtca    300
aaatgtttca aaaagaata aattatatcg cacaagtaga tgaacgtgat t gtggtgttg    360
ctgcactcgc tatggtttta actcattaca aaacacgcct gtccttagcc a aactacggg    420
acctggccaa aactgacatg gaaggaacga ctgctttagg cattgttaaa g ctgcgaatg    480
cgctagactt tgaaaccatg ccgatccagg ctgatttgag tttattcgat a aaaaggatt    540
taccctatcc ttttatcgcc catgtcatta agacggtaa ataccgcat t attatgtag    600
tttatgggat caaaggtgat cagctattaa tcgctgatcc agataatacc g ttggtaaaa    660
ataaaatgac aaaagcgcat tttaatgagg agtggaccgg tgtgtccatt t ttattgcgc    720
ccaatccaac ctacaagcca acaaaggata aaaagcgttc cttgacttct t ttattccag    780
tgattacgcg tcaaaaatta ttagttatca atattgtcat tgctgccttg t tggttaccc    840
tagtgagtat tttaggatca tattatttgc aaggtatcat tgataccat a tccccgata    900
acatgaaaaa cacccctaggg attgtgtcac tagggcttat tttgcgtat g ttatccaac    960
aactgctctc ttatgccaga gattatttat taattgtcat ggggcaacgc c tctcaattg   1020
```

-continued

| | | | | |
|---|---|---|---|---|
| atattatttt | gtcttatatc | aaacacattt | ttgaactgcc aatgtctttt t | tcgcgacgc | 1080 |
| gtcgtaccgg | tgaaattgtg | agccgtttta | cggacgctaa tgccattatt g | aagccctgg | 1140 |
| caagcacgat | gttatctgta | tttttagact | taggaatttt ggtcattgtt g | gcacagtgc | 1200 |
| tagtggttca | aaattcaacc | ttgtttctga | tttctctgat tgccattccg g | cttatgccc | 1260 |
| tagtggtctg | gctctttatg | cgtccttttt | caaagatgaa taatgaccaa a | tgcaagcag | 1320 |
| gttcgatgtt | aagttcttcc | attattgaag | atattaatgg cgttgagacg a | ttaaagcgc | 1380 |
| tgaatagtga | agaaaccgcc | tatcataaaa | ttgatcatga atttgtcact t | atttagaaa | 1440 |
| aatcatttgt | ttacgctaaa | acagaagcca | ctcaaaatgc gattaaaagc c | tcttacagc | 1500 |
| tctctttaaa | tgtcgtgatc | ttatgggttg | gcgcacaact ggtcatgacc a | ataaaatta | 1560 |
| gtgttggtca | actgatcact | tacaatgctt | tattaggatt ttttacagat c | ccttgcaaa | 1620 |
| atattattaa | tttacaaact | aagctccaac | aggcctcagt cgctaataat c | gtttgaacg | 1680 |
| aagtttattt | ggttgattca | gaatttaaag | ctagtcatca aatgacagaa a | gcattatgc | 1740 |
| ccaatagctc | attagtagcc | gatcatatca | cctataaata cggttttggt g | cgccagcaa | 1800 |
| ttgatgatgt | ttcactaacg | attacagccg | gtgaaaaaat cgctttggtt g | ggattagtg | 1860 |
| gatcaggtaa | atcaacttta | gttaaattgc | tggttaattt cttcaacca g | agtcaggga | 1920 |
| caatttcact | aggacaaaca | ccactcgcca | atcttgataa acatgagcta a | gagcacaca | 1980 |
| ttaattattt | accacaagaa | ccctttatat | tttccggttc aattatggac a | acctgttat | 2040 |
| tgggggctaa | gccagggaca | acccaagaag | atattatcag ggcggtagaa a | ttgctgaaa | 2100 |
| ttaaagatga | tattgaaaaa | atgtcgcaag | gatttggcac tgaactcgca g | aaagtggca | 2160 |
| atatttcggg | tggtcaaaaa | caacgcattg | ctttagctag agccatttta g | tcgattctc | 2220 |
| cggtgctgat | tttagatgag | tcaaccagta | atcttgatgt tttaacagaa a | aaagatta | 2280 |
| ttgataatct | catgcagtta | accgaaaaaa | ccattatctt tgtagcgcac c | gcttaacca | 2340 |
| tttcacagcg | agtagatcgt | attctaacca | tgcaaaacgg caaaattatc g | aagatggca | 2400 |
| cgcataatac | tctgcttaat | gccggtggtt | tctacgcgtc attgtttaat c | attaaggag | 2460 |
| acctgatgtt | tgatccaaaa | tacttagaaa | gtggcgaatt ttatcaacgt c | gttaccgca | 2520 |
| attttccaac | tctgattatt | gtgcctattt | tttttgttagt cgtgtttatc a | ttctattta | 2580 |
| gcctatttgc | taagcgtgaa | attgttgtca | agcaagtgg cgaaattatt c | cagccaaag | 2640 |
| tgctatcaga | tatccaatca | accagtaaca | atgccatcga tagtaaccaa t | taactgaaa | 2700 |
| ataaagtggt | taaaaaaggc | gataccttag | tgacctttac cagtggtaat g | aaaaaatat | 2760 |
| cgtctcaatt | actgacgcaa | caacttaata | atcttaacga ccgtctaaaa a | gtcttgata | 2820 |
| cctataagca | gagtattgtt | aacggacgta | gcgaatttgg tggcacagat c | aatttggtt | 2880 |
| atgatagtct | attcaacggc | tatatggcgc | aagttgatac gttgacgagt g | aatttaatc | 2940 |
| aacaaagtag | tgataaacaa | acagctgatc | aacaagctaa tcatcaaatt g | acgttttaa | 3000 |
| aacaaggtca | atctaaaaac | aatcaacaat | tagctaatta tcaagctatt c | taaccagta | 3060 |
| ttaatagcaa | cactaaaccg | actaataatc | cctatcaagc catttatgat a | attattcag | 3120 |
| cccagttaaa | atcagcacaa | acaactgatg | ataaagatca agtcaagcaa a | ctgccttaa | 3180 |
| gtaatgtaca | acaacaaatt | gatcaattac | aaacaacgag tagttcgtat g | atagtcaaa | 3240 |
| ttgctggtat | tacaaagagt | ggtccttatt | ctcaaagcag tacccttagat a | aaatcgctg | 3300 |
| acttgaagca | acaacaacta | gcgagtgctc | aaaaagaaat caatgatcag c | aacaatcct | 3360 |
| tagatgagtt | aaaagccaag | caatcctctg | ctaatgagga ttatcaagat a | cggttatta | 3420 |

-continued

```
aagcaccaga agatggcatt ttacatttag ccactgacaa aactaaaatc a gtatttcc     3480 ctaaaggcac aaccattgcg caaatttatc ctaaactgac gcaaaaaaca g ctttgaatg    3540 ttgagtacta tgtgcctgcc agtaatatta tcggcttaaa gcaagacaa g ccatccgtt    3600 ttgtagcaaa tcaaaatgtc acgaaaccgc tcaccttaaa cggaacaatc a aaagcatta   3660 gttctgcacc aatagccagt aaagagggat cctttataa attagtcgcg a cgattcagg    3720 ctagcaaaat agaccgtgaa cagattaaat atggtcttaa tggtcgaatc a caaccataa   3780 aagggactaa aacatggttt aattattata aagacattgt tttaggtgag a ataattagc    3840 taggaagata aacacaattt ttaaacgtgt ttatctttt tagtctcaat g aaattgtcg    3900 ccgaaggttt ttctagccaa gtggcaggac acagaaaaat gatagttgct a ctgaaggga   3960 agttcaactg ccaccaaaaa tagtaaccgc gcgacagcca accgccacca c aacagttat   4020 gctcgcccgt ggttattatt atcattaaca ctcttacgtc tttctatgat a cttttgagc   4080 cacattctta taatgctgca atcgaccttt tagaaaattg atctcatcag a aatttcttt   4140 taagtggtta tcatcagcat gtttactagc aatatttaat tctttaatcc t acgtttaat   4200 caacttagta gttttagtat ctttcatgta ttgattatct caaaaaaaca c ccaacaagg   4260 gcaatcagtt tgatttgagc agaggaagcc                                     4290

<210> SEQ ID NO 5
<211> LENGTH: 717
<212> TYPE: PRT
<213> ORGANISM: lcaC;

<400> SEQUENCE: 5

Met Phe Gln Lys Arg Ile Asn Tyr Ile Ala G ln Val Asp Glu Arg Asp
1               5                   10                  15

Cys Gly Val Ala Ala Leu Ala Met Val Leu T hr His Tyr Lys Thr Arg
            20                  25                  30

Leu Ser Leu Ala Lys Leu Arg Asp Leu Ala L ys Thr Asp Met Glu Gly
        35                  40                  45

Thr Thr Ala Leu Gly Ile Val Lys Ala Ala A sn Ala Leu Asp Phe Glu
    50                  55                  60

Thr Met Pro Ile Gln Ala Asp Leu Ser Leu P he Asp Lys Lys Asp Leu
65                  70                  75                  80

Pro Tyr Pro Phe Ile Ala His Val Ile Lys A sp Gly Lys Tyr Pro His
                85                  90                  95

Tyr Tyr Val Val Tyr Gly Ile Lys Gly Asp G ln Leu Leu Ile Ala Asp
            100                 105                 110

Pro Asp Asn Thr Val Gly Lys Asn Lys Met T hr Lys Ala His Phe Asn
        115                 120                 125

Glu Glu Trp Thr Gly Val Ser Ile Phe Ile A la Pro Asn Pro Thr Tyr
    130                 135                 140

Lys Pro Thr Lys Asp Lys Lys Arg Ser Leu T hr Ser Phe Ile Pro Val
145                 150                 155                 160

Ile Thr Arg Gln Lys Leu Leu Val Ile Asn I le Val Ile Ala Ala Leu
                165                 170                 175

Leu Val Thr Leu Val Ser Ile Leu Gly Ser T yr Tyr Leu Gln Gly Ile
            180                 185                 190

Ile Asp Thr Tyr Ile Pro Asp Asn Met Lys A sn Thr Leu Gly Ile Val
        195                 200                 205

Ser Leu Gly Leu Ile Phe Ala Tyr Val Ile G ln Gln Leu Leu Ser Tyr
```

-continued

```
            210                 215                 220
Ala Arg Asp Tyr Leu Leu Ile Val Met Gly Gln Arg Leu Ser Ile Asp
225                 230                 235                 240
Ile Ile Leu Ser Tyr Ile Lys His Ile Phe Glu Leu Pro Met Ser Phe
                245                 250                 255
Phe Ala Thr Arg Arg Thr Gly Glu Ile Val Ser Arg Phe Thr Asp Ala
            260                 265                 270
Asn Ala Ile Ile Glu Ala Leu Ala Ser Thr Met Leu Ser Val Phe Leu
        275                 280                 285
Asp Leu Gly Ile Leu Val Ile Val Gly Thr Val Leu Val Val Gln Asn
    290                 295                 300
Ser Thr Leu Phe Leu Ile Ser Leu Ile Ala Ile Pro Ala Tyr Ala Leu
305                 310                 315                 320
Val Val Trp Leu Phe Met Arg Pro Phe Ser Lys Met Asn Asn Asp Gln
                325                 330                 335
Met Gln Ala Gly Ser Met Leu Ser Ser Ser Ile Ile Glu Asp Ile Asn
            340                 345                 350
Gly Val Glu Thr Ile Lys Ala Leu Asn Ser Glu Glu Thr Ala Tyr His
        355                 360                 365
Lys Ile Asp His Glu Phe Val Thr Tyr Leu Glu Lys Ser Phe Val Tyr
    370                 375                 380
Ala Lys Thr Glu Ala Thr Gln Asn Ala Ile Lys Ser Leu Leu Gln Leu
385                 390                 395                 400
Ser Leu Asn Val Val Ile Leu Trp Val Gly Ala Gln Leu Val Met Thr
                405                 410                 415
Asn Lys Ile Ser Val Gly Gln Leu Ile Thr Tyr Asn Ala Leu Leu Gly
            420                 425                 430
Phe Phe Thr Asp Pro Leu Gln Asn Ile Ile Asn Leu Gln Thr Lys Leu
        435                 440                 445
Gln Gln Ala Ser Val Ala Asn Asn Arg Leu Asn Glu Val Tyr Leu Val
    450                 455                 460
Asp Ser Glu Phe Lys Ala Ser His Gln Met Thr Glu Ser Ile Met Pro
465                 470                 475                 480
Asn Ser Ser Leu Val Ala Asp His Ile Thr Tyr Lys Tyr Gly Phe Gly
                485                 490                 495
Ala Pro Ala Ile Asp Asp Val Ser Leu Thr Ile Thr Ala Gly Glu Lys
            500                 505                 510
Ile Ala Leu Val Gly Ile Ser Gly Ser Gly Lys Ser Thr Leu Val Lys
        515                 520                 525
Leu Leu Val Asn Phe Phe Gln Pro Glu Ser Gly Thr Ile Ser Leu Gly
    530                 535                 540
Gln Thr Pro Leu Ala Asn Leu Asp Lys His Glu Leu Arg Ala His Ile
545                 550                 555                 560
Asn Tyr Leu Pro Gln Glu Pro Phe Ile Phe Ser Gly Ser Ile Met Asp
                565                 570                 575
Asn Leu Leu Gly Ala Lys Pro Gly Thr Thr Gln Glu Asp Ile Ile
            580                 585                 590
Arg Ala Val Glu Ile Ala Glu Ile Lys Asp Asp Ile Glu Lys Met Ser
        595                 600                 605
Gln Gly Phe Gly Thr Glu Leu Ala Glu Ser Gly Asn Ile Ser Gly Gly
    610                 615                 620
Gln Lys Gln Arg Ile Ala Leu Ala Arg Ala Ile Leu Val Asp Ser Pro
625                 630                 635                 640
```

```
Val Leu Ile Leu Asp Glu Ser Thr Ser Asn Leu Asp Val Leu Thr Glu
                645                 650                 655

Lys Lys Ile Ile Asp Asn Leu Met Gln Leu Thr Glu Lys Thr Ile Ile
            660                 665                 670

Phe Val Ala His Arg Leu Thr Ile Ser Gln Arg Val Asp Arg Ile Leu
        675                 680                 685

Thr Met Gln Asn Gly Lys Ile Ile Glu Asp Gly Thr His Asn Thr Leu
    690                 695                 700

Leu Asn Ala Gly Gly Phe Tyr Ala Ser Leu Phe Asn His
705                 710                 715

<210> SEQ ID NO 6
<211> LENGTH: 457
<212> TYPE: PRT
<213> ORGANISM: lcaD;

<400> SEQUENCE: 6

Met Phe Asp Pro Lys Tyr Leu Glu Ser Gly Glu Phe Tyr Gln Arg Arg
1               5                   10                  15

Tyr Arg Asn Phe Pro Thr Leu Ile Ile Val Pro Ile Phe Leu Leu Val
            20                  25                  30

Val Phe Ile Ile Leu Phe Ser Leu Phe Ala Lys Arg Glu Ile Val Val
        35                  40                  45

Lys Ala Ser Gly Glu Ile Ile Pro Ala Lys Val Leu Ser Asp Ile Gln
    50                  55                  60

Ser Thr Ser Asn Asn Ala Ile Asp Ser Asn Gln Leu Thr Glu Asn Lys
65                  70                  75                  80

Val Val Lys Lys Gly Asp Thr Leu Val Thr Phe Thr Ser Gly Asn Glu
                85                  90                  95

Lys Ile Ser Ser Gln Leu Leu Thr Gln Gln Leu Asn Asn Leu Asn Asp
            100                 105                 110

Arg Leu Lys Ser Leu Asp Thr Tyr Lys Gln Ser Ile Val Asn Gly Arg
        115                 120                 125

Ser Glu Phe Gly Gly Thr Asp Gln Phe Gly Tyr Asp Ser Leu Phe Asn
    130                 135                 140

Gly Tyr Met Ala Gln Val Asp Thr Leu Thr Ser Glu Phe Asn Gln Gln
145                 150                 155                 160

Ser Ser Asp Lys Gln Thr Ala Asp Gln Gln Ala Asn His Gln Ile Asp
                165                 170                 175

Val Leu Lys Gln Gly Gln Ser Lys Asn Asn Gln Gln Leu Ala Asn Tyr
            180                 185                 190

Gln Ala Ile Leu Thr Ser Ile Asn Ser Asn Thr Lys Pro Thr Asn Asn
        195                 200                 205

Pro Tyr Gln Ala Ile Tyr Asp Asn Tyr Ser Ala Gln Leu Lys Ser Ala
    210                 215                 220

Gln Thr Thr Asp Asp Lys Asp Gln Val Lys Gln Thr Ala Leu Ser Asn
225                 230                 235                 240

Val Gln Gln Gln Ile Asp Gln Leu Gln Thr Thr Ser Ser Ser Tyr Asp
                245                 250                 255

Ser Gln Ile Ala Gly Ile Thr Lys Ser Gly Pro Leu Ser Gln Ser Ser
            260                 265                 270

Thr Leu Asp Lys Ile Ala Asp Leu Lys Gln Gln Gln Leu Ala Ser Ala
        275                 280                 285

Gln Lys Glu Ile Asn Asp Gln Gln Gln Ser Leu Asp Glu Leu Lys Ala
```

```
                    290               295               300
Lys Gln Ser Ser Ala Asn Glu Asp Tyr Gln Asp Thr Val Ile Lys Ala
305                 310               315                 320

Pro Glu Asp Gly Ile Leu His Leu Ala Thr Asp Lys Thr Lys Ile Lys
                325               330               335

Tyr Phe Pro Lys Gly Thr Thr Ile Ala Gln Ile Tyr Pro Lys Leu Thr
            340               345               350

Gln Lys Thr Ala Leu Asn Val Glu Tyr Tyr Val Pro Ala Ser Asn Ile
        355               360               365

Ile Gly Leu Lys Gln Arg Gln Ala Ile Arg Phe Val Ala Asn Gln Asn
        370               375               380

Val Thr Lys Pro Leu Thr Leu Asn Gly Thr Ile Lys Ser Ile Ser Ser
385                 390               395                 400

Ala Pro Ile Ala Ser Lys Glu Gly Ser Phe Tyr Lys Leu Val Ala Thr
                405               410               415

Ile Gln Ala Ser Lys Ile Asp Arg Glu Gln Ile Lys Tyr Gly Leu Asn
            420               425               430

Gly Arg Ile Thr Thr Ile Lys Gly Thr Lys Thr Trp Phe Asn Tyr Tyr
        435               440               445

Lys Asp Ile Val Leu Gly Glu Asn Asn
    450               455
```

<210> SEQ ID NO 7
<211> LENGTH: 35
<212> TYPE: PRT
<213> ORGANISM: Divergicin N-terminal;
<220> FEATURE:
<221> NAME/KEY: Cleavage_site
<222> LOCATION: (29)..(30)
<223> OTHER INFORMATION:

<400> SEQUENCE: 7

```
Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala Ala Ala Pro
            20                  25                  30

Lys Ile Thr
        35
```

<210> SEQ ID NO 8
<211> LENGTH: 29
<212> TYPE: PRT
<213> ORGANISM: Divergicin N-terminal;

<400> SEQUENCE: 8

```
Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala
            20                  25
```

<210> SEQ ID NO 9
<211> LENGTH: 30
<212> TYPE: PRT
<213> ORGANISM: Leucocin N-terminal;
<220> FEATURE:
<221> NAME/KEY: cleavage_site
<222> LOCATION: (24)..(25)
<223> OTHER INFORMATION:

<400> SEQUENCE: 9

-continued

Met Met Asn Met Lys Pro Thr Glu Ser Tyr G lu Gln Leu Asp Asn Ser
1               5                   10                  15

Ala Leu Glu Gln Val Val Gly Gly Lys Tyr T yr Gly Asn Gly
            20                  25                  30

<210> SEQ ID NO 10
<211> LENGTH: 24
<212> TYPE: PRT
<213> ORGANISM: Leucocin N-terminal;

<400> SEQUENCE: 10

Met Met Asn Met Lys Pro Thr Glu Ser Tyr G lu Gln Leu Asp Asn Ser
1               5                   10                  15

Ala Leu Glu Gln Val Val Gly Gly
            20

<210> SEQ ID NO 11
<211> LENGTH: 27
<212> TYPE: PRT
<213> ORGANISM: Lactococcin A N-terminal;
<220> FEATURE:
<221> NAME/KEY: cleavage_site
<222> LOCATION: (21)..(22)
<223> OTHER INFORMATION:

<400> SEQUENCE: 11

Met Lys Asn Gln Leu Asn Phe Asn Ile Val S er Asp Glu Glu Leu Ser
1               5                   10                  15

Glu Ala Asn Gly Gly Lys Leu Thr Phe Ile G ln
            20                  25

<210> SEQ ID NO 12
<211> LENGTH: 21
<212> TYPE: PRT
<213> ORGANISM: Lactococcin A;

<400> SEQUENCE: 12

Met Lys Asn Gln Leu Asn Phe Asn Ile Val S er Asp Glu Glu Leu Ser
1               5                   10                  15

Glu Ala Asn Gly Gly
            20

<210> SEQ ID NO 13
<211> LENGTH: 21
<212> TYPE: PRT
<213> ORGANISM: colicin V N-terminal;
<220> FEATURE:
<221> NAME/KEY: cleavage_site
<222> LOCATION: (15)..(16)
<223> OTHER INFORMATION:

<400> SEQUENCE: 13

Met Arg Thr Leu Thr Leu Asn Glu Leu Asp S er Val Ser Gly Gly Ala
1               5                   10                  15

Ser Gly Arg Asp Ile
            20

<210> SEQ ID NO 14
<211> LENGTH: 15
<212> TYPE: PRT
<213> ORGANISM: colicin V;

<400> SEQUENCE: 14

Met Arg Thr Leu Thr Leu Asn Glu Leu Asp S er Val Ser Gly Gly

-continued 1          5              10             15

<210> SEQ ID NO 15
<211> LENGTH: 3475
<212> TYPE: DNA
<213> ORGANISM: plasmid;

<400> SEQUENCE: 15

| | | | | |
|---|---|---|---|---|
| gatatcttgg | tattacaaac | taattggagg | ttggtatata | tgaaaaaaca a attttaaaa | 60 |
| gggttggtta | tagttgtttg | tttatctggg | gcaacatttt | tctcaacacc a caacaagct | 120 |
| tctgctgctg | caccgaaaat | tactcaaaaa | caaaaaaatt | gtgttaatgg a caattaggt | 180 |
| ggaatgcttc | tggagctttt | gggtggacct | ggcggagttg | tgttaggtgg t ataggtggt | 240 |
| gcaatagcag | gaggttgttt | taattaaatg | aaaataaaat | ggtactggga a tctctgatt | 300 |
| gaaaccttaa | tatttataat | tgttcttctt | gtattttttt | atagaagttc t ggttttttct | 360 |
| ttaaaaaatt | tagttttagg | aagtttattt | tatttgatag | caattggtct t tttaattat | 420 |
| aaaaagataa | acaaatagcc | actattttta | aatttacaac | ttttgcattt t aagtatatt | 480 |
| gttgttatta | ttaaggtgcg | agatgagata | aggtctacat | ggacagcaca a aacccaccc | 540 |
| ctaatgcgaa | taggggtggg | tttttttcgt | tcgttgcgaa | tacgaacgtg t gggttagag | 600 |
| acaacttgcg | agattatcgt | ctaatcatct | aaccaatgat | ccactagtat t aatactagt | 660 |
| cccacaaaaa | gtggagcaat | aaccaatgag | ataaggtttt | ccataaacag c cccccttt | 720 |
| caggggcaag | ttgccactta | ctaatatagc | acagctcctt | tattgttctt a gtctaaatc | 780 |
| tgataaatct | tttcttgttc | aaaaatatag | accacttaaa | agcttataac g gtactagat | 840 |
| ttttcagata | ccccaattac | ctacttaaaa | cgtctctctt | tttcgtttta a gatgtttaa | 900 |
| aattatttttc | tatgaattat | acacaaatgt | gcttaaatcg | tcttaaatcg t cttaaaatg | 960 |
| tggtctgtgt | tgagaataca | acgactttgt | ttggtcgtac | ctctaaatct g tttgctgtg | 1020 |
| aacgagggta | gcgaagtgaa | cttttgttg | ctaacgctct | tggttttgtc t tttgatttt | 1080 |
| ataaaatgtg | gatgtaatcc | actccttact | agggtttaa | tctttataaa a taaggagc | 1140 |
| ttgcgaatgc | aaggtgccct | ttttctttg | tctgactact | agggacaaat t atctgagta | 1200 |
| tgaacaagat | tttgtctgtt | cttgcgcgta | tttattaata | tatatttaa g agatatttt | 1260 |
| aagagatatt | ttaaaacctt | tttagggggtg | agctcagcct | tagagagagt a agcattgaa | 1320 |
| gcatagtact | agggacaaat | tatctgacta | ctagggataa | attatctgac t actagggac | 1380 |
| aaattatctg | actactaggg | ataaattatc | tgactactag | ggacgcactt t actttgtgt | 1440 |
| atcgtatcgt | ttataatctt | tatatgtgag | gggaggtcga | aaggattgga a aagaaaacg | 1500 |
| aatttaaaaa | ttgcatatca | aaatgaattg | aatctggttc | cacttaaaaa t ttcaatgct | 1560 |
| aaacaaatgg | atttattctt | tgctttgtgt | gcccgaatga | aaaataaagg g cttagaaag | 1620 |
| gtatctttta | cgtttgaaga | actaagagaa | ctaagtgatt | acaagataac t gctatcgaa | 1680 |
| ccgttcacga | atgatttaga | acaattatac | aaaaaaatgt | taaacctaac a tacagaacg | 1740 |
| gagacagaaa | caaaaatcag | ttatttcgtt | ttatttactg | ggtttgtgat t gataaatca | 1800 |
| gagcaaattg | ttgaagttag | tgtaaaaccca | gacttagaac | atatcattaa c ggtatctct | 1860 |
| agtgagttca | ataaatttga | gttactagca | ttcacaagta | tccagtcgaa a tatacgaaa | 1920 |
| acactcttta | gattgcttat | gcagtttcaa | tcaactgggt | tttatgtggt t aaaattgaa | 1980 |
| gatttcagag | cactttttaga | cattccaaaa | tcttatcaaa | tgactgacat a acccaacgg | 2040 |
| atattgaaac | ctagtttaat | tgagttaagt | cagtacttta | atgatttaaa a gttaataaa | 2100 |

```
attaaagctc gaaagggtaa taaaatagac cgtttagaat tcactttctc c ggtctaaag    2160 actgatttac ctaaagttcc attgcacgac tggacgaaat aaaaaaagga c ctcccctc     2220 acatttaagc aagtaggaac gtccctcgca atccacgaag actgctgatt c attttagca    2280 tatattgtgc gggacttcta ataaaattat atttggaggt cattttttatg t cgaataagt   2340 acttgaaaaa aagaaagcgt caagctaagc aggtagctga tttgtacgat t taattattg    2400 gggttgaaca tgctggcagc tcgttaattg cgttgtatga gggaattaaa c cctctcaat    2460 atcgaatttt tattcttttg tcttattcta gtttgaaaa taaattaaac t tatacaaca    2520 aagcgatttt aagaactgaa gtttattctt tagaaaaaaa attaaacgaa a aaataaatg    2580 ctcaaatcag aattgcgcaa aaaataaaa aagaaattgc ggtaattgat t tcacaaaac    2640 aaaaagaaaa actcaaaaga gaattactta gttttgaaaa tgataaagaa a tgaaactta    2700 tggattcgca attaaaacaa tttcatgaaa ataaaacgtt agctgatatt a atgatcagt    2760 tttttatgac ggtacaaaat agtttaattt tgctgcataa aaaagcacct t taacattaa    2820 aattaatttg tttgaaaaat tatattcgcc tttgcaaaaa ttattttcta a agaatatat    2880 tttaatgttt tttgaaaaaa atagtaacat gggaacatgt tgctctgctc g caaaaggaa    2940 aaatatttaa actaataaaa aaccgtcgga gaccagccaa ccaataggtt g ctttaagt    3000 ttaagcctac gttgacaact gtcaatgtat aagtgcgccc tttgggtgtt t tattttttg    3060 tttaactatt attttctgca taggtttttt attttttatta atttgatttt c aagaaaggg    3120 atgaacctaa aatgatttat aaacaaaaaa agaaagaaga tgttttttgga t ttcctaaag    3180 ttttaacaat tgctgatttg agtacgagat ggaaaatgtc acgtcaagct a tccataaaa    3240 aaattcaaga agatttatta tttcctatgc ctgttcaaat tgtctcaaat g gaaaaatta    3300 aattgttttt atttgttgat attgaaaaat acgaaaaaaa tcgtccgtgg t tattagaca    3360 ttaattatcg aaatgaacga caactttgga tttacaaaaa tggttttttt a aatagcaag    3420 ttagtcaatt accttatacc ttgttggata tctttggata aaaaaatagt t gtat         3475
```

<210> SEQ ID NO 16
<211> LENGTH: 227
<212> TYPE: DNA
<213> ORGANISM: Divergicin structural gene;
<220> FEATURE:
<221> NAME/KEY: CDS
<222> LOCATION: (1)..(225)
<223> OTHER INFORMATION:

<400> SEQUENCE: 16

```
atg aaa aaa caa att tta aaa ggg ttg gtt a ta gtt gtt tgt tta tct          48
Met Lys Lys Gln Ile Leu Lys Gly Leu Val I le Val Val Cys Leu Ser
1               5                   10                  15 ggg gca aca ttt ttc tca aca cca caa caa g ct tct gct gct gca ccg          96
Gly Ala Thr Phe Phe Ser Thr Pro Gln Gln A la Ser Ala Ala Ala Pro
            20                  25                  30 aaa att act caa aaa caa aaa aat tgt gtt a at gga caa tta ggt gga         144
Lys Ile Thr Gln Lys Gln Lys Asn Cys Val A sn Gly Gln Leu Gly Gly
        35                  40                  45 atg ctt gct gga gct ttg ggt gga cct ggc g ga gtt gtg tta ggt ggt         192
Met Leu Ala Gly Ala Leu Gly Gly Pro Gly G ly Val Val Leu Gly Gly
    50                  55                  60 ata ggt ggt gca ata gca gga ggt tgt ttt a at ta                          227
Ile Gly Gly Ala Ile Ala Gly Gly Cys Phe A sn
65                  70                  75
```

```
<210> SEQ ID NO 17
<211> LENGTH: 75
<212> TYPE: PRT
<213> ORGANISM: Divergicin structural gene;

<400> SEQUENCE: 17

Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala Ala Ala Pro
            20                  25                  30

Lys Ile Thr Gln Lys Gln Lys Asn Cys Val Asn Gly Gln Leu Gly Gly
        35                  40                  45

Met Leu Ala Gly Ala Leu Gly Gly Pro Gly Gly Val Val Leu Gly Gly
    50                  55                  60

Ile Gly Gly Ala Ile Ala Gly Gly Cys Phe Asn
65                  70                  75

<210> SEQ ID NO 18
<211> LENGTH: 75
<212> TYPE: PRT
<213> ORGANISM: Divergicin structural gene

<400> SEQUENCE: 18

Met Lys Lys Gln Ile Leu Lys Gly Leu Val Ile Val Val Cys Leu Ser
1               5                   10                  15

Gly Ala Thr Phe Phe Ser Thr Pro Gln Gln Ala Ser Ala Ala Ala Pro
            20                  25                  30

Lys Ile Thr Gln Lys Gln Lys Asn Cys Val Asn Gly Gln Leu Gly Gly
        35                  40                  45

Met Leu Ala Gly Ala Leu Gly Gly Pro Gly Gly Val Val Leu Gly Gly
    50                  55                  60

Ile Gly Gly Ala Ile Ala Gly Gly Cys Phe Asn
65                  70                  75

<210> SEQ ID NO 19
<211> LENGTH: 170
<212> TYPE: DNA
<213> ORGANISM: divergicin immunity gene;
<220> FEATURE:
<221> NAME/KEY: CDS
<222> LOCATION: (1)..(168)
<223> OTHER INFORMATION:

<400> SEQUENCE: 19 atg aaa ata aaa tgg tac tgg gaa tct ctg att gaa acc tta ata ttt      48
Met Lys Ile Lys Trp Tyr Trp Glu Ser Leu Ile Glu Thr Leu Ile Phe
1               5                   10                  15 ata att gtt ctt ctt gta ttt ttt tat aga agt tct ggt ttt tct tta      96
Ile Ile Val Leu Leu Val Phe Phe Tyr Arg Ser Ser Gly Phe Ser Leu
            20                  25                  30 aaa aat tta gtt tta gga agt tta ttt tat ttg ata gca att ggt ctt     144
Lys Asn Leu Val Leu Gly Ser Leu Phe Tyr Leu Ile Ala Ile Gly Leu
        35                  40                  45 ttt aat tat aaa aag ata aac aaa ta                                  170
Phe Asn Tyr Lys Lys Ile Asn Lys
    50                  55

<210> SEQ ID NO 20
<211> LENGTH: 56
<212> TYPE: PRT
<213> ORGANISM: divergicin immunity gene;
```

<400> SEQUENCE: 20

Met Lys Ile Lys Trp Tyr Trp Glu Ser Leu I le Glu Thr Leu Ile Phe
1               5                   10                  15

Ile Ile Val Leu Leu Val Phe Phe Tyr Arg S er Ser Gly Phe Ser Leu
            20                  25                  30

Lys Asn Leu Val Leu Gly Ser Leu Phe Tyr L eu Ile Ala Ile Gly Leu
            35                  40                  45

Phe Asn Tyr Lys Lys Ile Asn Lys
    50                  55

<210> SEQ ID NO 21
<211> LENGTH: 56
<212> TYPE: PRT
<213> ORGANISM: Divergicin immunity gene

<400> SEQUENCE: 21

Met Lys Ile Lys Trp Tyr Trp Glu Ser Leu I le Glu Thr Leu Ile Phe
1               5                   10                  15

Ile Ile Val Leu Leu Val Phe Phe Tyr Arg S er Ser Gly Phe Ser Leu
            20                  25                  30

Lys Asn Leu Val Leu Gly Ser Leu Phe Tyr L eu Ile Ala Ile Gly Leu
            35                  40                  45

Phe Asn Tyr Lys Lys Ile Asn Lys
    50                  55

<210> SEQ ID NO 22
<211> LENGTH: 124
<212> TYPE: DNA
<213> ORGANISM: Divergicin signal peptide;
<220> FEATURE:
<221> NAME/KEY: sig_peptide
<222> LOCATION: (1)..(123)
<223> OTHER INFORMATION:
<221> NAME/KEY: CDS
<222> LOCATION: (1)..(123)
<223> OTHER INFORMATION:

<400> SEQUENCE: 22 atc ttg gta tca caa act aat ttg gag gtt g gt ata tat gaa aaa aca     48
Ile Leu Val Ser Gln Thr Asn Leu Glu Val G ly Ile Tyr Glu Lys Thr
1               5                   10                  15 aat ttt aaa agg gtt ggt tat agt tgt ttg t tt atc tgg ggc aac att     96
Asn Phe Lys Arg Val Gly Tyr Ser Cys Leu P he Ile Trp Gly Asn Ile
            20                  25                  30 ttt ctc aac acc aca aca agc ttc tgc t                               124
Phe Leu Asn Thr Thr Thr Ser Phe Cys
            35                  40

<210> SEQ ID NO 23
<211> LENGTH: 41
<212> TYPE: PRT
<213> ORGANISM: Divergicin signal peptide;

<400> SEQUENCE: 23

Ile Leu Val Ser Gln Thr Asn Leu Glu Val G ly Ile Tyr Glu Lys Thr
1               5                   10                  15

Asn Phe Lys Arg Val Gly Tyr Ser Cys Leu P he Ile Trp Gly Asn Ile
            20                  25                  30

Phe Leu Asn Thr Thr Thr Ser Phe Cys
            35                  40

```
<210> SEQ ID NO 24
<211> LENGTH: 41
<212> TYPE: PRT
<213> ORGANISM: divergicin signal peptide

<400> SEQUENCE: 24

Ile Leu Val Ser Gln Thr Asn Leu Glu Val G ly Ile Tyr Glu Lys Thr
1               5                   10                  15

Asn Phe Lys Arg Val Gly Tyr Ser Cys Leu P he Ile Trp Gly Asn Ile
            20                  25                  30

Phe Leu Asn Thr Thr Thr Ser Phe Cys
            35                  40

<210> SEQ ID NO 25
<211> LENGTH: 675
<212> TYPE: DNA
<213> ORGANISM: Brochocin-C;

<400> SEQUENCE: 25
gctattttga gaaatattaa ccaatagtaa aaattatcat gctatctttt g tatgtaata      60 aaaattattt aaaggagggt gtttcatcat gcacaaggta aaaaaattaa a caatcaaga    120 gttacaacag atcgtgggag gttacagttc aaaagattgt ctaaaagata t tggtaaagg    180 aattggtgct ggtacagtag ctggggcagc cggcggtggc ctagctgcag g attaggtgc    240 tatcccagga gcattcgttg agcacatttt ggagtaatc ggcggatctg c cgcatgcat    300 tggtggatta ttaggtaact aggaggttat atttatgaaa aagaactat t gaataaaaa    360 tgaaatgagt agaattatcg gcggcaaaat aaattgggga atgttggcg g ttcttgtgt    420 tggaggtgca gtaattggag gcgccctcgg tggactaggt ggagctggcg g aggttgcat    480 tacaggagct atcggaagta tttgggatca atggtaaaaa ctatactatt t tcggttgta    540 atttcattcg ttgcattatg taactttta ataaaaaag atgtgtcttc a aaaaaaaa    600 ttatttttaa caggttctat tgctgtcttt ctaattatct atgattttct a tggattata    660 ttctctaact agtac                                                       675

<210> SEQ ID NO 26
<211> LENGTH: 233
<212> TYPE: DNA
<213> ORGANISM: Brochocin-C peptide A;
<220> FEATURE:
<221> NAME/KEY: CDS
<222> LOCATION: (1)..(231)
<223> OTHER INFORMATION:
<221> NAME/KEY: sig_peptide
<222> LOCATION: (1)..(54)
<223> OTHER INFORMATION:

<400> SEQUENCE: 26 atg cac aag gta aaa aaa tta aac aat caa g ag tta caa cag atc gtg          48
Met His Lys Val Lys Lys Leu Asn Asn Gln G lu Leu Gln Gln Ile Val
1               5                   10                  15 gga ggt tac agt tca aaa gat tgt cta aaa g at att ggt aaa gga att          96
Gly Gly Tyr Ser Ser Lys Asp Cys Leu Lys A sp Ile Gly Lys Gly Ile
            20                  25                  30 ggt gct ggt aca gta gct ggg gca gcc ggc g gt ggc cta gct gca gga         144
Gly Ala Gly Thr Val Ala Gly Ala Ala Gly G ly Gly Leu Ala Ala Gly
        35                  40                  45 tta ggt gct atc cca gga gca ttc gtt gga g ca cat ttt gga gta atc         192
Leu Gly Ala Ile Pro Gly Ala Phe Val Gly A la His Phe Gly Val Ile
    50                  55                  60
```

```
ggc gga tct gcc gca tgc att ggt gga tta t ta ggt aac ta          233
Gly Gly Ser Ala Ala Cys Ile Gly Gly Leu L eu Gly Asn
65                  70                  75

<210> SEQ ID NO 27
<211> LENGTH: 77
<212> TYPE: PRT
<213> ORGANISM: Brochocin-C peptide A;

<400> SEQUENCE: 27

Met His Lys Val Lys Lys Leu Asn Asn Gln G lu Leu Gln Gln Ile Val
1               5                   10                  15

Gly Gly Tyr Ser Ser Lys Asp Cys Leu Lys A sp Ile Gly Lys Gly Ile
                20                  25                  30

Gly Ala Gly Thr Val Ala Gly Ala Ala Gly G ly Gly Leu Ala Ala Gly
        35                  40                  45

Leu Gly Ala Ile Pro Gly Ala Phe Val Gly A la His Phe Gly Val Ile
    50                  55                  60

Gly Gly Ser Ala Ala Cys Ile Gly Gly Leu L eu Gly Asn
65                  70                  75

<210> SEQ ID NO 28
<211> LENGTH: 77
<212> TYPE: PRT
<213> ORGANISM: brochocin C, peptide A

<400> SEQUENCE: 28

Met His Lys Val Lys Lys Leu Asn Asn Gln G lu Leu Gln Gln Ile Val
1               5                   10                  15

Gly Gly Tyr Ser Ser Lys Asp Cys Leu Lys A sp Ile Gly Lys Gly Ile
                20                  25                  30

Gly Ala Gly Thr Val Ala Gly Ala Ala Gly G ly Gly Leu Ala Ala Gly
        35                  40                  45

Leu Gly Ala Ile Pro Gly Ala Phe Val Gly A la His Phe Gly Val Ile
    50                  55                  60

Gly Gly Ser Ala Ala Cys Ile Gly Gly Leu L eu Gly Asn
65                  70                  75

<210> SEQ ID NO 29
<211> LENGTH: 182
<212> TYPE: DNA
<213> ORGANISM: Brochocin-C peptide B;
<220> FEATURE:
<221> NAME/KEY: CDS
<222> LOCATION: (1)..(177)
<223> OTHER INFORMATION:
<221> NAME/KEY: sig_peptide
<222> LOCATION: (1)..(51)
<223> OTHER INFORMATION:

<400> SEQUENCE: 29 atg aaa aaa gaa cta ttg aat aaa aat gaa a tg agt aga att atc ggc   48
Met Lys Lys Glu Leu Leu Asn Lys Asn Glu M et Ser Arg Ile Ile Gly
1               5                   10                  15 ggc aaa ata aat tgg gga aat gtt ggc ggt t ct tgt gtt gga ggt gca   96
Gly Lys Ile Asn Trp Gly Asn Val Gly Gly S er Cys Val Gly Gly Ala
                20                  25                  30 gta att gga ggc gcc ctc ggt gga cta ggt g ga gct ggc gga ggt tgc  144
Val Ile Gly Gly Ala Leu Gly Gly Leu Gly G ly Ala Gly Gly Gly Cys
        35                  40                  45 att aca gga gct atc gga agt att tgg gat c aa tggta                182
```

```
Ile Thr Gly Ala Ile Gly Ser Ile Trp Asp G ln
    50                  55
```

<210> SEQ ID NO 30
<211> LENGTH: 59
<212> TYPE: PRT
<213> ORGANISM: Brochocin-C peptide B;

<400> SEQUENCE: 30

```
Met Lys Lys Glu Leu Leu Asn Lys Asn Glu M et Ser Arg Ile Ile Gly
1               5                  10                  15

Gly Lys Ile Asn Trp Gly Asn Val Gly Gly S er Cys Val Gly Gly Ala
            20                  25                  30

Val Ile Gly Gly Ala Leu Gly Gly Leu Gly G ly Ala Gly Gly Gly Cys
        35                  40                  45

Ile Thr Gly Ala Ile Gly Ser Ile Trp Asp G ln
    50                  55
```

<210> SEQ ID NO 31
<211> LENGTH: 60
<212> TYPE: PRT
<213> ORGANISM: Brochocin-C, peptide B

<400> SEQUENCE: 31

```
Met Lys Lys Glu Leu Leu Asn Lys Asn Glu M et Ser Arg Ile Ile Gly
1               5                  10                  15

Gly Lys Ile Asn Trp Gly Asn Val Gly Gly S er Cys Val Gly Gly Ala
            20                  25                  30

Val Ile Gly Gly Ala Leu Gly Gly Leu Gly G ly Ala Gly Gly Gly Cys
        35                  40                  45

Ile Thr Gly Ala Ile Gly Ser Ile Trp Asp G ln Trp
    50                  55                  60
```

<210> SEQ ID NO 32
<211> LENGTH: 161
<212> TYPE: DNA
<213> ORGANISM: Brochocin-C immunity peptide;
<220> FEATURE:
<221> NAME/KEY: CDS
<222> LOCATION: (1)..(159)
<223> OTHER INFORMATION:

<400> SEQUENCE: 32

```
atg gta aaa act ata cta ttt tcg gtt gta a tt tca ttc gtt gca tta        48
Met Val Lys Thr Ile Leu Phe Ser Val Val I le Ser Phe Val Ala Leu
1               5                  10                  15 tgt aac ttt tta ata aaa aaa gat gtg tct t ca aaa aaa aaa tta ttt        96
Cys Asn Phe Leu Ile Lys Lys Asp Val Ser S er Lys Lys Lys Leu Phe
            20                  25                  30 tta aca ggt tct att gct gtc ttt cta att a tc tat gat ttt cta tgg      144
Leu Thr Gly Ser Ile Ala Val Phe Leu Ile I le Tyr Asp Phe Leu Trp
        35                  40                  45 att ata ttc tct aac ta                                                 161
Ile Ile Phe Ser Asn
    50
```

<210> SEQ ID NO 33
<211> LENGTH: 53
<212> TYPE: PRT
<213> ORGANISM: Brochocin-C immunity peptide;

<400> SEQUENCE: 33

```
Met Val Lys Thr Ile Leu Phe Ser Val Val Ile Ser Phe Val Ala Leu
1               5                   10                  15

Cys Asn Phe Leu Ile Lys Lys Asp Val Ser Ser Lys Lys Lys Leu Phe
                20                  25                  30

Leu Thr Gly Ser Ile Ala Val Phe Leu Ile Ile Tyr Asp Phe Leu Trp
            35                  40                  45

Ile Ile Phe Ser Asn
    50
```

<210> SEQ ID NO 34
<211> LENGTH: 53
<212> TYPE: PRT
<213> ORGANISM: Brochocin-C immunity peptide

<400> SEQUENCE: 34

```
Met Val Lys Thr Ile Leu Phe Ser Val Val Ile Ser Phe Val Ala Leu
1               5                   10                  15

Cys Asn Phe Leu Ile Lys Lys Asp Val Ser Ser Lys Lys Lys Leu Phe
                20                  25                  30

Leu Thr Gly Ser Ile Ala Val Phe Leu Ile Ile Tyr Asp Phe Leu Trp
            35                  40                  45

Ile Ile Phe Ser Asn
    50
```

<210> SEQ ID NO 35
<211> LENGTH: 2226
<212> TYPE: DNA
<213> ORGANISM: Enterocin 900 operon;

<400> SEQUENCE: 35

| | |
|---|---|
| aagctttact tgatattagt tctgagttct gcctgattta tcagtaacat a actctagag | 60 |
| ataactgcgt cgctatctca agttcttttt tcttttctta caaataaat a tactttatt | 120 |
| tcattttata agtcaacgtt ttcattgctt ataaattagt tttttttaatc a tctcagtaa | 180 |
| taatttgcta tgtcagttcg atcaatacca tttgcatgaa agtacagcta t aagccaatc | 240 |
| acacctaacc tactcttaat cgtataatga ttccagttag caaggtcttt a atactcatg | 300 |
| atccccatct ggttgagttt ttttcattcg aaacccctatg ccccaaaaga c cgtcatttt | 360 |
| aggaatattc catactttct caggaacatt ttgatacgtc cattcagcaa t aaacccttc | 420 |
| attgtgcttc gcttcattgt ctaaggcgag tttggccaaa ggggattatc t ccgcgacac | 480 |
| ctaccgtagc aatcaatcct aattcttctt taatacgttc cttggatcat t gaacgaat | 540 |
| tttttccttc tctgacttct tgttccttca gtcgtaaaaa tattcagtga t ctggtcact | 600 |
| tttaaaatgg gttcatcgat tggatacatc agtagatctt cgtcagccac a tatcttttg | 660 |
| aaaatattat ttacccgcat atttcgcttg atatataggt tcatacgtgg t ggaacaacg | 720 |
| tatgatgttt taggaaatag ttgtgataaa tcacgtggtc tactcacatt t gtaatatca | 780 |
| taccgctttt ttgcttcagg agaagaagct ctaatatcaa tcctaaacca g tattgtcag | 840 |
| cgcgactcat aacaacaagt tctgttgtta atggatcaaa atttctttct a tacactcga | 900 |
| tactcgcata aaaaggcttc atgtcgatta gaaataatc atttactgat t ctttcgaat | 960 |
| aatccagcat gaataacacc cattctttt cacattacac aaacgtaagt t aggaaatat | 1020 |
| aaagaagaaa actaaatagc actaaacaaa caagacaact catgcttatt c cgtataaga | 1080 |
| aactacatat tatgttaact agttattaaa ataacatatt taataaaatt a aattgtgat | 1140 |
| tttataggtt tcaggaatga aaaagcctta tttcaggaag ttttttaactg t ttgctatag | 1200 |

```
atgtatgtca tgatagcatc gtaataaaaa tactctaaaa ggagcgagtt t aaatatgca    1260 aaatgtaaaa gaattaagta cgaaagagat gaaacaaatt atcggtggag a aaatgatca    1320 cagaatgcct aatgagttaa atagacctaa caacttatct aaaggtggag c aaaatgtgg    1380 tgctgcaatt gctgggggat tatttggaat cccaaaagga ccactagcat g ggctgctgg    1440 gttagcaaat gtatactcta aatgcaacta aaaagaaga gaaaaaactc a ttacgagtt    1500 ttttctcttc ttttttttgca tgaaattagg aataactaat aaaacaatag c aatcaatag    1560 taaaatctta cttaatatag tttcggaaaa ataaataat cctaaattta t aattactgc    1620 taaaaaaatg cataaattat actctaaatt attttttttt aaattcataa t ataaacatc    1680 ctctctttaa ttagtctacc attccgaaat atttcatccc cagctctttt t ttactaata    1740 taccaactac atttaataac aaaataacta gtaaacttaa tattttagt g gcatagaat    1800 attcaaaaat aaataaaggc accatacatg tagctatcaa tataaataca g aacttacgt    1860 attttattat tttacggaac attataacct attacaactc cgcaaatagc c atagcccat    1920 accatagata agattttac cagcaccacc accacatgt tgttttatct c tttcatact    1980 taatttttt acattttgca tgtctctaca tgctcctttt aaagttttt t agaacctca    2040 cgactataac atggataatt taatcgtggt caaaaacttc ctgaaatagg g tgtttcata    2100 tcctgaacac gaattttag tcaattttcg aaaaatgaaa ctttaaaatt t ctttgacca    2160 gaactctatt tattcttgtg ttgttccttc gaataggttc ccgtatatct t ttttatttg    2220 aagctt                                                                2226

<210> SEQ ID NO 36
<211> LENGTH: 215
<212> TYPE: DNA
<213> ORGANISM: Enterocin 900 peptide;
<220> FEATURE:
<221> NAME/KEY: CDS
<222> LOCATION: (1)..(213)
<223> OTHER INFORMATION:
<221> NAME/KEY: sig_peptide
<222> LOCATION: (1)..(54)
<223> OTHER INFORMATION:

<400> SEQUENCE: 36 atg caa aat gta aaa gaa tta agt acg aaa g ag atg aaa caa att atc      48
Met Gln Asn Val Lys Glu Leu Ser Thr Lys G lu Met Lys Gln Ile Ile
1               5                  10                  15 ggt gga gaa aat gat cac aga atg cct aat g ag tta aat aga cct aac      96
Gly Gly Glu Asn Asp His Arg Met Pro Asn G lu Leu Asn Arg Pro Asn
            20                  25                  30 aac tta tct aaa ggt gga gca aaa tgt ggt g ct gca att gct ggg gga     144
Asn Leu Ser Lys Gly Gly Ala Lys Cys Gly A la Ala Ile Ala Gly Gly
        35                  40                  45 tta ttt gga atc cca aaa gga cca cta gca t gg gct gct ggg tta gca     192
Leu Phe Gly Ile Pro Lys Gly Pro Leu Ala T rp Ala Ala Gly Leu Ala
    50                  55                  60 aat gta tac tct aaa tgc aac ta                                       215
Asn Val Tyr Ser Lys Cys Asn
65                  70

<210> SEQ ID NO 37
<211> LENGTH: 71
<212> TYPE: PRT
<213> ORGANISM: Enterocin 900 peptide;

<400> SEQUENCE: 37
```

```
Met Gln Asn Val Lys Glu Leu Ser Thr Lys G lu Met Lys Gln Ile Ile
1               5                   10                  15

Gly Gly Glu Asn Asp His Arg Met Pro Asn G lu Leu Asn Arg Pro Asn
                20                  25                  30

Asn Leu Ser Lys Gly Gly Ala Lys Cys Gly A la Ala Ile Ala Gly Gly
            35                  40                  45

Leu Phe Gly Ile Pro Lys Gly Pro Leu Ala T rp Ala Ala Gly Leu Ala
        50                  55                  60

Asn Val Tyr Ser Lys Cys Asn
65                  70

<210> SEQ ID NO 38
<211> LENGTH: 71
<212> TYPE: PRT
<213> ORGANISM: Enterocin 900 peptide

<400> SEQUENCE: 38

Met Gln Asn Val Lys Glu Leu Ser Thr Lys G lu Met Lys Gln Ile Ile
1               5                   10                  15

Gly Gly Glu Asn Asp His Arg Met Pro Asn G lu Leu Asn Arg Pro Asn
                20                  25                  30

Asn Leu Ser Lys Gly Gly Ala Lys Cys Gly A la Ala Ile Ala Gly Gly
            35                  40                  45

Leu Phe Gly Ile Pro Lys Gly Pro Leu Ala T rp Ala Ala Gly Leu Ala
        50                  55                  60

Asn Val Tyr Ser Lys Cys Asn
65                  70

<210> SEQ ID NO 39
<211> LENGTH: 103
<212> TYPE: PRT
<213> ORGANISM: Colicin V pre-peptide;
<220> FEATURE:
<221> NAME/KEY: DISULFID
<222> LOCATION: (91)..(102)
<223> OTHER INFORMATION:
<221> NAME/KEY: cleavage_site
<222> LOCATION: (15)..(16)
<223> OTHER INFORMATION:

<400> SEQUENCE: 39

Met Arg Thr Leu Thr Leu Asn Glu Leu Asp S er Val Ser Gly Gly Ala
1               5                   10                  15

Ser Gly Arg Asp Ile Ala Met Ala Ile Gly T hr Leu Ser Gly Gln Phe
                20                  25                  30

Val Ala Gly Gly Ile Gly Ala Ala Ala Gly G ly Val Ala Gly Gly Ala
            35                  40                  45

Ile Tyr Asp Tyr Ala Ser Thr His Lys Pro A sn Pro Ala Met Ser Pro
        50                  55                  60

Ser Gly Leu Gly Gly Thr Ile Lys Gln Lys P ro Glu Gly Ile Pro Ser
65                  70                  75                  80

Glu Ala Trp Asn Tyr Ala Ala Gly Arg Leu C ys Asn Trp Ser Pro Asn
                85                  90                  95

Asn Leu Ser Asp Val Cys Leu
            100

<210> SEQ ID NO 40
<211> LENGTH: 88
<212> TYPE: PRT
```

```
-continued

<213> ORGANISM: Colicin V;
<220> FEATURE:
<221> NAME/KEY: DISULFID
<222> LOCATION: (76)..(87)
<223> OTHER INFORMATION:

<400> SEQUENCE: 40

Ala Ser Gly Arg Asp Ile Ala Met Ala Ile G ly Thr Leu Ser Gly Gln
1               5                   10                  15

Phe Val Ala Gly Gly Ile Gly Ala Ala G ly Gly Val Ala Gly Gly
                20                  25                  30

Ala Ile Tyr Asp Tyr Ala Ser Thr His Lys P ro Asn Pro Ala Met Ser
            35                  40                  45

Pro Ser Gly Leu Gly Gly Thr Ile Lys Gln L ys Pro Glu Gly Ile Pro
        50                  55                      60

Ser Glu Ala Trp Asn Tyr Ala Ala Gly Arg L eu Cys Asn Trp Ser Pro
65              70                  75                      80

Asn Asn Leu Ser Asp Val Cys Leu
                85

<210> SEQ ID NO 41
<211> LENGTH: 675
<212> TYPE: DNA
<213> ORGANISM: carnobacteriocin BM1;
<220> FEATURE:
<221> NAME/KEY: RBS
<222> LOCATION: (89)..(93)
<223> OTHER INFORMATION:
<221> NAME/KEY: CDS
<222> LOCATION: (103)..(285)
<223> OTHER INFORMATION:
<221> NAME/KEY: sig_peptide
<222> LOCATION: (103)..(150)
<223> OTHER INFORMATION:
<221> NAME/KEY: CDS
<222> LOCATION: (303)..(566)
<223> OTHER INFORMATION:

<400> SEQUENCE: 41
tcgagatacg tttatccatg gttcaggatg attttatcaa cgagttaatt a tttatgcta         60 cagtaaactt gttactaaat actttataag gagtgtatgt ac atg aa a agc gtt           114
                                              Met Lys Ser Val
                                                 1 aaa gaa cta aat aaa aaa gaa atg caa caa a tt aat ggt gga gct atc          162
Lys Glu Leu Asn Lys Lys Glu Met Gln Gln I le Asn Gly Gly Ala Ile
  5               10                  15                  20 tct tat ggc aat ggt gtt tat tgt aac aaa g ag aaa tgt tgg gta aac          210
Ser Tyr Gly Asn Gly Val Tyr Cys Asn Lys G lu Lys Cys Trp Val Asn
            25                  30                  35 aag gca gaa aac aaa caa gct att act gga a ta gtt atc ggt gga tgg          258
Lys Ala Glu Asn Lys Gln Ala Ile Thr Gly I le Val Ile Gly Gly Trp
        40                  45                      50 gct tct agt tta gca gga atg gga cat taaagagg ta tctagtt atg ata          308
Ala Ser Ser Leu Ala Gly Met Gly His                      Met Ile
                55                  60 aaa gat gaa aaa ata aat aaa atc tat gct t ta gtt aag agc gca ctt          356
Lys Asp Glu Lys Ile Asn Lys Ile Tyr Ala L eu Val Lys Ser Ala Leu
        65                  70                  75 gat aat acg gat gtt aag aat gat aaa aaa c tt tct tta ctt ctt atg          404
Asp Asn Thr Asp Val Lys Asn Asp Lys Lys L eu Ser Leu Leu Leu Met
80                  85                  90                  95 aga ata caa gaa aca tca att aat gga gaa c ta ttt tac gat tat aaa          452
Arg Ile Gln Glu Thr Ser Ile Asn Gly Glu L eu Phe Tyr Asp Tyr Lys
```

```
                    100              105              110
aaa gaa tta cag cca gct att agt atg tac t ct att caa cat aac ttt       500
Lys Glu Leu Gln Pro Ala Ile Ser Met Tyr S er Ile Gln His Asn Phe
            115              120              125 cgg gtt cct gac gat cta gta aaa ctg tta g ca tta gtt caa aca cct       548
Arg Val Pro Asp Asp Leu Val Lys Leu Leu A la Leu Val Gln Thr Pro
            130              135              140 aaa gct tgg tca ggg ttt taactttagt tccagatgag t taaaatcct              596
Lys Ala Trp Ser Gly Phe
            145 taaaaataag gaataatggt aaatcagcat tccttatttt tatagtcatc a cactataac     656 tttacttaaa gatgttcga                                                   675

<210> SEQ ID NO 42
<211> LENGTH: 61
<212> TYPE: PRT
<213> ORGANISM: carnobacteriocin BM1;

<400> SEQUENCE: 42

Met Lys Ser Val Lys Glu Leu Asn Lys Lys G lu Met Gln Gln Ile Asn
1               5                  10                   15

Gly Gly Ala Ile Ser Tyr Gly Asn Gly Val T yr Cys Asn Lys Glu Lys
            20                  25                   30

Cys Trp Val Asn Lys Ala Glu Asn Lys Gln A la Ile Thr Gly Ile Val
        35                  40                   45

Ile Gly Gly Trp Ala Ser Ser Leu Ala Gly M et Gly His
    50                  55                   60

<210> SEQ ID NO 43
<211> LENGTH: 88
<212> TYPE: PRT
<213> ORGANISM: carnobacteriocin BM1;

<400> SEQUENCE: 43

Met Ile Lys Asp Glu Lys Ile Asn Lys Ile T yr Ala Leu Val Lys Ser
1               5                  10                   15

Ala Leu Asp Asn Thr Asp Val Lys Asn Asp L ys Lys Leu Ser Leu Leu
            20                  25                   30

Leu Met Arg Ile Gln Glu Thr Ser Ile Asn G ly Glu Leu Phe Tyr Asp
        35                  40                   45

Tyr Lys Lys Glu Leu Gln Pro Ala Ile Ser M et Tyr Ser Ile Gln His
    50                  55                   60

Asn Phe Arg Val Pro Asp Asp Leu Val Lys L eu Leu Ala Leu Val Gln
65                  70                   75                   80

Thr Pro Lys Ala Trp Ser Gly Phe
                85

<210> SEQ ID NO 44
<211> LENGTH: 61
<212> TYPE: PRT
<213> ORGANISM: Carnobacterium B2

<400> SEQUENCE: 44

Met Lys Ser Val Lys Glu Leu Asn Lys Lys G lu Met Gln Gln Ile Asn
1               5                  10                   15

Gly Gly Ala Ile Ser Tyr Gly Asn Gly Val T yr Cys Asn Lys Glu Lys
            20                  25                   30

Cys Trp Val Asn Lys Ala Glu Asn Lys Gln A la Ile Thr Gly Ile Val
```

```
                    35                  40                  45
Ile Gly Gly Trp Ala Ser Ser Leu Ala Gly M et Gly His
         50                  55                  60

<210> SEQ ID NO 45
<211> LENGTH: 88
<212> TYPE: PRT
<213> ORGANISM: Carnobacterium B2

<400> SEQUENCE: 45

Met Ile Lys Asp Glu Lys Ile Asn Lys Ile T yr Ala Leu Val Lys Ser
1               5                  10                  15

Ala Leu Asp Asn Thr Asp Val Lys Asn Asp L ys Lys Leu Ser Leu Leu
            20                  25                  30

Leu Met Arg Ile Gln Glu Thr Ser Ile Asn G ly Glu Leu Phe Tyr Asp
        35                  40                  45

Tyr Lys Lys Glu Leu Gln Pro Ala Ile Ser M et Tyr Ser Ile Gln His
    50                  55                  60

Asn Phe Arg Val Pro Asp Asp Leu Val Lys L eu Leu Ala Leu Val Gln
65                  70                  75                  80

Thr Pro Lys Ala Trp Ser Gly Phe
                85

<210> SEQ ID NO 46
<211> LENGTH: 1907
<212> TYPE: DNA
<213> ORGANISM: carnobacterium B2 operon;
<220> FEATURE:
<221> NAME/KEY: -35_signal
<222> LOCATION: (165)..(170)
<223> OTHER INFORMATION:
<221> NAME/KEY: -10_signal
<222> LOCATION: (189)..(193)
<223> OTHER INFORMATION:
<221> NAME/KEY: RBS
<222> LOCATION: (221)..(225)
<223> OTHER INFORMATION:
<221> NAME/KEY: CDS
<222> LOCATION: (236)..(433)
<223> OTHER INFORMATION:
<221> NAME/KEY: RBS
<222> LOCATION: (460)..(465)
<223> OTHER INFORMATION:
<221> NAME/KEY: CDS
<222> LOCATION: (473)..(805)
<223> OTHER INFORMATION:
<221> NAME/KEY: CDS
<222> LOCATION: (1025)..(1267)
<223> OTHER INFORMATION:

<400> SEQUENCE: 46
aagcttttat agtacaatta tttatgcgtg ctatgcaata gctattgtat a tactatttt     60 tactatgaga aaagattctt atgaaaataa caaaaataat cgtaaaaaag t tatatagca    120 tttatttcat ttatgaattc aaatacccctg gttcaagatg tatttttccaa a aaaatgttc    180 agatatgata tagtttttttt gaaatacaaa tataaaataa aggagtttga t ttag atg    238
                                                              Met
                                                               1 aat agc gta aaa gaa tta aac gtg aaa gaa a tg aaa caa tta cac ggt       286
Asn Ser Val Lys Glu Leu Asn Val Lys Glu M et Lys Gln Leu His Gly
         5                  10                  15 gga gta aat tat ggt aat ggt gtt tct tgc a gt aaa aca aaa tgt tca       334
Gly Val Asn Tyr Gly Asn Gly Val Ser Cys S er Lys Thr Lys Cys Ser
        20                  25                  30
```

```
gtt aac tgg gga caa gcc ttt caa gaa aga t ac aca gct gga att aac        382
Val Asn Trp Gly Gln Ala Phe Gln Glu Arg T yr Thr Ala Gly Ile Asn
     35                  40                  45 tca ttt gta agt gga gtc gct tct ggg gca g ga tcc att ggt agg aga        430
Ser Phe Val Ser Gly Val Ala Ser Gly Ala G ly Ser Ile Gly Arg Arg
 50                  55                  60                  65 ccg taaatatata aatacaatat agagcaaggt ggtgataca atg ga t ata aag          484
Pro                                                 Met Asp Ile Lys
                                                             70 tct caa aca tta tat ttg aat cta agc gag g ca tat aaa gac cct gaa        532
Ser Gln Thr Leu Tyr Leu Asn Leu Ser Glu A la Tyr Lys Asp Pro Glu
                 75                  80                  85 gta aaa gct aat gaa ttc tta tca aaa tta g tt gta caa tgt gct ggg        580
Val Lys Ala Asn Glu Phe Leu Ser Lys Leu V al Val Gln Cys Ala Gly
             90                  95                 100 aaa tta aca gct tca aac agt gag aac agt t at att gaa gta ata tca       628
Lys Leu Thr Ala Ser Asn Ser Glu Asn Ser T yr Ile Glu Val Ile Ser
            105                 110                 115 ttg cta tct agg ggt att tct agt tat tat t ta tcc cat aaa cgt ata       676
Leu Leu Ser Arg Gly Ile Ser Ser Tyr Tyr L eu Ser His Lys Arg Ile
        120                 125                 130 att cct tca agt atg tta act ata tat act c aa ata caa aag gat ata       724
Ile Pro Ser Ser Met Leu Thr Ile Tyr Thr G ln Ile Gln Lys Asp Ile
135                 140                 145                 150 aaa aac ggg aat att gac acc gaa aaa tta a gg aaa tat gag ata gca       772
Lys Asn Gly Asn Ile Asp Thr Glu Lys Leu A rg Lys Tyr Glu Ile Ala
                155                 160                 165 aaa gga tta atg tcc gtt cct tat ata tat t tc taattttttc aatgatgtta    825
Lys Gly Leu Met Ser Val Pro Tyr Ile Tyr P he
            170                 175 gttgacttca aaagatgtg aaatcgatta gcattttcaa aattagatta a aaatactat     885 ctatataaaa tagaactact gatttaaagt atttataaga atataaagta g caaataaca    945 tgatagacac aattaaggag cgacattta tggaaaattt gaaatggtat t cgggcggga     1005 acgatagaaa aaaaagca atg gct act att act gat tt g tta aac gat tta     1057
                     Met Ala Thr Ile Thr Asp Leu Leu Asn  Asp Leu
                                 180                 185 aaa ata gac tta ggt aac gaa tct cta caa a at gtc tta gaa aat tat     1105
Lys Ile Asp Leu Gly Asn Glu Ser Leu Gln A sn Val Leu Glu Asn Tyr
        190                 195                 200 ctt gaa gaa ttg gaa caa gca aat gct gct g tt cca att ata tta ggc     1153
Leu Glu Glu Leu Glu Gln Ala Asn Ala Ala V al Pro Ile Ile Leu Gly
205                 210                 215                 220 cgt atg aac ata gat atc tct aca gca atc a ga aaa gat ggt gtt act     1201
Arg Met Asn Ile Asp Ile Ser Thr Ala Ile A rg Lys Asp Gly Val Thr
                225                 230                 235 tta tca gaa att cag tct aaa aaa tta aaa g ag ctg att tca ata tcc     1249
Leu Ser Glu Ile Gln Ser Lys Lys Leu Lys G lu Leu Ile Ser Ile Ser
            240                 245                 250 tat att aaa tat ggc tat taatttagta ttaataacag t gtaggattg            1297
Tyr Ile Lys Tyr Gly Tyr
            255 attcaaatta tttgaatcaa aatttatata caaattttat ttattttggg t ctttaaata   1357 attttgtgta agttcaaatt atttaaagat gagttaaaac tctatcttcg a aaaacatca   1417 caaaatgtga tgaaatttgt ccccaattttt ggaccttcat ggtccatttt t tcgttacat  1477 ccatcgtcac taaacaaagc attttagta aggattcatc agatgggaat a ctaccttag   1537 attttgttgg ctttcacagc tgacaatgga ggccttcaat cacattggcg g tataaataa   1597
```

-continued

```
tccggcgcaa atctgctgaa tacttgaaaa atgtcgctaa ttctgcccag t tatctatca    1657 attcttcaat taatttgtct gcgtttatat ccattttcat tcccttttt t aattttca     1717 tttttagtt actttaaacg gtttaaagcc ttaagcactt aggctttaat c tttttcac    1777 ttgatctaat tatttgaact tcagcattta tcttttgatt tattcttta g ggaattgac   1837 cgaataggga gatttcctgt gagtaggcgc caacggtggt ggcggtcgga g tcagccgac  1897 tcacaagctt                                                          1907
```

<210> SEQ ID NO 47
<211> LENGTH: 66
<212> TYPE: PRT
<213> ORGANISM: carnobacterium B2 operon;

<400> SEQUENCE: 47

Met Asn Ser Val Lys Glu Leu Asn Val Lys Glu Met Lys Gln Leu His
1               5                   10                  15

Gly Gly Val Asn Tyr Gly Asn Gly Val Ser Cys Ser Lys Thr Lys Cys
            20                  25                  30

Ser Val Asn Trp Gly Gln Ala Phe Gln Glu Arg Tyr Thr Ala Gly Ile
        35                  40                  45

Asn Ser Phe Val Ser Gly Val Ala Ser Gly Ala Gly Ser Ile Gly Arg
    50                  55                  60

Arg Pro
65

<210> SEQ ID NO 48
<211> LENGTH: 111
<212> TYPE: PRT
<213> ORGANISM: carnobacterium B2 operon;

<400> SEQUENCE: 48

Met Asp Ile Lys Ser Gln Thr Leu Tyr Leu Asn Leu Ser Glu Ala Tyr
1               5                   10                  15

Lys Asp Pro Glu Val Lys Ala Asn Glu Phe Leu Ser Lys Leu Val Val
            20                  25                  30

Gln Cys Ala Gly Lys Leu Thr Ala Ser Asn Ser Glu Asn Ser Tyr Ile
        35                  40                  45

Glu Val Ile Ser Leu Leu Ser Arg Gly Ile Ser Ser Tyr Tyr Leu Ser
    50                  55                  60

His Lys Arg Ile Ile Pro Ser Ser Met Leu Thr Ile Tyr Thr Gln Ile
65                  70                  75                  80

Gln Lys Asp Ile Lys Asn Gly Asn Ile Asp Thr Glu Lys Leu Arg Lys
            85                  90                  95

Tyr Glu Ile Ala Lys Gly Leu Met Ser Val Pro Tyr Ile Tyr Phe
            100                 105                 110

<210> SEQ ID NO 49
<211> LENGTH: 81
<212> TYPE: PRT
<213> ORGANISM: carnobacterium B2 operon;

<400> SEQUENCE: 49

Met Ala Thr Ile Thr Asp Leu Leu Asn Asp Leu Lys Ile Asp Leu Gly
1               5                   10                  15

Asn Glu Ser Leu Gln Asn Val Leu Glu Asn Tyr Leu Glu Glu Leu Glu
            20                  25                  30

```
Gln Ala Asn Ala Ala Val Pro Ile Ile Leu Gly Arg Met Asn Ile Asp
            35                  40                  45

Ile Ser Thr Ala Ile Arg Lys Asp Gly Val Thr Leu Ser Glu Ile Gln
 50                  55                  60

Ser Lys Lys Leu Lys Glu Leu Ile Ser Ile Ser Tyr Ile Lys Tyr Gly
 65                  70                  75                  80

Tyr

<210> SEQ ID NO 50
<211> LENGTH: 66
<212> TYPE: PRT
<213> ORGANISM: Carnobacterium B2 operon

<400> SEQUENCE: 50

Met Asn Ser Val Lys Glu Leu Asn Val Lys Glu Met Lys Gln Leu His
 1               5                  10                  15

Gly Gly Val Asn Tyr Gly Asn Gly Val Ser Cys Ser Lys Thr Lys Cys
            20                  25                  30

Ser Val Asn Trp Gly Gln Ala Phe Gln Glu Arg Tyr Thr Ala Gly Ile
            35                  40                  45

Asn Ser Phe Val Ser Gly Val Ala Ser Gly Ala Gly Ser Ile Gly Arg
        50                  55                  60

Arg Pro
 65

<210> SEQ ID NO 51
<211> LENGTH: 111
<212> TYPE: PRT
<213> ORGANISM: Carnobacterium B2 operon

<400> SEQUENCE: 51

Met Asp Ile Lys Ser Gln Thr Leu Tyr Leu Asn Leu Ser Glu Ala Tyr
 1               5                  10                  15

Lys Asp Pro Glu Val Lys Ala Asn Glu Phe Leu Ser Lys Leu Val Val
            20                  25                  30

Gln Cys Ala Gly Lys Leu Thr Ala Ser Asn Ser Glu Asn Ser Tyr Ile
            35                  40                  45

Glu Val Ile Ser Leu Leu Ser Arg Gly Ile Ser Ser Tyr Tyr Leu Ser
        50                  55                  60

His Lys Arg Ile Ile Pro Ser Ser Met Leu Thr Ile Tyr Thr Gln Ile
 65                  70                  75                  80

Gln Lys Asp Ile Lys Asn Gly Asn Ile Asp Thr Glu Lys Leu Arg Lys
            85                  90                  95

Tyr Glu Ile Ala Lys Gly Leu Met Ser Val Pro Tyr Ile Tyr Phe
            100                 105                 110

<210> SEQ ID NO 52
<211> LENGTH: 81
<212> TYPE: PRT
<213> ORGANISM: Carnobacterium B2 operon

<400> SEQUENCE: 52

Met Ala Thr Ile Thr Asp Leu Leu Asn Asp Leu Lys Ile Asp Leu Gly
 1               5                  10                  15

Asn Glu Ser Leu Gln Asn Val Leu Glu Asn Tyr Leu Glu Glu Leu Glu
            20                  25                  30

Gln Ala Asn Ala Ala Val Pro Ile Ile Leu Gly Arg Met Asn Ile Asp
            35                  40                  45
```

-continued

```
Ile Ser Thr Ala Ile Arg Lys Asp Gly Val Thr Leu Ser Glu Ile Gln
    50                  55                  60
Ser Lys Lys Leu Lys Glu Leu Ile Ser Ile Ser Tyr Ile Lys Tyr Gly
65                  70                  75                  80
Tyr
```

```
<210> SEQ ID NO 53
<211> LENGTH: 35
<212> TYPE: DNA
<213> ORGANISM: JMc7;

<400> SEQUENCE: 53
cccaagcttc tgctgtaaat tatggtaatg gtgtt                                    35

<210> SEQ ID NO 54
<211> LENGTH: 36
<212> TYPE: DNA
<213> ORGANISM: KLR179;

<400> SEQUENCE: 54
gcgcaagctt ctgctcggac accagaaatg cctgtt                                   36

<210> SEQ ID NO 55
<211> LENGTH: 30
<212> TYPE: DNA
<213> ORGANISM: KLR180;

<400> SEQUENCE: 55
ggccaagctt gccattaagt ctggttgcta                                          30

<210> SEQ ID NO 56
<211> LENGTH: 20
<212> TYPE: DNA
<213> ORGANISM: MB32;

<400> SEQUENCE: 56
aattcgagct cgcccaaatc                                                     20

<210> SEQ ID NO 57
<211> LENGTH: 40
<212> TYPE: DNA
<213> ORGANISM: MB37;

<400> SEQUENCE: 57
tgagtaattt tcggtgcagc acctcctacg acttgttcga                               40

<210> SEQ ID NO 58
<211> LENGTH: 23
<212> TYPE: DNA
<213> ORGANISM: RW58;

<400> SEQUENCE: 58
tacgcgcaag aacagacaaa atc                                                 23

<210> SEQ ID NO 59
<211> LENGTH: 40
<212> TYPE: DNA
<213> ORGANISM: MB38;

<400> SEQUENCE: 59
tgagtaattt tcggtgcagc tcctccgtta gcttctgaaa                               40
```

```
<210> SEQ ID NO 60
<211> LENGTH: 19
<212> TYPE: DNA
<213> ORGANISM: MB39;

<400> SEQUENCE: 60
tacgaattcg agctcgccc                                                 19

<210> SEQ ID NO 61
<211> LENGTH: 76
<212> TYPE: DNA
<213> ORGANISM: MB42;

<400> SEQUENCE: 61
attttcggtg cagcacctcc agaaacagaa tctaattcat ttagagtcag a gttctcata    60 ataactttcc tctttt                                                    76

<210> SEQ ID NO 62
<211> LENGTH: 40
<212> TYPE: DNA
<213> ORGANISM: MB41;

<400> SEQUENCE: 62
tgagtaattt tcggtgcagc cataataact ttcctctttt                          40

<210> SEQ ID NO 63
<211> LENGTH: 37
<212> TYPE: DNA
<213> ORGANISM: MB43;

<400> SEQUENCE: 63
atatcacgcc ctgaagcacc tcctacgact tgttcga                             37

<210> SEQ ID NO 64
<211> LENGTH: 36
<212> TYPE: DNA
<213> ORGANISM: MB44;
<220> FEATURE:
<221> NAME/KEY: misc_difference
<222> LOCATION: (11)..(12)
<223> OTHER INFORMATION: standard_name= "any base"
<221> NAME/KEY: misc_difference
<222> LOCATION: (16)..(17)
<223> OTHER INFORMATION: standard_name= "any base"

<400> SEQUENCE: 64
aattaagctt ggatccttct gtgtggattg tccaat                              36

<210> SEQ ID NO 65
<211> LENGTH: 21
<212> TYPE: DNA
<213> ORGANISM: APO-1
<220> FEATURE:
<221> NAME/KEY: misc_difference
<222> LOCATION: (11)..(12)
<223> OTHER INFORMATION: standard_name="(any base)"
<221> NAME/KEY: misc_difference
<222> LOCATION: (16)..(17)
<223> OTHER INFORMATION: standard_name="(any base)"

<400> SEQUENCE: 65
aaagatattg gaaaggattg g                                              21

<210> SEQ ID NO 66
<211> LENGTH: 7
```

```
<212> TYPE: PRT
<213> ORGANISM: Carnobacterium sp.

<400> SEQUENCE: 66

Val Asn Tyr Gly Asn Gly Val
1               5

<210> SEQ ID NO 67
<211> LENGTH: 32
<212> TYPE: PRT
<213> ORGANISM: CF01 probe
<220> FEATURE:
<221> NAME/KEY: MISC_FEATURE
<222> LOCATION: (13)..(13)
<223> OTHER INFORMATION: C or A
<221> NAME/KEY: MISC_FEATURE
<222> LOCATION: (15)..(15)
<223> OTHER INFORMATION: T or A
<221> NAME/KEY: MISC_FEATURE
<222> LOCATION: (21)..(21)
<223> OTHER INFORMATION: T or A
<221> NAME/KEY: MISC_FEATURE
<222> LOCATION: (30)..(30)
<223> OTHER INFORMATION: T or A

<400> SEQUENCE: 67

Gly Ala Ala Ala Ala Thr Gly Ala Thr Cys Ala Thr Xaa Gly Xaa Ala
1               5                   10                  15

Thr Gly Cys Cys Xaa Ala Ala Thr Gly Ala Ala Cys Thr Xaa Ala Ala
                20                  25                  30

<210> SEQ ID NO 68
<211> LENGTH: 61
<212> TYPE: PRT
<213> ORGANISM: Leucocin A

<400> SEQUENCE: 68

Met Met Asn Met Lys Pro Thr Glu Ser Tyr Glu Gln Leu Asp Asn Ser
1               5                   10                  15

Ala Leu Glu Gln Val Val Gly Gly Lys Tyr Tyr Gly Asn Gly Val His
                20                  25                  30

Cys Thr Lys Ser Gly Cys Ser Val Asn Trp Gly Glu Ala Glu Ser Ala
        35                  40                  45

Gly Val His Arg Leu Ala Asn Gly Gly Asn Gly Phe Trp
    50                  55                  60

<210> SEQ ID NO 69
<211> LENGTH: 36
<212> TYPE: PRT
<213> ORGANISM: Mesenteriocin Y105

<400> SEQUENCE: 69

Lys Tyr Tyr Gly Asn Gly Val His Cys Thr Lys Ser Gly Cys Ser Val
1               5                   10                  15

Asn Trp Gly Glu Ala Ala Ser Ala Gly Ile His Arg Leu Ala Asn Gly
                20                  25                  30

Gly Asn Gly Phe
        35

<210> SEQ ID NO 70
<211> LENGTH: 41
<212> TYPE: PRT
<213> ORGANISM: Sakacin P
<220> FEATURE:
<221> NAME/KEY: MISC_FEATURE
```

```
<222> LOCATION: (33)..(33)
<223> OTHER INFORMATION: any amino acid
<221> NAME/KEY: MISC_FEATURE
<222> LOCATION: (37)..(37)
<223> OTHER INFORMATION: any amino acid
<221> NAME/KEY: MISC_FEATURE
<222> LOCATION: (40)..(40)
<223> OTHER INFORMATION: any amino acid
<221> NAME/KEY: MISC_FEATURE
<222> LOCATION: (41)..(41)
<223> OTHER INFORMATION: any amino acid

<400> SEQUENCE: 70

Lys Tyr Tyr Gly Asn Gly Val His Cys Gly Lys His Ser Cys Thr Val
 1               5                  10                  15

Asp Trp Gly Thr Ala Ile Gly Asn Ile Gly Asn Asn Ala Ala Ala Asn
            20                  25                  30

Xaa Ala Thr Gly Xaa Asn Ala Xaa Xaa
        35                  40

<210> SEQ ID NO 71
<211> LENGTH: 62
<212> TYPE: PRT
<213> ORGANISM: Pediocin PA1

<400> SEQUENCE: 71

Met Lys Lys Ile Glu Lys Leu Thr Glu Lys Glu Met Ala Asn Ile Ile
 1               5                  10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Asn His Lys Cys
    50                  55                  60

<210> SEQ ID NO 72
<211> LENGTH: 66
<212> TYPE: PRT
<213> ORGANISM: Carnobacteriocin B2

<400> SEQUENCE: 72

Met Asn Ser Val Lys Glu Leu Asn Val Lys Glu Met Lys Gln Leu His
 1               5                  10                  15

Gly Gly Val Asn Tyr Gly Asn Gly Val Ser Cys Ser Lys Thr Lys Cys
            20                  25                  30

Ser Val Asn Trp Gly Gln Ala Phe Gln Glu Arg Tyr Thr Ala Gly Ile
        35                  40                  45

Asn Ser Phe Val Ser Gly Val Ala Ser Gly Ala Gly Ser Ile Gly Arg
    50                  55                  60

Arg Pro
65

<210> SEQ ID NO 73
<211> LENGTH: 61
<212> TYPE: PRT
<213> ORGANISM: Carnobacteriocin BM1

<400> SEQUENCE: 73

Met Lys Ser Val Lys Glu Leu Asn Lys Lys Glu Met Gln Gln Ile Ile
 1               5                  10                  15

Gly Gly Ala Ile Ser Tyr Gly Asn Gly Val Tyr Cys Asn Lys Glu Lys
            20                  25                  30
```

```
Cys Trp Val Asn Lys Ala Glu Asn Lys Gln Ala Ile Thr Gly Ile Val
         35                  40                  45

Ile Gly Gly Trp Ala Ser Ser Leu Ala Gly Met Gly His
         50                  55                  60

<210> SEQ ID NO 74
<211> LENGTH: 59
<212> TYPE: PRT
<213> ORGANISM: Sakacin A

<400> SEQUENCE: 74

Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
            20                  25                  30

Cys Trp Val Asn Arg Gly Glu Ala Thr Gln Ser Ile Ile Gly Gly Met
         35                  40                  45

Ile Ser Gly Trp Ala Ser Gly Leu Ala Gly Met
         50                  55

<210> SEQ ID NO 75
<211> LENGTH: 31
<212> TYPE: PRT
<213> ORGANISM: Curvacin A
<220> FEATURE:
<221> NAME/KEY: MISC_FEATURE
<222> LOCATION: (25)..(25)
<223> OTHER INFORMATION: any amino acid
<221> NAME/KEY: MISC_FEATURE
<222> LOCATION: (26)..(26)
<223> OTHER INFORMATION: any amino acid
<221> NAME/KEY: MISC_FEATURE
<222> LOCATION: (28)..(28)
<223> OTHER INFORMATION: any amino acid
<221> NAME/KEY: MISC_FEATURE
<222> LOCATION: (29)..(29)
<223> OTHER INFORMATION: any amino acid
<221> NAME/KEY: MISC_FEATURE
<222> LOCATION: (31)..(31)
<223> OTHER INFORMATION: any amino acid

<400> SEQUENCE: 75

Ala Cys Ser Tyr Gly Asn Gly Val Tyr Cys Asn Asn Lys Lys Ser Trp
1               5                   10                  15

Val Asn Gly Gly Glu Ala Thr Gln Xaa Xaa Ile Xaa Xaa Gly Xaa
            20                  25                  30

<210> SEQ ID NO 76
<211> LENGTH: 18
<212> TYPE: PRT
<213> ORGANISM: Carnobacteriocin A

<400> SEQUENCE: 76

Met Asn Asn Val Lys Glu Leu Ser Ile Lys Glu Met Gln Gln Val Thr
1               5                   10                  15

Gly Gly

<210> SEQ ID NO 77
<211> LENGTH: 18
<212> TYPE: PRT
<213> ORGANISM: Lactacin F

<400> SEQUENCE: 77

Met Lys Gln Phe Asn Tyr Leu Ser His Lys Asp Leu Ala Val Val Val
```

-continued

```
1               5              10             15
Gly Gly

<210> SEQ ID NO 78
<211> LENGTH: 21
<212> TYPE: PRT
<213> ORGANISM: Lactococcin B

<400> SEQUENCE: 78

Met Lys Asn Gln Leu Asn Phe Asn Ile Leu S er Glu Glu Asp Leu Ala
1               5                   10              15

Glu Ala Asn Gly Gly
            20

<210> SEQ ID NO 79
<211> LENGTH: 21
<212> TYPE: PRT
<213> ORGANISM: Lactococcin A

<400> SEQUENCE: 79

Met Lys Asn Gln Leu Asn Phe Asn Ile Leu S er Glu Glu Asp Leu Ser
1               5                   10              15

Glu Ala Asn Gly Gly
            20

<210> SEQ ID NO 80
<211> LENGTH: 21
<212> TYPE: PRT
<213> ORGANISM: Lactococcin M

<400> SEQUENCE: 80

Met Lys Asn Gln Leu Asn Phe Glu Ile Leu S er Glu Glu Asp Leu Gln
1               5                   10              15

Gly Ile Asn Gly Gly
            20
```

BACTERIOCINS, TRANSPORT AND VECTOR SYSTEM AND METHOD OF USE THEREOF

This application claims priority from US provisional application No. 60/026,257, filed Sep. 5, 1996, incorporated herein by reference in full.

FIELD OF INVENTION

This invention relates to novel polypeptides, bacteriocins, immunity genes obtained from lactic acid bacteria and a method of use thereof.

BACKGROUND

With the current consumer demand for fresh (i.e., never frozen) foods, it is important that methods be developed for safe storage of these products especially for fresh meats which are manufactured locally but are marketed around the world. The lactic microflora (lactic acid bacteria) of vacuum packaged meats delays spoilage for weeks or months, as opposed to meats packaged under aerobic conditions which develop a putrefactive microflora that causes spoilage within days.

Vacuum packaged meats have an extended but unpredictable storage life dependent on the types of Tactics that dominate the microflora. Meat Tactics can cause severe spoilage problems, such as sulphide odors or greening by some Lactobacillus species and gas or slime production by Leuconostoc species. Other Tactics exert a preservative effect, extending storage life and enhancing meat safety by competitive growth, by producing organic acids, and by producing antagonistic substances known as bacteriocins (peptides or proteins that inhibit the growth of other, usually closely related, bacteria).

Nisin is a bacteriocin produced by lactics used for cheese manufacture, and is the only bacteriocin licensed for use as a food preservative. Nisin is unusual because it is active against a wide range of gram-positive bacteria, including the spores of *Clostridium botulinum*; unfortunately, its producer strain does not grow in chill-stored meats, and nisin does not function in meat systems.

Class II bacteriocins are characterized as small, heat stable, hydrophobic peptides with a high isoelectric point. They are produced as precursors with an N-terminal extension of 18 to 24 amino acids. This extension is cleaved at the C-terminus side of two glycine residues to give the mature bacteriocin. Sequence alignment of the N-termini revealed a remarkable degree of similarity in their hydropathic profiles (Fremaux et al. 1993).

The nucleotide sequences of the structural genes for several class II bacteriocins have been published, including pediocin PA-1/AcH (Bukhtiyarova et al. 1994, Marugg et al. 1992), sakacin A and P (Holck et al. 1989, Tichaczek et al. 1994), lactacin F (Fremaux et al. 1993, Muriana and Klaenhammer 1991), leucocin A (Hastings et al. 1991), lactococcins A, B, and M (Holo et al. 1991; Stoddard et al. 1992; van Belkum et al. 1991; van Belkum et al. 1992), plantaricin A (Diep et al. 1994) and carnobacteriocins A, BM1, and B2 (Quadri et al. 1994; Worobo et al. 1994). However, the additional genes necessary for bacteriocin production have only been determined for the lactococcins and pediocin PA-1/AcH and, in the case of the some of the lactococcins, the gene for immunity has also been confirmed. The genetic characterization of the lactococcin and pediocin gene clusters indicates that they have similar features. They both have genes for bacteriocin production in an operon structure, although the structural and immunity genes for the lactococcins can be transcribed independent of the other genes in the operon. Furthermore, one of the genes in each of the lactococcin and pediocin operons encodes a protein which belongs to the HlyB-family of ATP-binding cassette (ABC) transporters (Higgins 1992). This protein is thought to be involved in the signal sequence-independent secretion of the bacteriocins. Recently, genes encoding proteins which resemble members of a two-component signal transduction system have been identified which are involved in the expression of plantaricin A and sakacin A (Axelsson et al. 1993; Diep et al. 1994).

SUMMARY OF THE INVENTION

One aspect of the invention is a new bacteriocin, brochocin-C: peptide A (SEQ ID NO:23), peptide B (SEQ ID NO:25) and its corresponding immunity peptide (SEQ ID NO:27). Another aspect of the invention is a polynucleotide encoding the brochocin-C operon (SEQ ID NO:21), peptide A (SEQ ID NO:22), peptide B (SEQ ID NO:24), or immunity (SEQ ID NO:26).

Another aspect of the invention is a polynucleotide encoding a new bacteriocin enterocin 900 (SEQ ID NO:28), a polynucleotide encoding the first enterocin 900 peptide (SEQ ID NO:29), and the enterocin 900 peptide (SEQ ID NO:30).

Another aspect of the invention is a method for inhibiting pathogenic bacteria by providing a bacteriocin selected from the group consisting of brochocin-C and enterocin 900, either as a composition or by providing a bacterial source of brochocin-C or enterocin 900. For example, one may inhibit spoilage bacteria in foodstuffs, such as meat, inhibit pathogenic bacteria topically on animals, including humans, and inhibit bacteria infection of fermentation reactors.

Another aspect of the invention is an expression vector for obtaining secretion of proteins from lactics, comprising a promoter functional in the lactic host, a polynucleotide encoding a divergicin signal peptide (SEQ ID NO:19), and a structural gene. Another aspect of the invention is the vector which comprises a plurality of structural genes, each operably linked to a polynucleotide encoding a divergicin signal peptide.

Another aspect of the invention is a method to attach bacteriocin structural and immunity genes to a signal peptide or leader peptide gene so that the bacteriocins can be exported from the host cell.

Another aspect of the invention is a novel food-grade plasmid that can be used as a plasmid vector for genes including, but not limited to, bacteriocins, other polypeptides, enzymes or proteins in organisms for use in food products or as a probiotic.

Another aspect of the invention is a method to preserve food by adding bacteriocin-producing bacteria.

BRIEF DESCRIPTION OF FIGURES

In FIG. 14, the sequence for Leucocin A is Seq. ID No. 55; for Mesenteriocin Y105, Seq. ID No. 56; for Sakacin P, Seq. ID No. 57; for Pediocin PA1, Seq. ID No. 58; for Carnobacterium B2, Seq. ID No. 59; for Carnobacterium BM1, Seq. ID No. 60; for Sakacin A, Seq. ID No. 61; for Curvacin A, Seq. ID No. 62; for Carnobacterium A, Seq. ID No. 63; for Lactacin F, Seq. ID No. 64; for Lactococcin B, Seq. ID No. 65; for Lactococcin A, Seq. ID No. 66; and for Lactococcin M, Seq. ID No. 67.

ABBREVIATIONS

Figure 1:
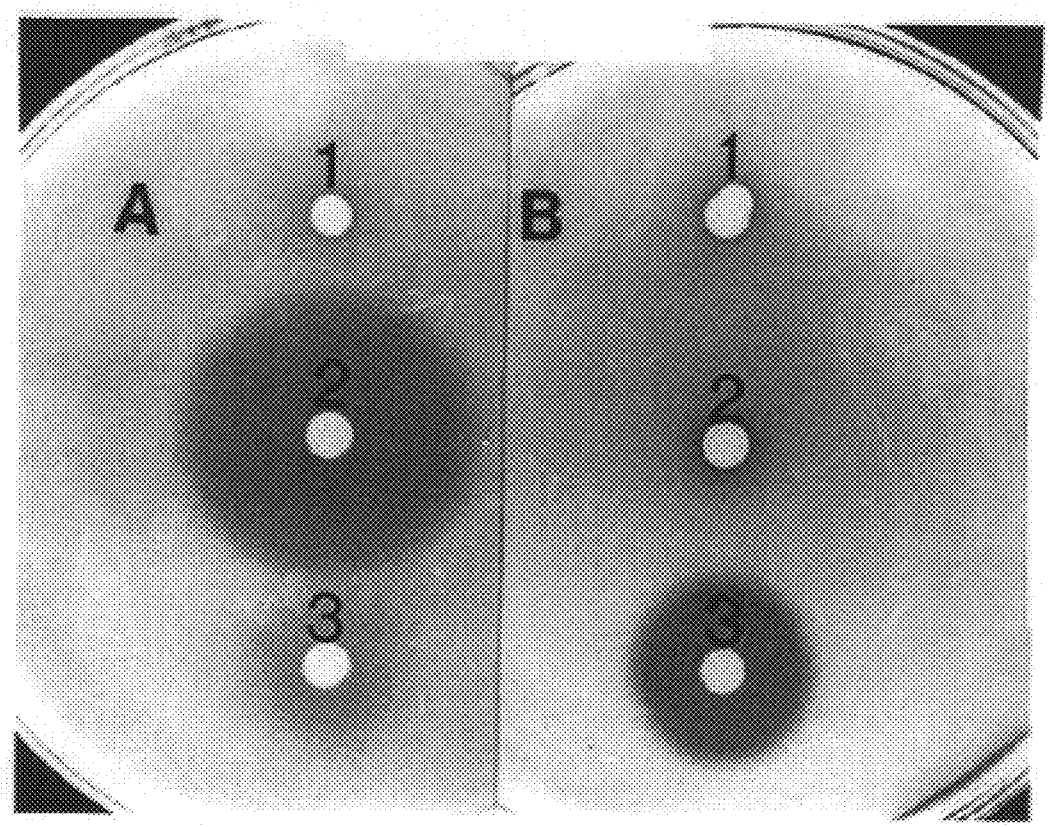
FIG. 1. Deferred inhibition tests against *C. piscicola* LV17C (A) and *C. divergens* LV13 (B) by divergin A and carnobacteriocin B2. 1.*C. piscicola* LV17C containing pMG36e; 2.*C. piscicola* LV17C containing pRW19e; 3. *C. piscicola* LV17C containing pJKM14.

The abbreviations in the nucleotide sequences are cytidine (c); adenosine (a); thymidine (t); guanosine (g); and in amino acid sequences alanine (A); arginine (R); asparagine (N); aspartic acid (D); cysteine (C); glutamine (Q); glutamic acid (E); glycine (G); histidine (H); isoleucine (I); leucine (L); lysine (K); methionine (M); phenylalanine (F); proline (P); serine (S); threonine (T); tryptophan (W); tyrosine (Y) and valine (V).

Other abbreviations used include: carnobacteriocin 26 (cbn 26); carnobacteriocin A (cbnA); carnobacteriocin B (cbnB); Leucocin A (Leu A); Brochocin-C (Broch C)

DETAILED DESCRIPTION

Definitions

The term "gene" used herein refers to a DNA sequence including but not limited to a DNA sequence that can be transcribed into mRNA which can be translated into polypeptide chains, transcribed into rRNA or tRNA or serve as recognition sites for enzymes and other proteins involved in DNA replication, transcription and regulation. These genes include, but are not limited to, structural genes, immunity genes and secretory (transport) genes.

The term "vector" used herein refers to any DNA material capable of transferring genetic material into a host organism. The vector may be linear or circular in topology and includes but is not limited to plasmids, food grade plasmids, DNA bacteriophages or DNA viruses. The vector may include amplification genes, enhancers or selection markers and may or may not be integrated into the genome of the host organism. The term "secretion vector" refers to a vector designed to provide secretion of a protein from the host organism.

The term "plasmid vector" herein refers to a vector that has been genetically modified to insert one or more genes.

The term "signal peptide" herein refers to a N-terminal amino acid sequence which, when attached to a target polypeptide, permits the export of the target polypeptide from the cell and cleavage of the signal peptide. The signal peptide accesses the general protein secretion pathway. An example of a signal peptide is the Divergicin A signal peptide described in amino acid SEQ ID NO:7. Other signal peptides can be used and are known to those skilled in the art. See SEQ ID NO:9, SEQ ID NO:11, and SEQ ID NO:13.

The term "leader peptide" herein refers to a N-terminal amino acid sequence which, when attached to a target polypeptide, permits the export of the target polypeptide from the cell and cleavage of the leader peptide. The leader peptides include but are not limited to a sequence of 15–24 amino acids that are able to be direct export of polypeptides from the cell using the cell's dedicated transport system. The leader peptide sequences shares similarity on their primary structure and contain a conserved processing site of glycine-glycine residues or glycine-alanine residues at positions-2 and -1 of the processing site. The dedicated transport system includes but is not limited to the ATP binding cassette (ABC) transporter required for leader peptide-dependent transport. There are many different leader peptides that could be used including, but not limited to, leucocin A, Colicin V, carno-bacteriocin A, carnobacteriocin B2, enterocin 900 or carno-bacteriocin BM1.

A "processing peptide" includes both leader peptides and signal peptides, and may refer to both simultaneously, as used herein.

The term "cassette" herein refers to a DNA sequence containing a series of bacteriocin genes and if necessary their respective immunity genes, appropriate promoters, ribosomal binding site (RBS) and terminating sequences and if necessary other regulatory DNA sequences. The cassette consists of two or more nucleotide sequences encoding a structural (bacteriocin or other substrate) gene linked directly to an N-terminal signal peptide DNA sequence compatible for export through the cell's general export pathway or linked to the leader peptide DNA sequence compatible for export through the dedicated transport system of the cell or through a compatible dedicated transport system also inserted into a vector used to transform the cell.

The term "food-grade" herein refers to the origin of the DNA material. Food-grade indicates that a regulatory agency would consider the substance as coming from a "food" source and therefore suitable for inclusion in food or food products. Organisms that are food-grade, such as lactic acid bacteria and other established genera of starter organisms, can be added directly to food without concern for pathogenicity.

The term "bacteriocin" herein refers to polypeptides and proteins that inhibit one or more bacterial species. This includes, but is not limited to, polypeptides or proteins that were derived from specific strains of bacteria, proteins that were derived from other types of organisms or proteins developed through genetic engineering. The bacteriocin can be bacteriostatic or bactericidal.

The term "class II bacteriocin" herein refers to a bacteriocin which includes but is not limited to small or moderate sized polypeptides. This includes but is not limited to heat resistant polypeptides and heat sensitive polypeptides that do not undergo post-translational modification except for cleavage of the leader or signal peptide and in some cases formation of disulfide bridges. This protein must have suitable size and properties so that it can be exported from a cell. Class II bacteriocins include, without limitation, carnobacteriocin UAL26, leucocin A, brochocin-C, entero-cin 900, divergicin A, carnobacteriocins A and B2.

The term "class II protein" herein refers to a small protein or polypeptide which does not undergo post-translational modification except for cleavage of the leader or signal peptide and in some cases the formation of disulfide bridges. This protein must be a suitable size and physico-chemical properties so that it can be exported from a cell. Many such proteins or polypeptides are known. One of ordinary skill in the art can determine which proteins would be suitable without undue experimentation. These proteins include, but are not limited to, enzymes, inhibitors that are polypeptides or other regulatory polypeptides or proteins.

The term "immunity gene" herein refers to a gene that produces a protein that protects the host organism against the bacteriocin that it produces.

The term "host organism" herein refers to a living bacterium or microorganism capable of taking up the plasmid vector, expressing the genes and producing the desired peptide(s). If the secretion of the desired polypeptide is required, the host organism must have functional transport proteins compatible with the signal or leader peptide attached to the polypeptide to be exported or it must be able to incorporate the dedicated transport protein(s) necessary for the leader peptide-dependent export of the substrate generated from vector DNA. Host organism capable of utilizing the divergicin A signal peptide use the general secretory (sec-) pathway of the cell (for additional information see Pugsley (1993) and Simonen and Palva (1993) and references therein).

The term "transport proteins" herein refers to proteins that are in most cases are incorporated into the cell membrane of the host organism and facilitate the export of protein(s) with a signal or leader peptide specific for the transport protein to the outside of the organism. Additional regulatory components, binding sites or enzymes may also be required for the functioning of the transporter. The ABC transporter of a specific protease can cleave the signal or leader peptide.

The term "homologous transporter system" indicates that the transport system and the leader peptide or signal peptide used to export polypeptides arise from the same host.

The term "heterologous transporter system" indicates that the transport system and the leader peptide or signal peptide used to export polypeptides arise from the different hosts. Divergicin A, for example of a signal peptide that can be used in heterologous transport systems. Homologous transporter systems can used in homologous or heterologous bacteria if the transport system is introduced into the host organism.

The term "meat" herein refers to muscle and fat tissue obtained from animal, fish, fowl or seafood including, without limitation, poultry, cattle, swine, sheep, deer, moose, fish and shellfish. The meat can be accompanied by bones, skin or internal organs. Meat can include other additives including but not limited to fillers, dyes, preservatives, natural or artificial flavoring. Meat can be raw, cooked, frozen, cured or canned. The meat would normally but not necessarily be packaged under vacuum or in a modified atmosphere containing elevated levels of carbon dioxide, i.e. vacuum or modified atmosphere (MAP).

The term "susceptible bacteria" refers to a species or strain of bacteria that is inhibited by the presence of one or more bacteriocins in its environment. Preferred susceptible bacteria are inhibited by brochin-C and/or enterocin 900.

The term "antibody" refers to antisera, monoclonal antibodies, antibody fragments, single chain antibodies and other functional equivalents capable of binding a bacteriocin of the invention. Preferred antibodies of the invention are capable of binding specifically to a bacteriocin of the invention without significant cross-reactivity with other bacteriocins. Antibodies of the invention are prepared by conjugating the polypeptide to a suitable carrier, such as keyhole limpet hemocyanin, and immunizing a suitable mammal (for example, mouse, rat, horse, goat, rabbit, and the like). It is preferred to employ an adjuvant to obtain an enhanced immune response. After time is permitted for antibodies to develop, they may be fractionated from blood. If desired, monoclonal antibodies may be prepared by generating hybridomas from splenocytes obtained from the immunized animal. Similarly, one may sequence antibodies and determine the sequence of the specific binding domain, for preparation of single-chain antibodies and the like.

The term "mutein" as used herein refers to a conservative variation of a bacteriocin of the invention. In general, a mutein will have an amino acid sequence that differs from the native sequence by 1–4 amino acid residues (including insertions and deletions). Muteins are easily prepared using modern cloning techniques, or may be synthesized by solid state methods. All muteins must exhibit bacteriocinogenic activity of at least a substantial fraction of the native sequence bacteriocin's activity (although not necessarily against the same susceptible bacteria), and may be tested using the methods described below.

General Methods

We have studied the fundamental characteristics and genetics of bacteriocin production and applied aspects of bacteriocins in meats. We have studied eight new bacteriocins from meat Tactics which show promising antagonistic activity. We have also developed "bacteriocin cassettes" (a series of DNA fragments encoding two or more bacteriocins) that would be equivalent to or better than nisin. The ability to do this is limited by fragment size at present due to difficulties of cloning large fragments of DNA.

By using the tools and techniques described herein, we have developed a system whereby one can select a range of bacteriocins against target bacteria, using the producer bacterium to deliver the antagonistic effect. This is applicable anywhere that lactic acid bacteria can grow without harming the environment to which they are added.

An important area of application for this innovative technique is in the preservation of meats and meat products. This advance will allow production of vacuum packaged meats and meat products with a predictable and longer storage life.

The carnobacteriocins disclosed herein are genetically complex and involve as much as 10 kb of DNA for their production. In contrast, leucocin A, produced by *Leuconostoc gelidum*, involves 4.5 kb of DNA. Leucocin-producing *L. gelidum* stops the spoilage of meat by sulfide-producing *Lactobacillus sake*; it inhibits the growth of pathogenic *Listeria monocytogenes*; and, when added to commercially produced ground beef, extends the color and odor storage life of retail ground beef.

Bacteriocins are synthesized in the cells as prepeptides consisting of a leader component of 15 to 24 amino acids that is cleaved to release the mature bacteriocin. In addition to this structural protein, bacteriocins like leucocin A require an immunity protein for protection of the cell from its own bacteriocin and two dedicated secretion proteins for export of the bacteriocin from the cell.

Most bacteriocins have dedicated bacteriocin secretion systems and if their genes are incorporated into another host organism they usually can not secrete the polypeptide or can only secrete the polypeptides to a lesser extent. Using the methods described herein an expanded antibacterial spectrum can be achieved by producing multiple bacteriocins in one bacterium such that the bacteriocins can be secreted.

We have also identified an important bacteriocin, divergicin A, produced by the meat lactic *Carnobacterium divergens*. The production of divergicin involves only 0.5 kb of DNA, because the leader peptide of divergicin accesses the general pathway for protein export from the cell. By fusing the structural and immunity genes of other bacteriocins behind the signal peptide of gene sequence of divergicin A, we have achieved production of bacteriocin(s) by host and heterologous bacteria. Utilizing the cell's secretory mechanism means that the dedicated secretory proteins of other bacteriocins do not need to be included in the bacteriocin cassette and leucocin A and other bacteriocins can be produced with only 0.5 kb of DNA each instead of 4.5 kb of DNA. This is an important breakthrough for the success of the bacteriocin cassette strategy.

We have also been able to produce and export a variety of bacteriocins or other proteins by placing their respective gene sequence(s) behind the divergicin signal peptide sequence in a plasmid and inside meat lactic organisms. This protocol has been tested and demonstrated to work using Divergicin A signal peptide as a leader to several polypeptides including but not limited to Carnobacteriocin B2, colicin V, Leucocin A, Brochocin-C and alkaline phosphatase.

Carnobacteriocin B2 is a well characterized class II bacteriocin produced by a 61-kb plasmid from *Carnobacterium piscicola* LV17. Export of this bacteriocin depends on a specific ABC (ATP-binding cassette) secretion protein. Divergicin A is a strongly hydrophobic, narrow spectrum bacteriocin produced by a 3.4-kb plasmid from *C. divergens* LV13 with a signal peptide that utilizes the general secretory pathway for export (Worobo et al., 1995). Fusion of the carnobacteriocin B2 structural gene (devoid of its natural leader peptide) behind the signal peptide of divergicin A permitted production and export of active carnobacteriocin B2 in the absence of its specific secretion genes. The immunity gene for carnobacteriocin B2 was included immediately downstream of the structural gene. Correct processing of the prebacteriocin occurred following the Ala-Ser-Ala cleavage site of the signal peptide. Carnobacteriocin B2 was produced by the wild type strain of *C. divergens* LV13 and in *C. piscicola* LV17C, the nonbacteriocinogenic plasmidless variant of the original carnobacteriocin B2 producer strain and other heterologous hosts. Both of the host strains are sensitive to carnobacteriocin B2 and they both acquired immunity when they were transformed with this construct.

An alternative approach to the use of signal peptide Divergicin A was also tested. Many nonlantibiotic bacteriocins of lactic acid bacteria are produced as precursors with a N-terminal leader peptide that share similarities in amino acid sequence and contain a conserved processing site of two glycine residues in positions-1 and -2 of the cleavage site. A dedicated ATP-binding cassette (ABC) transporter is responsible for the proteolytic cleavage of the leader peptides and subsequent translocation of the bacteriocins across the cytoplasmic membrane. To investigate the role that these leader peptides play in the recognition of the precursor by the ABC translocators, the leader peptides of leucocin A, lactococcin A or colicin V were fused to divergicin A, a bacteriocin from *Carnobacterium divergens* that is secreted via the cell's general secretion pathway. Production of divergicin was monitored when these fusion constructs were introduced into *Leuconostoc gelidum*, *Lactococcus lactis* and *Escherichia coli* that carry the secretion apparatus for leucocin A, lactococcins and colicin V, respectively. The different leader peptides directed the production of divergicin in the homologous hosts. In some cases production of divergicin was also observed when the leader peptides were used in heterologous hosts.

For ABC transporter-dependent secretion in *E. coli*, the outer membrane protein TolC was required: this is not found in lactic acid bacteria. Using the leader peptide strategy, colicin V was produced in *L. lactis* by fusing this bacteriocin behind the leader peptide of leucocin A. By fusing colicin V, which is normally produced by the Gram-negative bacterium *E. coli*, behind the Leucocin A leader peptide and inserting the plasmid into lactic acid bacteria, we have been able to get lactic acid bacteria to produce and export active colicin V. Similarly, by fusing other bacteriocins behind the leucocin leader, we have used the leucocin leader to direct the secretion of other bacteriocins by the leader's dedicated transport system. This is an important accomplishment because it enables the use of bacteriocins of Gram-negative origin in lactics (Gram-positive bacteria) or other Gram-positive organisms. For example, this enables the design of Food-Grade organisms to target Gram-negative pathogens such as Salmonella and *E. coli*. or for the design of organisms with specific fairly narrow or broad spectra of antibacterial activity.

The small amount of genetic material required using either the leader peptide or the signal peptide approach for independent bacteriocin expression permits the addition of multiple bacteriocins into the vector.

Chill stored, vacuum packaged beef inoculated with sulfide-producing *Lactobacillus sake* strain 1218 developed a distinct sulfurous odor within three weeks of storage at 2° C., at which time the bacteria had reached maximum numbers of $10^6$ CFU $cm^{-2}$. Co-inoculation of the meat with the wild type, bacteriocinogenic (Bac$^+$) strain of *Leuconostoc gelidum* UAL187 delayed the spoilage by *Lb. sake* 1218 for up to 8 weeks of storage. Co-inoculation of meat samples with an isogenic, slow growing Bac$^+$ variant UAL187-22 or with the Bac$^-$ variant UAL187-13 did not delay the onset of spoilage by *Lb. sake* 1218. The study showed that spoilage of chill stored, vacuum packaged beef by a susceptible target organism could be dramatically delayed by the Bac$^+$ wild type strain of *Leuc. gelidum* UAL187. Inoculation with *Lb. sake* 1218 can be used as a model system to determine the efficacy of biopreservation of vacuum packaged meats (Leisner et al., 1996). Using the methods described herein, other bacteriocins and a food-grade vector, the breadth of antibacterial activity can be increased and the temperature range of protection broadened for this and other food applications.

The use of the methods described herein will enable the meat industry to reliably predict the storage life of vacuum packaged fresh meats.

This same technology can be applied for preservation of animal feeds such as silage; as animal and human probiotics; as a control for Salmonella in poultry intestines; and for human therapy against infections of mucosal tissue where Tactics are acceptable microflora.

We have identified bacteriocins with a spectrum of antagonistic activity against both Gram-negative and Gram-positive organisms. Described herein is a method to prepare and use gene cassettes with a broad spectrum of antagonistic activity. Using methods described herein a plasmid containing a cassette of genes containing two or more bacteriocin genes can be constructed and transformed into a host organism, resulting in export of the bacteriocins from the cell. The leader peptide can be specific for the dedicated secretion system(s) of the host organism or a common signal peptide suitable for a broader spectrum of host organisms (i.e. Divergicin A signal peptide).

Using these strategies, the antibacterial spectrum of the producer strain can be tailored to target a range of spoilage or pathogenic bacteria, including *E. coli* and *Salmonella*. Producer strains that grow in the target environment can be selected and specific bacteria can be targeted. Broad range bacteriocins that have been identified and characterized will be used as well as other bacteriocins that target specific organisms.

This invention refers to the tailoring of specific lactic acid bacteria that grow in hospitable environments, including human food, animal feed, the mouth, the gastrointestinal tract of humans and animals, and the female genital tract. Using the technology of multiple bacteriocin production and delivery using lactic acid bacteria, a range of bacteriocins will be produced by the bacteria in situ. The principle of multiple bacteriocin production is based on using signal sequence of divergicin A produced by *Carnobacterium divergens* LV13 or leader peptides from other bacteria and fusing structural components of bacteriocin genes and their immunity genes behind the signal peptide or leader peptide. The bacteriocins that can be exported include, but are not limited to, several from lactic acid (or closely related) bacteria and colicin V from *Escherichia coli*.

This invention includes, but is not limited to the following:

A method to export bacteriocins from cells using Divergicin A as the signal peptide sequence. This method involves fusing the signal peptide sequence of divergicin A produced by *Carnobacterium divergens* LV13 to the structural component of a bacteriocin gene devoid of its leader peptide followed for most bacteriocins by a region containing its immunity gene, inserting this into a vector then transforming a host organism. For most bacteriocins, its immunity gene must also be included in the plasmid or vector but its does not have to be directly attached to either the structural protein or the signal peptide.

A plasmid vector consisting of four DNA sequences operably linked together. The first sequence encodes a plasmid replication and maintenance sequence, the second DNA sequence encodes a signal peptide or leader peptide sequence which is attached directly to a third DNA sequence which encodes the polypeptide sequence of a bacteriocin protein devoid of its leader sequence, the fourth sequence encodes the immunity gene specific for said bacteriocin protein.

A method to prepare the plasmid vector described above and insert the vector into the host organism. The host organism possesses a transport pathway which utilizes the signal peptide encoded by the signal peptide sequence.

A plasmid vector, pCD3.4 (SEQ ID NO:14), which is a food-grade plasmid and method of use thereof.

A plasmid vector as described above wherein the signal peptide sequence is SEQ ID NO:7.

A plasmid vector as described above wherein the bacteriocin and immunity gene are class II bacteriocin.

A plasmid vector consisting of three DNA sequences operably linked together. The first sequence encodes a plasmid replication and maintenance sequence, the second DNA sequence encodes a signal peptide or leader peptide sequence which is attached directly to a third DNA sequence which encodes the polypeptide sequence of a Class Type II protein or polypeptide devoid of its leader sequence.

An insertion vector as described above wherein the third DNA sequence encodes an enzyme.

A plasmid vector containing at least five DNA sequences operably linked together. The first sequence encodes a plasmid replication and maintenance sequence, the second DNA sequence encodes a signal peptide which is attached directly to a third DNA sequence which encodes the polypeptide sequence of a bacteriocin protein, the fourth sequence encodes the immunity gene specific for said bacteriocin protein and the fifth sequence encodes a polypeptide sequence for a transport protein system compatible with the signal peptide.

A method as described above wherein the plasmid contains more than one bacteriocin.

A plasmid vector as described above wherein the sequence encoding for the transporter system is the Leucocin A transporter system and the leader is from Leucocin A.

The signal peptide or leader peptide for the methods described above can be selected from leucocin A, lactococcin A, divergicin A, colicin V or other sequences described herein or any other dedicated secretion proteins that are compatible with the host organism.

A novel plasmid pCD3.4 (SEQ ID NO:14) for transforming food grade bacteria.

A method to preserve beef by adding *Leuconostoc gelidum* UAL187.

A method of preserving meat using food grade bacterium genetically modified with an plasmid vector containing one or more bacteriocins.

A method wherein plasmid vector is pCD3.4 (SEQ ID NO:14) is used as a vector.

A method for using food grade bacterium for the protection or preservation of food.

A method for using food grade bacterium transfected with a vector containing one or more bacterium for the protection or preservation of food.

A method for treating bacterial infections in animals or humans using food grade bacterium containing a naturally occurring bacteriocin.

A method for treating bacteria infections in animals or humans using food grade bacterium which has been genetically modified as described herein using one or more bacteriocins.

A method for treating bacteria infections in animals or humans using a food grade bacterium which has been genetically modified as described herein.

A method to inhibit the growth of gram-negative and/or gram positive bacteria using one or more bacteriocins.

A method to inhibit the growth of gram-negative and/or gram-positive bacteria using a genetically modified host organism.

Brochocin-C bacteriocin genes and methods of use thereof.

Enterocin 900 bacteriocin genes and methods of use thereof.

A method to export class II polypeptides using a leader peptide sequence.

A method to export class II polypeptides using a signal peptide sequence.

Novel bacteriocins and leader peptides and a method of use thereof.

Method of using Leucocin A transporter genes.

A food-grade plasmid and method of use thereof.

A method to increase the shelf life of meat.

A method to test organisms for preservation of meat, dairy products or other food products.

A method to purify certain bacteriocins.

A method to export bacteriocins using a leader peptide sequence.

A method to export other polypeptides using a leader peptide sequence.

A method to introduce immunity to particular bacteriocins into host organisms.

EXAMPLES

The following examples are provided as a guide for those of skill in the art, and are not to be construed as limiting the claimed invention in any way.

Example 1
(Bacteriocins, Sources, Methods of Propagation)

Table 1 describes many different bacterial strains and plasmids, the bacteriocins they contain and references which provide additional information about the bacteriocin or bacterial strain. For information on the best method to grow a particular organism refer to the appropriate reference or reference therein.

Example 2
(Use of Signal Peptide to Direct the Secretion of Substrates)
Example using Divergicin A signal peptide and Carnobacteriocin B2 as substrate:
Bacterial strains and media. Bacterial strains and plasmids used in this study are listed in Table 1. Carnobacteria were grown in APT broth (Difco Laboratories, Detroit, Mich.) at 25° C. without agitation. *E. coli* was grown in Luria Bertani (LB) medium at 37° C. on a rotary shaker. Agar plates were made by addition of 1.5% (wt/vol) agar to broth media. Antibiotics were added as selective agents when appropriate, as follows: erythromycin 200 μg/ml and ampicillin 100 μg/ml for *E. coli* and erythromycin 10 μg/ml for carnobacteria. Stock cultures of the bacterial strains were stored at −70° C. in the appropriate broth containing 20% (vol/vol) glycerol.

Oligonucleotide primer synthesis and amplification reactions: In the 3' region of the nucleotide sequence encoding the signal peptide of divergicin A there is a HindIII restriction site located 10 nucleotides upstream of the sequence encoding mature divergicin A (Worobo et al, 1995). A 35-mer oligonucleotide designed to facilitate an in-frame fusion between the signal peptide of divergicin A and the structural gene of carnobacteriocin B2 was synthesized on a DNA synthesizer (Applied Biosystems 391 PCR Mate) for use as a PCR primer (JMc7; 5'-CCCAAGCTTCTGCTGTAAATTATGGTAATGGTGTT-3')(SEQ ID NO:40). The first 9 nucleotides of JMc7 regenerate the HindIII restriction endonuclease cleavage site followed by nucleotides encoding the carboxy-terminus of the divergicin A signal peptide. The last 21 nucleotides of the primer are complementary to the 5' sequence corresponding to the N-terminal sequence of the carnobacteriocin B2 structural gene (cbnB2) immediately following the Gly-Gly cleavage site of the leader peptide. The reverse primer for the PCR amplification (ImmR) was based on the 3' nucleotide sequence of the immunity gene for carnobacteriocin B2 (cbiB2) and contains an overhang of 9 nucleotides to accommodate an XbaI restriction endonuclease site (Pugsley, 1993). DNA was amplified in a 100 μl reaction using a temperature cycler (OmniGene, InterSciences Inc., Markham, Ont.). PCR mixtures contained 1.0 μM of each primer, 200 μM of dNTPs, 5 mM MgCl2, 2.5 units of Tli DNA polymerase (Promega) and 1× reaction buffer (Promega). pLQ24 was used as template DNA for the reaction (Pugsley, 1993). DNA was amplified with 36 cycles (denaturation, 93° C., 1 min; annealing, 48° C., 1 min; extension, 75° C., 2 min) followed by a final extension step at 75° C. for 5 min.

DNA isolation, manipulation and sequence determination: Isolation of plasmid DNA from *E. coli* and carnobacteria was done using the methods described by Sambrook et al, 1989, and Worobo et al, 1994. Miniprep plasmid extractions for *E. coli* MH1 included a phenol-chloroform step which was necessary for restriction endonuclease analysis. Standard methods were used for restriction enzyme digestion, ligations, gel electrophoresis and *E. coli* transformation (Sambrook et al, 1989). Transformation of carnobacteria was done as described by Worobo and associates (1995). DNA was sequenced by Taq DyeDeoxy Cycle sequencing (Applied Biosystems 373A). Sequences were determined bidirectionally in pUC118 using universal primers.

Production of and immunity to divergicin A and carnobacteriocin B2: Carnobacteria transformed with either pRW19e or pJKM14 were tested for bacteriocin production using the deferred antagonism assay as described by Ahn and Stiles (1990) and references therein. Strains containing pMG36e were used as negative controls. Immunity to divergicin A and carnobacteriocin B2 was determined with the transformants as indicators in deferred inhibition assays. To confirm that the zones of inhibition were caused by a proteinaceous compound, they were inactivated by spotting Pronase E (1 mg ml−1; Sigma) prior to overlayering with the sensitive indicator strain.

Purification and N-terminal sequencing of carnobacteriocin B2: Partial purification of carnobacteriocin B2 was done with a 1% inoculum of an overnight culture of *C. divergens* LV13 containing pJKM14 grown in 2 liters of APT broth for 21 h maintained at pH 6.2 with a pH stat (Chem-Cadet; Cole Palmer). The culture was heated (70° C., 35 min) and cells were removed by centrifugation. Supernatant was loaded onto an Amberlite XAD-8 column (4×40 cm; BDH Chemicals, Poole, England) equilibrated with 0.05% trifluoroacetic acid (TFA). The column was washed successively with 3 liters of 10, 35 and 40% ethanol. *C. divergens* LV13 containing pJKM14 produces carnobacteriocin B2 and divergicin A, hence *C. divergens* LV13 was used as the sensitive indicator strain to eliminate inhibition zones produced by divergicin A. The active fraction was eluted with 3 liters of 50% ethanol. This fraction was concentrated by rotary evaporation to approximately 50 ml, and 10 ml was applied to a Sephadex G-50 column (2.5×120 cm, Pharmacia) with a running buffer of 0.05% TFA. Contents of tubes with inhibitory activity were collected, pooled and concentrated by rotary evaporation to 1 ml. Various amounts of partially purified carnobacteriocin B2 were subjected to sodium dodecyl sulfate-polyacrylamide gel electrophoresis (SDS-PAGE) and blotted onto polyvinylidene difluoride membrane (Bio-Rad). A duplicate polyacrylamide gel was washed twice with 1 liter of water and the gel was placed onto an APT plate and overlayered with soft APT agar inoculated with 1% of *C. divergens* LV13. The band corresponding to inhibitory activity was excised from the membrane and used for N-terminal sequencing by Edman degradation as described by Worobo et al. (Worobo et al, 1995). Construction of plasmids pRW19e and pJKM14. The bacteriocinogenic plasmids pRW19e and pJKM14 were constructed for use in this study. Both plasmids are derivatives of the lactococcal expression vector pMG36e (Van de Guchte et al, 1989) and transcription of the bacteriocin genes is under control of the P32 promoter for construction of pRW19e, a 514-bp EcoRV-AccI fragment of pCD3.4 (SEQ ID NO:14) containing both the structural and immunity genes for divergicin A (Worobo et al, 1995) was cloned into the SmaI and AccI sites of pMG36e. When *C.piscicola* LV17C was transformed with pRW19e the inhibitory spectrum matched that of *C. divergens* LV13 (Table 5). Zones of inhibition were inactivated by pronase E. *C.piscicola* LV17C with pRW19e also acquired immunity to divergicin A (Table 5). For construction of pJKM14, a 528-bp fragment was amplified by PCR from pLQ24 using the primers JMc7 and ImmR. This fragment was cloned into the HindIII and XbaI sites of pUC118 to create the plasmid pJKM05 and sequenced in both directions to confirm the fidelity of the reaction. An internal EcoR1 site located in the 5' region of cbiB2 was utilized to generate two subclones for completion of the overlapping sequence. No errors were detected in the nucleotide sequence compared with nucleotide sequence of the structural and immunity genes for carnobacteriocin B2 (Quadri et al, 1994). The 528-bp fragment was excised from pJKM05 using HindIII and KpnI and cloned into these sites in pRW19e, replacing the divergicin A structural and immunity genes. The SacI-EcoR1 fragment from pJKM14 containing the fusion between the divergicin A signal peptide and the carnobacteriocin B2 structural gene was cloned into pUC118 and sequenced to confirm that the correct reading frame was maintained.

Production of and immunity to divergicin A and carnobacteriocin B2. Production of divergicin A and carnobacteriocin B2 was detected by deferred antagonism assay against sensitive indicator strains. *C. piscicola* LV17C and *C. diver-* gens LV1 3 were transformed with the plasmids pMG36e, pRW19e and pJKM14 to compare differences in bacteriocin production with the divergicin A signal peptide. Results of deferred inhibition tests ate shown in FIG. 1 and Table 5. *C. divergens* Lv13 is more sensitive to carnobacteriocin B2 than *C. pisciola* LV17C shown by the large inhibitory zone in FIG. 1B. Zones of inhibition for wild type strains and strains containing pMG36e were identical. When *C. pisciola* LV17C was transformed with pRW19e, divergicin A was produced as indicated by inhibition of strains sensitive to divergicin A. No activity was detected against *C. divergens* LV13. The wild type carnobacteriocin B2 producer *C. piscicola* LV17B produces at least two bacteriocins (Quadri et al, 1994) making comparison between the inhibitory spectra of *C. piscicola* LV17B and *C. piscicola* LV17C containing pJKM14 difficult to interpret. To confirm the identity of the inhibitory substance produced by *C.divergens* LV13 containing pJKM14, the bacteriocins were purified and N-terminal amino acid sequence of the probable carnobactetiocin B2 peak was determined and shown to be Val-Asn-Tyr-Gly-Asn-Gly-Val (Seq. ID No. 53). This sequence matches the mature sequence of carnobacteriocin B2 indicating that the inhibitory substance was in fact carnobacteriocin B2, and that proper processing of the bactetiocin occurred following the Ala-Ser-Ala processing site of the divergicin a signal peptide (SEQ ID NO:1). The nucleotide and amino acid sequence of the divergicin A signal peptide is shown fused to the structural gene of carnobacteriocin B2 devoid of its natural leader peptide (see SEQ ID NO:34 for full details of the carnobacterium B2 genes and sequences). The sequence for the mature carnobacteriocin B2, locations of the forward pritner (JMc7) used for PCR and the HindIII restriction site are indicated. Furthermore, production of carnobacteriocin B2 from pJKM14 was also accomplished in the two meat isolates *C. divergens* AJ and *C. piscicola* UAL26, and in *Lactococcus lactis* subsp. *lactis* IL1403. Using this strategy production of Leucocin A, Brochocin-C and Colicin V was achieved.

There are a large number of plasmids that could be used in place of the plasmids described herein. One of ordinary skill in the art can identify other suitable plasmids and insert the various combinations of other gene sequences described herein into one of these plasmids without undue experimentation.

Using a signal peptide gene to export alkaline phosphatase from the host: Using the procedure described herein and the Divergicin A signal peptide gene attached to alkaline phosphatase structural gene, the inventors were able to export active alkaline phosphatase from the host organism, *E. coli*. For amplification of the DNA encoding the mature part of alkaline phosphatase, primers KLR 179 (5'-GCGCAAGCTTCTGCTCGGACACCAGAAATGCCTGT-T-3') (SEQ ID NO:41) and KLR 180 (5'-GGCCAAGCTTGCCATTAAGTCTGGTTGCTA-3') (SEQ ID NO:42) were used with the *E. coli* $C_4F_1$ (Torriani, 1968) alkaline phosphatase gene as a template. Cloning of alkaline phosphatase was essentially as described in example 2 for Carnobacteriocin B2 and Worobo et al. 1995.

Assay for alkaline phosphatase: Cells from 1.5 ml of an overnight culture grown in LB broth were centrifuged (9000×g, 5 min, 25° C.) and washed in an equal volume of STE (50 mM NaCl, 10 mM Tris pH 8.0, 1 mM EDTA pH 8.0). The culture media and periplasmic fractions were assayed for alkaline phosphatase. Periplasmic fractions were prepared by resuspending the washed cells in 0.5 ml of 20% sucrose with 50 µl of 0.5 M EDTA and 25 µl of lysozyme (10 mg/ml) and incubating at room temperature for 15 min. The samples were centrifuged (9000×g, 5 min, 25° C.) and the supernatant was assayed for alkaline phosphatase activity (Torriani, 1968) by absorbance at 405 nm.

Example 3

Use of Leader Peptides to Direct Secretion of Substrates via Dedicated Transport System Bacterial strains and media. *C. divergens* LV13 (Worobo et al., 1995), *C. divergens* UAL278 (McCormick et al., unpublished), *L. gelidum* 187-13 and *L. gelidum* 187-22 (Hastings and Stiles, 1991), and *Pediococcus pentosaceus* FBB63C (Graham and McKay, 1985) were grown in APT broth (All Purpose Tween; Difco Laboratories Inc.) at 25° C. and 30° C., respectively. *L. lactis* IL1403 (Chopin et al., 1984) and *L. lactis* IL1403(pMB500) (van Belkum et al., 1989) were grown in glucose-M17 broth (Terzaghi and Sandine, 1975) at 30° C. *E. coli* strains MH1 (Casadaban and Cohen, 1980), DH5α (BRL Life Technologies Inc.), BL21(DE3) (Studier and Moffat, 1986), MC4100 (Casadaban, 1976), and ZK796 (Wandersman and Delepelaire, 1990) were grown in TY broth at 37° C. (Rottlander and Trautner, 1970). Solid plating media were prepared by adding 1.2% (wt/vol) agar to the broth media. *C. divergens* UAL278 cells propagated on agar medium were incubated under anaerobic gas mixture of 90% N2 and 10% CO2. *E. coli* strains transformed with the colicin V encoding plasmid pHK22 (Gilson et al., 1987) were grown in media that contained 0.2 mM 2,2'-dipyridyl to increase expression of the colicin V operons. When appropriate, antibiotics were added to the media at the following final concentrations: erythromycin (200 (g/ml), ampicillin (150 (g/ml), tetracycline (15 (g/ml) and chloramphenicol (25 (g/ml) for *E. coli*; erythromycin (5 (g/ml) for *L. lactis, C. divergens* and *L. gelidum*; and kanamycin (50 (g/ml) for *L. lactis*.

Bacteriocin assay. Bacteriocin production was tested as described previously (van Belkum and Stiles, 1995). To detect divergicin A production, a strain of *C. divergens* UAL278 that is resistant to leucocin A was used as an indicator. This resistant strain was isolated by exposing it to a sublethal concentration of leucocin A. *C. divergens* LV13, *L. lactis* IL1403, *P. pentosaceus* FBB63C and *E. coli* DH5α were used as indicator strains for leucocin A, lactococcin A, pediocin PA-1 and colicin V, respectively. In some cases, bacteriocin activity was also tested by spotting serial dilutions of the growth medium onto an indicator lawn.

Purification and N-terminal sequencing of divergicin A. To purify divergicin A from transformants of *L. gelidum* 187-22, a 1% inoculum of an overnight culture was grown in APT broth, which was maintained at pH 5.5 using a pH stat (Chem-Cadet; Cole Palmer). After 18 h, the culture was heated at 70° C. for 35 min and centrifuged for 10 min to remove the cells. The supernatant was loaded onto an Amberlite XAD-8 column (4 cm×40 cm; BDH Chemicals) equilibrated with 0.05% trifluoroacetic acid (TFA). The column was washed with equal volumes of 0.05% TFA, and 10%, 35%, and 45% ethanol in 0.05% TFA. The active fraction of divergicin was eluted with 50% ethanol in 0.05% TFA and concentrated 10-fold by rotary evaporation. Samples of 10 ml were loaded onto a Sephadex G-50 column (2.5 cm×120 cm; Pharmacia) that was equilibrated with 0.05% TFA. The active fraction was applied to a SDS-polyacrylamide (15%) gel for polyacrylamide gel electrophoresis (PAGE). After electrophoresis, the gel was fixed in 50% methanol and 10% acetic acid for 30 min, washed twice for 1 h with 1 liter of deionized water and overlayered on an APT plate with soft APT agar (0.7% wt/vol) inoculated with 1% of a *C. divergens* UAL278 culture to screen for divergicin activity. Another sample of the partially purified divergicin obtained from the Sephadex G-50 column was subjected to SDS-PAGE and electroblotted onto a polyvinylidene difluoride membrane (Bio-Rad) and the protein band corresponding to the inhibitory activity of the overlayer test was excised from the gel and used for N-terminal sequencing by Edman degradation, as previously described (Worobo et al., 1995).

Molecular cloning. Cloning and DNA manipulations were performed as described by Sambrook et al. (1989). Plasmid DNA from *E. coli* was isolated as described by Birnboim and Doly (1979). With some modifications (van Belkum and Stiles, 1995), the same method was used to isolate plasmid DNA from *L. gelidum* and *L. lactis*. Restriction endonucleases, Tli DNA polymerase, the Klenow fragment of *E. coli* DNA polymerase I, and T4 DNA ligase were obtained from Promega, Bethesda Research Laboratories, Boehringer GmbH, or New England Biolabs, and used as recommended by the suppliers. Competent *E. coli* cells were transformed as described by Mandel and Higa (1970). Electrotransformations of *L. lactis* and *L. gelidum* were done according to the methods of Holo and Nes (1989) and van Belkum and Stiles (1995), respectively.

Construction of plasmids. A two-step PCR strategy (FIG. 4) was used to obtain a fusion between the leucocin A leader peptide and divergicin A. DNA encoding the leucocin A leader peptide and a 176-bp upstream region was amplified by PCR using plasmid pMJ3 (van Belkum and Stiles, 1995) as a template and MB32 (5'-AATTCGAGCTCGCCCAAATC-3') (SEQ ID NO:43) that is complementary to the upstream region, and MB37 (5'-TGAGTAATTTTCGGTGCAGCACCTCCTACGACTTGT-TCGA-3') (SEQ ID NO:44) that is complementary to the leucocin A leader and divergicin A sequence, as primers. This PCR fragment was subsequently used as a megaprimer to amplify the structural gene encoding divergicin A and a downstream region that includes the immunity gene for divergicin, with pCD3.4 (SEQ ID NO:14) (Worobo et al., 1995) as a template and RW58 (5'-TACGCGCAAGAACAGACAAAATC-3') (SEQ ID NO:45) as the reverse primer. Using the SacI restriction site of MB32 and a HindIII restriction site 390-bp downstream of the immunity gene the resulting PCR fragment was cloned into plasmid pMG36e (van de Guchte et al., 1989), giving plasmid pLED1. In a similar way, the sequence encoding the lactococcin A leader peptide and a 375-bp upstream region was fused to the gene encoding divergicin A, except that in the first PCR step, plasmid pMB553 (van Belkum et al., 1991a) was used as a template and MB38 (5'-TGAGTAATTTTCGGTGCAGCTCCTCCGTTAGCTTCT-GAAA-3') (SEQ ID NO:46) that is complementary to the lactococcin A leader and divergicin A sequence, and MB39 (5'-TACGAATTCGAGCTCGCCC-3') (SEQ ID NO:47) that is complementary to the upstream region, were used as primers. The PCR product containing the resulting gene fusion was cloned into the SacI and HindIII sites of pMG36e, giving plasmid pLAD6. Plasmid pCOD1, that contains a gene fusion between the colicin V leader sequence and divergicin A, was constructed in an identical way to pLED1, except that MB42 was used as a PCR primer instead of MB37. MB42 (5'-ATTTTCGGTGCAGCACCTCCAGAAACAGAATCTAA-TTCATTAGAGTCAGAGTTCTCATAATAACTTTCCT0-CTTTT-3') (SEQ ID NO:48) is complementary to divergicin A, the entire colicin V leader sequence and a region immediately upstream of the leucocin A leader sequence. Plasmid pLD1 was made in the same way as pLED1, except that MB41 (5'-TGAGTAATTTTCGGTGCAGCCATAATA-ACTTTCCTCTTTT-3') (SEQ ID NO:49), a primer complementary to the region immediately upstream of the leucocin A leader sequence was used instead of MB37. In pLD1 the divergicin A is encoded without a leader peptide. To make a fusion between the leucocin A leader peptide and colicin V, the leucocin A leader sequence and the upstream region was amplified by PCR using pMJ3 as template and as primers MB32 and MB43 (5'-ATATCACGCCCTGAAGCACCTCCTACGACTTGTTCG-A-3') (SEQ ID NO:50) that is complementary to the leucocin A leader sequence and colicin V. The PCR product was then used as a megaprimer in a second PCR step using pHK22 (Gilson et al., 1987) as a template and MB44 (5'-AATTAAGCTTGGATCCTTCTGTGTGGATTGTCCAAT-3') (SEQ ID NO:51) complementary to the downstream region of the structural colicin V gene as the reverse primer. The resulting PCR fragment was cleaved with HindIII, a restriction site that is located in the sequence of MB44, and SacI and cloned into pMG36e, giving plasmid pLEC1. All constructs were sequenced by the dideoxy-chain method of Sanger et al. (1977). Plasmid pTLA1 was constructed by cloning a 0.6 kb SacI-SspI fragment from pLAD6 that encodes the divergicin A gene fused to the lactococcin A leader sequence into the multiple cloning site of plasmid pT713 (Tabor and Richardson, 1985).

Overexpression of diveraicin A precursor in *E. coli* by T7 RNA polymerase. Cultures of *E. coli* BL21(DE3) were grown to OD600 of 0.3 in TY broth supplemented with 0.2 mM 2,2'-dipyridyl. The cells were subsequently induced by the addition of IPTG at a final concentration of 0.4 mM. After 2 h of incubation the cells were harvested, washed and concentrated 100-fold in deionized water, and lysed by sonication at 4° C. The lysate was applied to a tricine-SDS-polyacrylamide gel of 16% acrylamide (wt/vol) and 0.5% (wt/vol) bisacrylamide as described by Schagger and von Jagow (1987). After electrophoresis, the gel was fixed for 30 min in 50% methanol and 10% acetic acid and washed twice with 1 liter of deionized water for 1 h each. Antagonistic activity was detected by overlayering the gel on an APT agar plate with soft APT agar containing *C. divergens* UAL278 as the indicator strain.

Figure 4:
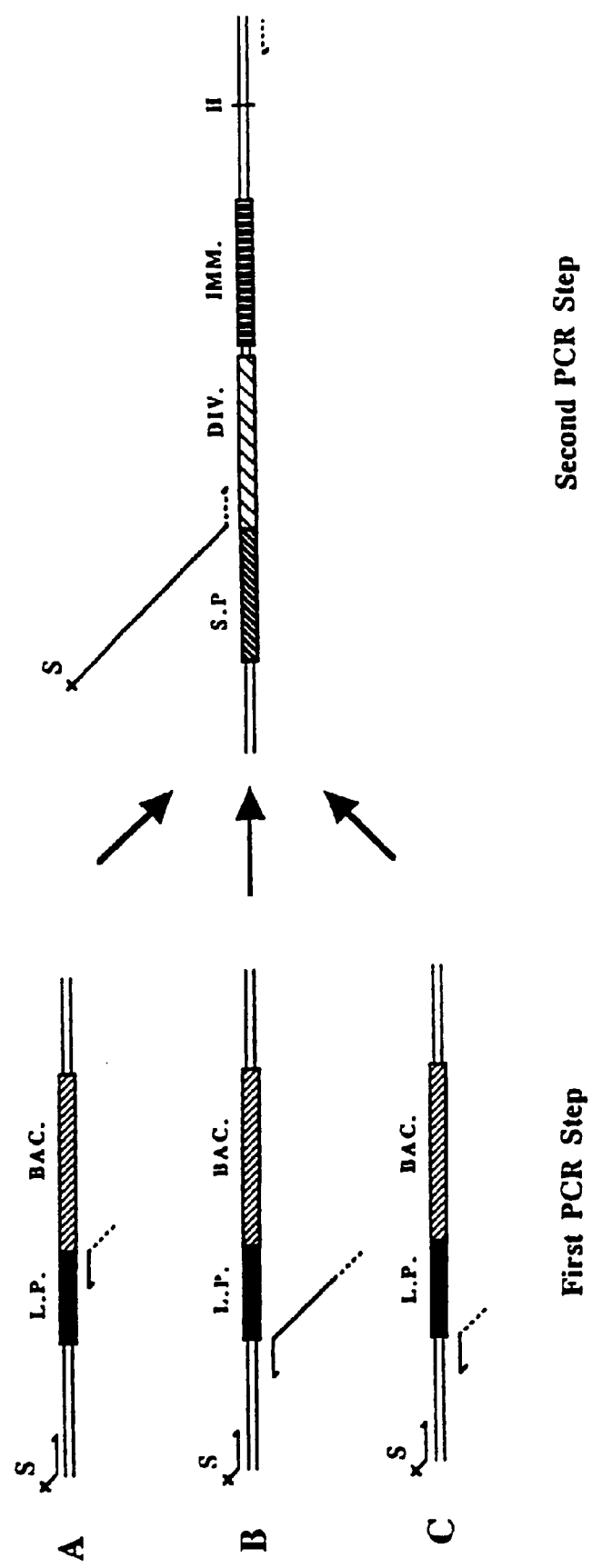
FIG. 4. Schematic representation of the two-step PCR strategy to replace the signal peptide of divergicin A with the double-glycine type leader peptides of leucocin A, lactococcin A or colicin V. In the first PCR step, the leucocin A (A and B) or lactococcin A (A) gene was used as a template to obtain a megaprimer containing the leucocin A (A), the lactococcin A (A), or the colicin V leader peptide (B). These megaprimers were used to amplify the divergicin A structural and immunity gene in a second PCR step. Divergicin A without a leader or signal peptide was constructed by first amplifying the region upstream of the leucocin A gene (C) and using the resulting PCR product to amplify the divergicin gene in the second PCR step. Further information is detailed in the text. Abbreviations: L.P.: DNA encoding the double-type glycine leader peptides; BAC: DNA encoding the mature part of leucocin A or lactococcin A; S.P.: DNA encoding the signal peptide of divergicin A; DIV: DNA encoding the mature part of divergicin A; IMM: immunity gene for divergicin A; S: SacI restriction site; H: HindIII restriction site.

Divergicin production in *Leuconostoc gelidum* and *Lactococcus lactis* using leader peptides from leucocin A and lactococcin A. Divergicin A is produced as a prepeptide that consists of a mature peptide of 46 amino acids and a classical N-terminal signal peptide of 29 amino acids (SEQ ID NO:6). The signal peptide of divergicin A was replaced with the double-glycine type leader peptides from leucocin A (SEQ ID NO:9) and lactococcin A (SEQ ID NO:11) by a two-step polymerase chain reaction (PCR) strategy as shown in FIG. 4. The DNA encoding the leucocin A leader peptide and a 176-bp upstream region was amplified by PCR. The resulting PCR fragment was used as a megaprimer to amplify the DNA encoding the mature peptide for divergicin and its immunity protein. The PCR product containing the gene fusion was cloned into the vector pMG36e to give plasmid pLED1. The gene fusion in pLED1 is under the control of the P32 promoter of pMG36e that is functional in a variety of bacteria (van der Vossen et al., 1987). To determine whether the secretion apparatus for leucocin A can recognize this hybrid protein, remove the leader peptide and translocate divergicin A into the external medium, plasmid pLED1 was introduced into *Leuconostoc gelidum*

Figure 8:
FIGS. 8(A)–8(B). Two restriction site maps plasmid pCD3.4. The location of the Divergicin structural and immunity genes are marked in B as dvnA and dviA respectively.
Figure 9:
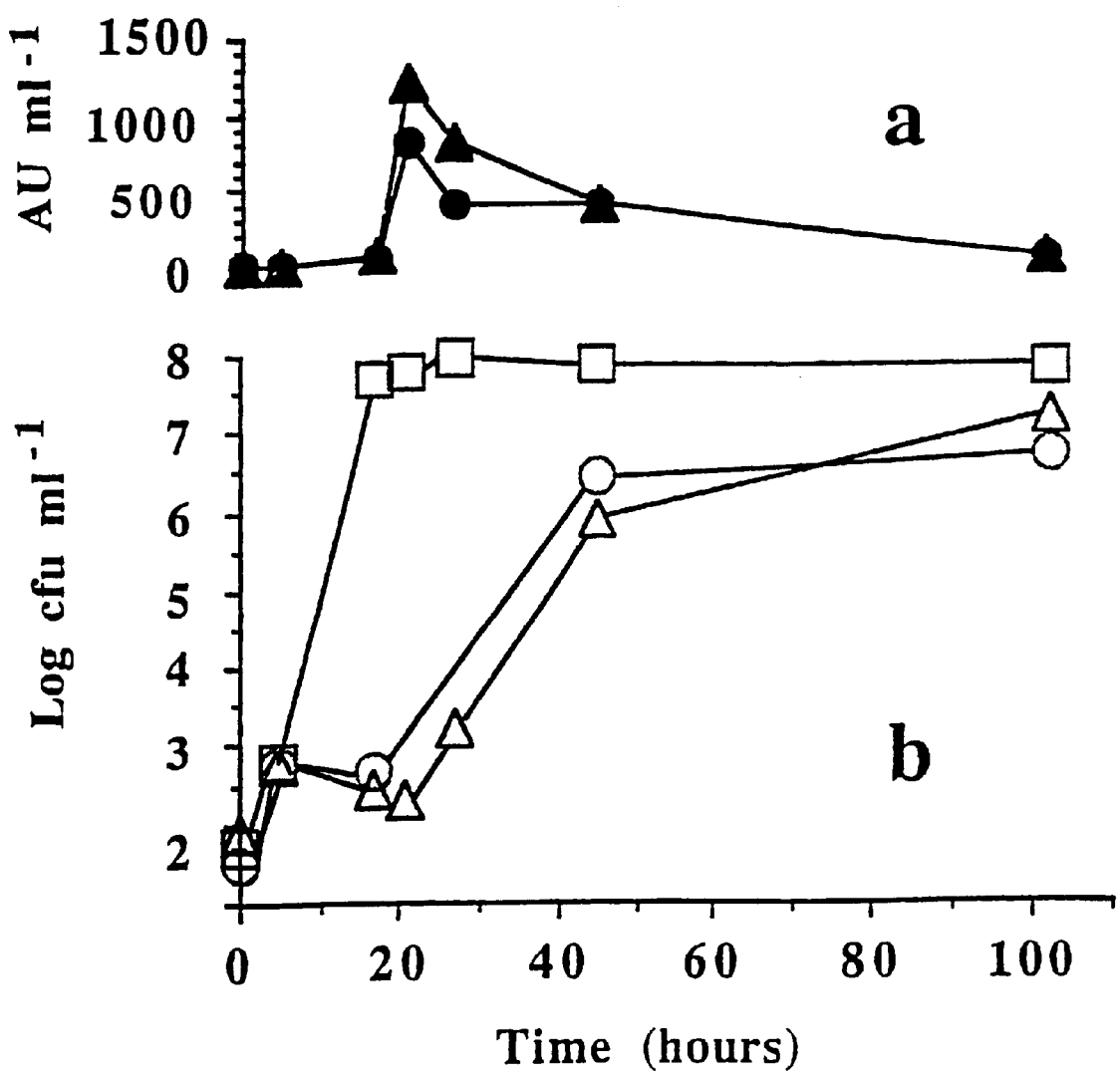
FIG. 9. Bacteriocin activity and growth of *Lactobacillus sake* 1218 in mixed culture with variants of *Leuconostoc gelidum* at 25° C. in mAPT with 0.1% glucose and the initial pH adjusted to 5.6. (a) Bacteriocin activity in arbitrary units (AU) per milliliter of supernatant for mixed cultures of *L. sake* 1218 and *L. gelidum* UAL187 (▼) and mixed cultures of *L. sake* 1218 and *L. gelidum* UAL187-22 (●). (b) Growth of *L. sake* 1218 with *L. gelidum* UAL187(Δ), *L. gelidum* UAL187-22(○), and *Leuc. gelidum* UAL187-13(□).

UAL187-22. The genetic determinants for leucocin A and its transport proteins LcaC and LcaD are located on one of the two plasmids found in this organism (Hastings et al., 1991; van Belkum and Stiles, 1995). *Carnobacterium divergens* UAL278 was used as a sensitive indicator strain to monitor divergicin production. Because *C. divergens* UAL278 is sensitive to leucocin A, a strain of UAL278 that is resistant to leucocin A was isolated by exposing *C. divergens* UAL278 to a sublethal concentration of leucocin A. This strain was used in subsequent studies to detect divergicin production. Production of divergicin A using this fusion construct was also monitored in *Lactococcus lactis* IL1403 carrying plasmid pMB500. This plasmid contains genes for the lactococcin transport proteins LcnC and LcnD and the structural and immunity genes for lactococcins A and B (van Belkum et al., 1989; Stoddard et al., 1992). Lactococcins A and B are only active against lactococci and do not inhibit the growth of *C. divergens*. When *L. gelidum* UAL187-22 and *L. lactis* IL1403(pMB500) were transformed with pLED1, production of divergicin A was observed (FIGS. 8 and 9). However, transferring pLED1 into *L. gelidum* 187-13, a derivative of UAL187-22 that has been cured of the leucocin plasmid (Hastings and Stiles, 1991), or into *L. lactis* IL1403, production of divergicin did not occur.

In a similar way, divergicin A was fused to the lactococcin A leader peptide. DNA encoding the lactococcin A leader sequence and a 375-bp upstream region was amplified. The resulting PCR product was used in a second PCR reaction to fuse the lactococcin A leader sequence to the divergicin gene. This PCR product was cloned into pMG36e, resulting in pLAD6. Transformation of pLAD6 into *L. gelidum* 187-22 or *L. lactis* IL1403(pMB500) resulted again in production of divergicin (FIGS. 8 and 9). Apparently, the leucocin A and lactococcin A leader peptides can direct the secretion of divergicin using the leucocin A as well as the lactococcin A transport proteins, respectively. The data shown in FIGS. 8 and 9 illustrate that *L. gelidum* 187-22 produced somewhat more divergicin with pLED1 than with pLAD6, while in *L. lactis* IL1403(pMB500) the opposite effect was observed. This was confirmed when divergicin activity in the supernatant of cultures of *L. gelidum* 187-22 and *L. lactis* IL1403 (pMB500) transformed with these two plasmids were compared. A culture of *L. gelidum* 187-22 transformed with pLED1 produced four times more divergicin than with pLAD6, while *L. lactis* IL1403(pMB500) transformed with pLAD6 doubled the production of divergicin compared with pLED1.

To confirm that inhibition of *C. divergens* UAL278 by *L. gelidum* 187-22 carrying pLED1 or pLAD6 was caused by divergicin A production and not by leucocin A, the inhibitory compound was partially purified and the N-terminal amino acid sequence was determined. The N-terminal amino acid sequence of Ala-Ala-Pro-Lys-Ile from the purified peptide indicated that the active compound was indeed divergicin A (Worobo et al., 1995) and that proteolytic cleavage occurred at the C-terminus of the two glycine residues of the leucocin A and lactococcin A leader peptides. This demonstrated that LcaC, the ABC transporter for leucocin A, correctly processed these leader peptides fused to divergicin A.

Figure 6:
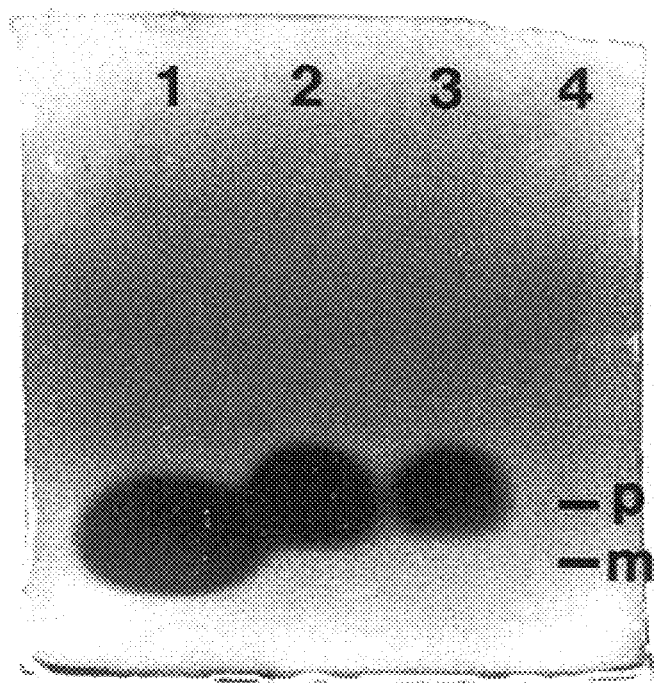
FIG. 6. Detection of antagonistic activity by divergicin A fused to the lactococcin A leader peptide in a tricine-SDS-polyacrylamide gel. *C. divergens* UAL278 was used as the indicator strain by the overlay test. Lane 1: supernatant of *L. gelidum* 187-22 carrying pLED1. Lanes 2,3 and 4: lysates of *E. coli* BL21(DE3) containing plasmids pHK22 and pTLA1, pTLA1, pTLA1, or pT713 and pHK22, respectively. Abbreviations: M: mature divergicin A; P: divergicin A precursor containing the lactococcin A leader peptide.

Some divergicin was produced when *L. lactis* IL1403 that did not contain pMB500 was transformed with pLAD6 (FIG. 6). It has recently been shown that *L. lactis* IL1403 carries a set of secretion genes on the chromosome that are homologous to the lactococcin secretion genes lcnC and lcnD of pMB500 (Venema et al., 1996). These results indicate that the transport proteins encoded on the chromosome of IL1403 recognize the hybrid protein containing the lactococcin A leader peptide but not when it contains the leucocin A leader peptide.

Figure 7:
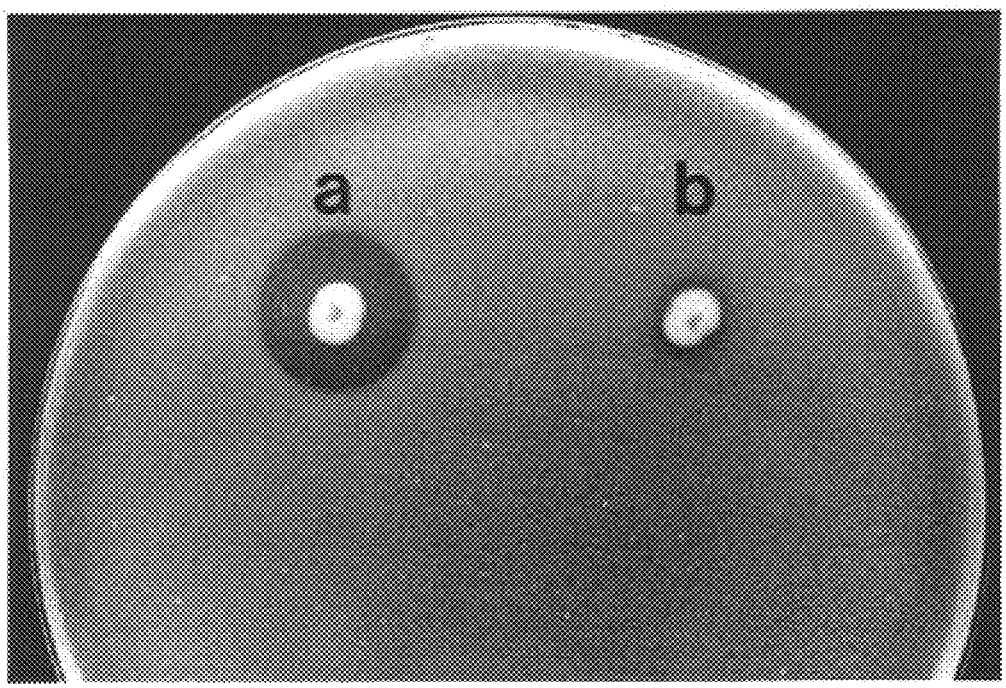
FIG. 7. Colicin V production in *L.lactis*. Deferred inhibition test by *L.lactis* IL1403(pMB500) transformed with (a) pLEC1 or (b) pMG36e using *E.coli* DH5α as the indicator strain.

Divergicin A production using the colicin V secretion apparatus. To determine whether divergicin A fused to the leucocin A or lactococcin A leader peptides could be secreted by *E. coli* using the transport proteins for colicin V, pLED1 and pLAD6 were transformed into *E. coli* MC4100 carrying pHK22. Plasmid pHK22 contains the structural gene of, and the immunity gene for, colicin V as well as the genes encoding the two inner membrane transport proteins CvaA and CvaB for colicin V (Gilson et al., 1990). With plasmid pLED1, but not with pLAD6, divergicin could be produced in *E. coli* MC4100(pHK22) (FIG. 7). To compare the efficiency of divergicin secretion by the colicin V secretion apparatus using the leucocin A leader peptide with that when the colicin V leader peptide (SEQ ID NO:13) was used, plasmid pCOD1 was constructed. Plasmid pCOD1 is identical to pLED1 except that the leucocin A leader peptide was replaced by the colicin V leader peptide (FIG. 4). The zone of inhibition of *C. divergens* eUAL278 formed by *E. coli* MC4100 carrying pHK22 and pCOD1 was slightly larger than that produced by *E. coli* cells carrying the two plasmids pHK22 and pLED1 (FIG. 7). Divergicin production was not observed when pLED1 or pCOD1 were transformed into MC4100 that did not contain pHK22. The iron chelator 2,2'-dipyridyl was used in the medium to induce the colicin V promoters (Chehade and Braun, 1988; Gilson et al., 1990). Omitting this inducer from the medium greatly reduced production of colicin V as well as divergicin A.

Figure 5B:
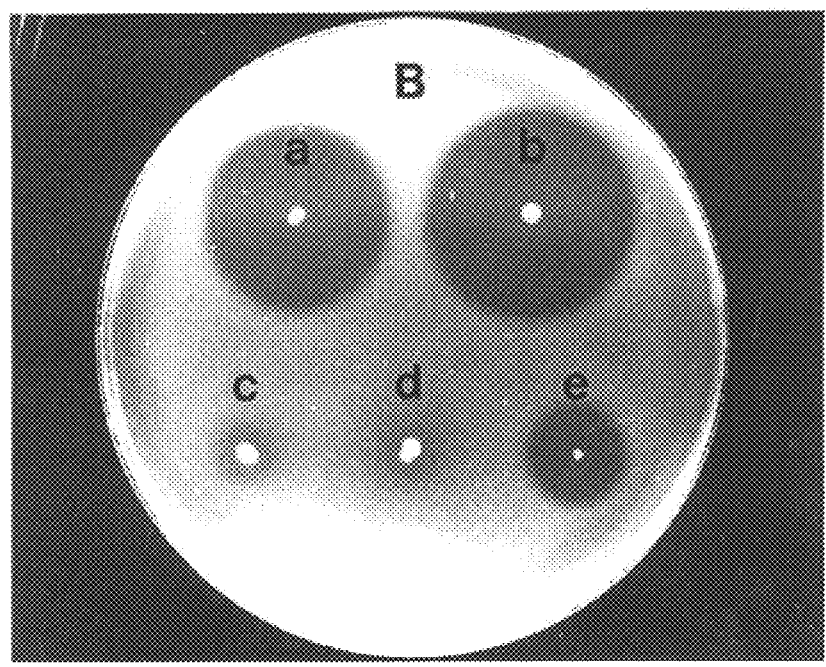
FIG. 5. Antagonistic activity of *L. gelidum* 187-22 (A), *L.lactis* IL1403(pMB500) (B), and *E.coli* MC4100(pHK22) (C) transformed with pLED1 (a), pLAD6 (b), pCOD1 (c) or pMG36e (d). In panel (B) also antagonistic activity of *L.lactis* IL1403 transformed with pLAD6 (e). *C. divergens* UAL278 was used as indicator strain.
Figure 5A:
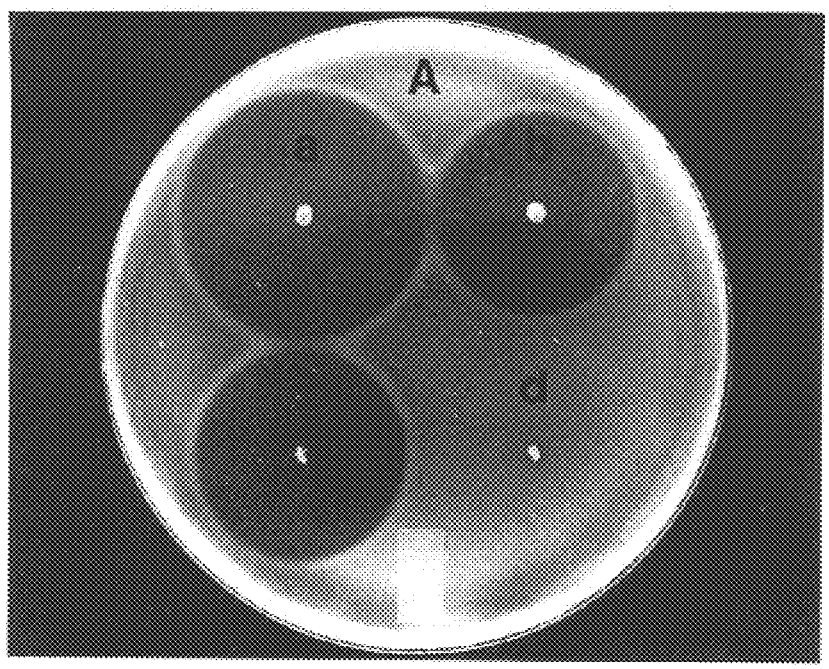
Figure 5C:
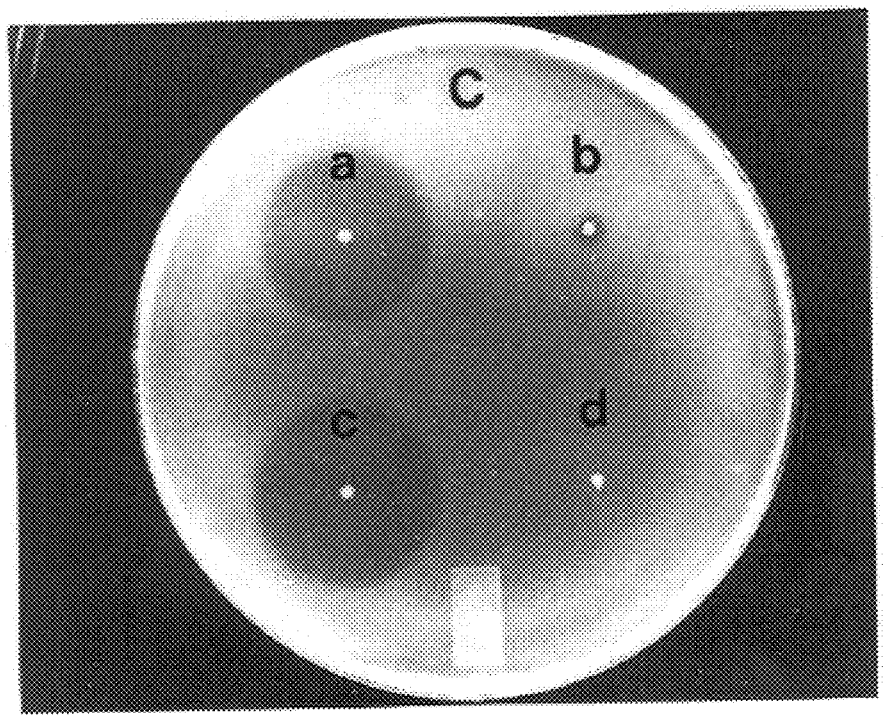

When *L. gelidum* 187-22 and *L. lactis* IL1403(pMB500) were transformed with pCOD1, production of divergicin was observed in UAL187-22 but not in IL1403(pMB500) (FIGS. 8 and 9). The colicin V leader peptide was not as efficient as the leucocin leader in directing the secretion of divergicin in *L. gelidum* 187-22 (FIG. 5).

As a negative control, pLD2 was constructed. It is identical to pLED1 or pCOD1 except that leader peptides that precede the mature part of the divergicin A peptide were excluded. *E. coli* MC4100 (pHK22) cells transformed with pLD2 did not inhibit the growth of *C. divergens* UAL278. Furthermore, the introduction of pLED1, pLAD6 or pCOD1 into *L. gelidum* 187-22, *L. lactis* IL1403(pMB500) and *E. coli* MC4100(pHK22) did not affect the production of leucocin A, lactococcins and colicin V, respectively.

TolC is required for ABC transporter-dependent transport. For translocation of colicin V across the outer membrane in *E. coli*, the presence of the minor outer membrane protein TolC is required (Gilson et al., 1990). To determine whether TolC is essential for divergicin A production in *E. coli*, pHK22 in combination with pCOD1 or pLED1 were introduced into *E. coli* ZK796, a TolCD derivative of MC4100 (Wandersman and Delepelaire, 1990). *E. coli* ZK796 (pHK22) containing pLED1 or pCOD1 did not produce divergicin A, indicating that divergicin A requires the TolC protein for the ABC protein-dependent secretion pathway in *E. coli*.

Colicin V secretion in *Lactococcus lactis*. The results described above indicate that leader peptides of the double-glycine type can direct the secretion of heterologous substrates using ABC tranporters. To determine whether colicin V, a bacteriocin of 88 amino acids (SEQ ID NO:32) that is produced by *E. coli*, can be exported by lactic acid bacteria using the leucocin A leader peptide, the leucocin A leader peptide was fused to colicin V. The same DNA sequence encoding the leucocin A leader peptide plus the 176-bp upstream region present in pLED1 was amplified by PCR and was used as a megaprimer to amplify the DNA encoding the mature part of colicin V and a downstream region of 54 bp. The resulting PCR product was cloned into pMG36e, giving plasmid pLEC2. When *L. lactis* IL1403(pMB500) was transformed with pLEC2, colicin V production was observed using *E. coli* DH5 as the sensitive indicator strain. No inhibition was observed when DH5a carrying pHK22 was used as the indicator strain. However, transformation of *L. gelidum* 187-22 with pLEC2 did not result in secretion of colicin V. Apparently, colicin V can be exported using LcnC and LcnD, but it seems that it cannot access the transport proteins for leucocin A.

The genes for the N-terminal amino acid extensions described by Worobo and associates (1995) and Quadri and associates (1994) would also be suitable for the using as leader sequences similar to those described herein.

In summary this protocol can be used to generate plasmids with more than one bacteriocin, or can be used to generate several plasmids with different bacteriocins. Using these techniques in combination with the nucleotide or peptide sequence of the desired leader or signal peptide and the desired bacteriocin, one of ordinary skill in the art can determine how to isolate the appropriate genes, identify and prepare the appropriate primers and insert the appropritate genes into a plasmid without undue experimentation. The host cell is the organism that is safe to use in the proposed enviroment or is responsible for a particular function in the enviroment. For example, the particular strain of bacteria used to make a particular type of cheese would be a suitable host for making an organism which would inhibit the growth of a variety of undesirable organisms but still make the desired type of cheese. The desired leader sequence or signal peptide would be a leader sequence found associated with a bacteriocin derived from the same species of bacteria or a general signal bacteriocin peptide. The bacteriocin selected would target undesirable organism found in the particular enviroment. For many application such as preservation of meat, both Gram-negative and a Gram-positive bacteriocins are desired therefore two or more bacteriocins would be required (one derived from a Gram-negative organism and the other derived from a Gram-positive organism.)

The dedicated secretion and accessory proteins of *Leuconostoc gelidum* UAL187 can be used to produce several different bacteriocins from one cell. The bacteriocins produced can be targeted against a range of bacteria, and those produced to date include colicin V in combination with one or more bacteriocin derived from leucocin A, carnobacteriocin B2 or other bacteriocins described herein.

Example 4

Spectrum of Bacteriocins Antibiotic Activity

The antibiotic spectrum of a bacteriocin can be determined by a variety of methods including but not limited to direct and deferred antagonism methods or spot-on-the lawn testing as described by Ahn and associates (1990a and b) and van Belkum and Stiles (1995).

The spectrum of antibiotic activity of individual bacteriocins were determined using partially purified bacteriocins. The bacteriocins were purified by methods specific for the bacterocin (Henderson et al. 1992; Hechard et al 1992; Hastings et al 1991; Quadri et al; 1993; Worobo et al. 1994; UAL-26 and Brochocin-C to be described later) or obtained commercially such as Pediocin PA-1 (Quest; Flavors & Food Ingredients Co., Rochester, N.Y.). Bacteriocins activity was determined using *Carnobacterium divergens* LV13 grown on ATP agar and expressed in arbitrary units of inhibitory activity (AU) based on the reciprocal of the greatest dilution that is inhibitory to this indicator strain (Ahn and Stiles 1990). Several bacteriocins were tested using 10 $\mu$l/spot of 100 AU/ml or 800 AU/ml for inhibtion of growth of a variety of strains of bacteria grown on agar (APT for most organisms except for the following: Lactobacilli MRS broth containing 1.5% agar for Lactobacillus and Pediococcus strains; Tryptic Soy Broth containing 1.5% agar (TSB agar) for Bacillus, Staphylococcus and Streptococcus strains; TSB plus 0.6% yeast extract for Listeria strains; or Trypticase Peptone Glucose Yeast extract for Clostridium strains and the results are summarized in Tables 2, 3 and 4.

This procedure can be used to test the ability of specific bacteriocins to inhibit the growth of specific organisms. With this information partially purified or purified bacteriocins can be identified for the use in the control of the growth of particular organisms, particular groups of organisms or for the treatment of particular diseases.

Organisms can be engineered as described herein to incorporate one or more of the desired bacteriocins for the inhibition of the growth of particular organisms or groups of organisms using the genetically engineered organism.

Carnobacteriocin 26, Enterocin 900 and Brochocin-C would be very good inhibitors of a broad range organisms as indicated in Table 2, 3 and 4. Inhibition of the growth of these organisms is important for disease control or to reduce spoilage of agricultural products.

Example 5

Molecular Characterization of Genes Involved in the Production of the Bacteriocin Leucocin A from *Leuconostoc gelidum*

Leucocin A is a bacteriocin produced by *Leuconostoc gelidum* UAL187 isolated from vacuum packaged meat (Hasting and Stiles; 1991). It inhibits a wide spectrum of LAB as well as some strains of *Listeria monocytogenes* and *Enterococcus faecalis*. Curing experiments of UAL187 showed that the genetic determinant for leucocin A was located on one of the three plasmids found in this organism. The bacteriocin was purified and shown to contain 37 amino acids (Hastings et al. 1991). A degenerate oligonucleotide was used for hybridization with plasmid DNA of UAL187-22 which has only two of the three plasmids, pLG7.6 and pLG9.2, and still produces bacteriocin (Hastings and Stiles 1991). A 2.9-kb HpaII fragment of pLG7.6 showing homology was cloned and sequenced revealing the structural gene for leucocin A (lcnA) and a second open reading frame (ORF). It was postulated that this second ORF could encode an immunity protein (Hastings et al. 1991). Leucocin A was shown to be produced as a precursor with a 24 amino acid N-terminal extension. Transformation of several LAB with constructs containing the 2.9-kb fragment did not show production of leucocin A. UAL187-13, a cured, bacteriocin-negative derivative of the wild type strain, was refractory to transformation.

Leucocin A is a small heat stable bacteriocin produced by *Leuconostoc gelidum* UAL187. A 2.9-kb fragment of plasmid DNA that contains the leucocin structural gene and a second open reading frame (ORF) in an operon was previously cloned (Hastings, et al. 1991). When a 1-kb DraI-HpaI fragment containing this operon was introduced into a bacteriocin-negative variant (UAL187-13), immunity but no leucocin production was detected. Leucocin production was observed when an 8-kb SacI-HindIII fragment of the leucocin plasmid was introduced into *Leuc. gelidum* UAL187-

13 and *Lactococcus lactis* IL1403. Nucleotide sequence analysis of this 8-kb fragment revealed the presence of three ORFs in an operon upstream and on the opposite strand of the leucocin structural gene. The first ORF (lcaE) encodes a putative protein of 149 amino acids. The second ORF (lcaC) contains 717 codons and encodes a protein that is homologous to members of the HlyB-family of ATP-dependent membrane translocators. The third ORF (lcaD) contains 457 codons that encodes a protein with strong resemblance to LcnD, a protein essential for the expression of the lactococcal bacteriocin lactococcin A. Deletion mutations in lcaC and lcaD resulted in loss of leucocin production, indicating that LcaC and LcaD are involved in the translocation and production of leucocin A. A mutation in lcaE did not affect leucocin production. The secretion apparatus for lactococcin A did not complement mutations in the lcaCD operon to express leucocin A in *L. lactis*, but lactococcin A production was observed when the structural and immunity genes for this bacteriocin were introduced into a leucocin producer of *Leuc. gelidum* UAL187, indicating that lactococcin A could access the leucocin A secretion machinery.

To prevent confusion with nomenclature used for the genes involved in the expression of lactococcins, lcnA and ORF2 (Hastings et al. 1991) have been renamed lcaA and lcaB, respectively. We report the cloning and nucleotide sequence analysis of a second operon which is located adjacent to, and on the opposite strand of, the lcaAB operon. A construct containing the two operons was successfully transferred into *Leuc. gelidum* UAL187-13 and resulted in leucocin production.

Bacterial strains, plasmids and media. The bacterial strains and plasmids used in this study are listed in Table 1. *Escherichia coli* was grown in TY broth (Rotlander and Trautner, 1970) at 37° C.; *L. lactis* was grown in Glucose-M17 broth (Terzaghi and Sandine 1975) at 30° C.; and *Leuc. gelidum* and *Carnobacterium piscicola* were grown in APT broth (All Purpose Tween; Difco Laboratories Inc., Detroit, Mich.) at 25° C. Broth media were supplemented with 1.2% (wt/vol) agar for solid plating media. Selective concentrations of erythromycin for growth of *E. coli, L. lactis* and *Leuc. gelidum* containing recombinant plasmids were 200, 5 and 5 mg/ml, respectively. When appropriate, ampicillin was used at a final concentration of 150 mg/ml for *E. coli*, and kanamycin was used at a final concentration of 50 mg/ml for *L. lactis*.

Bacteriocin Assay. To test for production of leucocin, cells of *L gelidum* or *L.lactis* were inoculated, unless otherwise stated, onto APT and glucose-M17 agar plates, respectively, and incubated at 25° C. for 18 h. Soft APT agar (0.7% [wt/vol]) containing *C. piscicola* LV17C as the indicator strain was then poured onto the surface. After 15 h of incubation, the plates were examined for zones of inhibition. Immunity or resistance of the different strains to leucocin was determined by a spot-on-lawn test of 0.5 µg of the bacteriocin (Ahn & Stiles, 1990). Lactococcin production was tested as described above with *L. lactis* IL1403 as the indicator strain in soft glucose-M17 agar (0.7% [wt/vol]).

Molecular cloning. Plasmids from *E. coli* were isolated by the method described by Birnboim and Doly (1979). With some modifications, the same method was used to isolate plasmids from *L. gelidum* and *L. lactis*. Cells were lysed at 37° C. in 50 mM Tris-HCl (pH 8)-10 mM EDTA containing 5 mg of lysozyme and 100 µg of mutanolysin (Sigma. St. Louis, Mo.) per ml for 20 min. Restriction endonucleases, the Klenow fragment of the *E.coli* DNA polymerase I, and T4 DNA ligase were obtained from Promega (Madison, Wis.). Bethesda Research Laboratories (Burlington, Ontario, Canada), Boehringer Mannheim (Dorval, Quebec, Canada), or New England Biolabs (Mississauga, Ontario, Canada), and used as recommended by the supplier. Cloning and DNA manipulations were performed as described by Sambrook et al. (Sambrook et al., 1989). Competent *E.coli* cells were transformed by the method of Mandel and Higa (Mandel & Higa, 1970). Transformation of *L. lactis* by electroporation was performed with a Bio-Rad gene pulser (Bio-Rad Laboratories. Richmond, Calif.) by the method of Holo and Nes (Holo & Nes 1989). For transformation of *L. gelidum*, cells were cultivated in APT broth supplemented with 3% (wt/vol) glycine. Exponentially growing cells were harvested, washed once with water and twice with ice-cold electroporation buffer (5 mM potassium phosphate buffer [pH 7], 3 mM $MgCl_2$, in 1 M sucrose), and concentrated 100-fold in the same buffer. Subsequently, 50 µl of the cell suspension was mixed with 2 µl of plasmid DNA and held on ice for 5 min prior to electroporation. Immediately after electroporation, cells were diluted in 1 ml of APT containing 0.5M sucrose and 20 mM $MgCl_2$ and incubated for 3 h at 25° C. Cells were plated on APT agar containing the appropriate antibiotic, and transformants were visible after 3 to 4 days of incubation at 25° C.

Southern hybridization. For Southern hybridization, DNA was transferred to Hybond N (Amersham Canada Ltd., Oakville, Ontario,Canada), as described by Sambrook et al (Sambrook et al, 1989). Nonradioactive DNA probes were made with a random-primed labeling and detection kit (Boehringer Mannheim). Hybridization and immunological detection were performed as recommended by the supplier.

DNA sequencing. Nucleotide sequence analysis was performed by sequencing the DNA in both orientations by the dideoxy-chain method of Sanger et al. (Sanger et al.,1977). DNA was sequenced by Taq Dye Deoxy Cycle sequencing on an Applied Biosystems 373A DNA sequencer (Applied Biosystems, Foster City, Calif.). for sequencing, stepwise deletion derivatives of cloned DNA fragments were made with the Erase-a-Base system from Promega. In addition, a primer-walking strategy was used for nucleotide sequencing. Synthetic oligonucleotides were make with an Applied Biosystmens 391 PCR-Mate DNA sythesizer. Analysis of the nucleotide sequence was performed with a software program (DNASTAR, Inc., Madison, Wis.) The search for homology of the predicted amino acid sequences with those of proteins in the Swiss-Prot protein sequence database (release 30) was based on the FASTA algorithm of Pearson and Lipman (Pearson & Lipman, 1988).

Nucleotide sequence accession number. The entire nucleotide sequence is sequence number is presented in the paper van Belkum and Stiles, 1995, and some important sections of this gene are included in SEQ ID NO:3 (accession number L40491). *Leuconostoc gelidum* (strain UAL187) leucocin A ATP-dependent transporter and secretory nucleotide sequence herein referred to as SEQ ID NO:4. This sequence if incorporated into a vector and used to transform a cell enables a cell to export polypeptides with an a variety of N-terminal leader peptides including but not limited to polypeptides with a Leucocin A or a Colicin V leader peptide. Both the ABC-transporter (lcaC) herein referred to as SEQ ID NO:4 and accessory protein (lcaD) genes herein referred to as SEQ ID NO:5 are required for a functional transport pathway.

Cloning of the genes involved in the production of leucocin A. The 2.9-kb HpaII fragment containing the lcaAB operon was cloned in pUC118, resulting in pJH6.1F, and in the shuttle vector pNZ19 to form the plasmid pJH8.6L. Attempts to transform *Leuc. gelidum* UAL187-13 with pJH8.6L were unsuccessful (Hastings et al. 1991). Therefore, we used a different vector to introduce the 2.9-kb fragment (FIG. 2) into strain UAL187-13. Using the multiple cloning site of pUC118, the 2.9-kb insert in plasmid pJH6.1F was excised by digestion with EcoRI and HindIII and cloned into the EcoRI-HindIII sites of pGKV210. The resulting plasmid, pMJ1, was used to transform strain UAL187-13. However, all of the transformants examined showed the presence of spontaneous deletion derivatives of pMJ1. When a 1-kb DraI-HpaI fragment containing lcaA and lcaB was subcloned from the 2.9-kb fragment into the SmaI site of pGKV210, the resulting recombinant plasmid pMJ3 (FIG. 2) formed a stable transformant in Leuc. gelidum UAL187-13. This transformant was immune to leucocin A but did not produce the bacteriocin. Apparently, additional information encoded on pLG7.6 is required for expression of the bacteriocin phenotype. The plasmid pMJ20 (FIG. 2) was constructed by introducing a frame shift mutation in lcaB, by filling in the unique ClaI site with Klenow DNA polymerase. Immunity was not observed in UAL187-13 carrying this plasmid, indicating that lcaB encodes the protein necessary for immunity to leucocin A.

Figure 2:
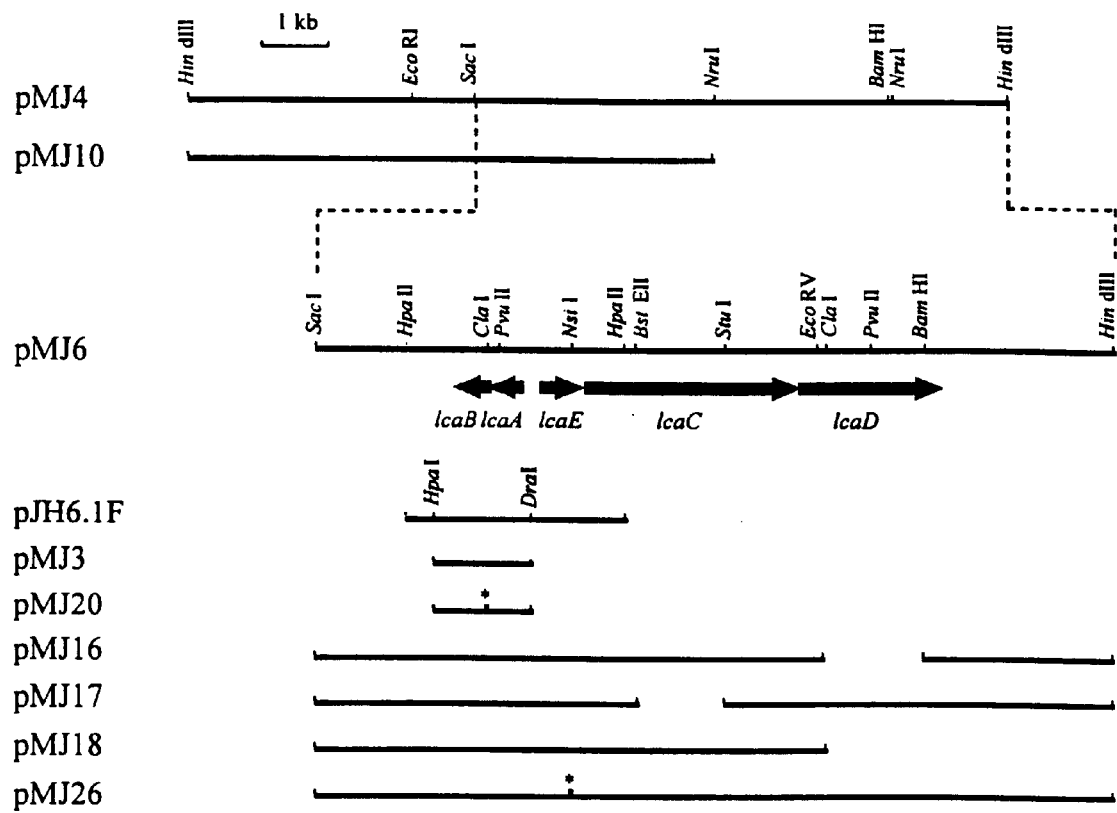
FIG. 2. Schematic representation of the 12.3kb HindIII insert of pMJ4 and its subclones. Partial restriction maps of some of the inserts are shown. Not all of the HpaII restriction sites on the insert of pMJ6 are indicated. The positions and direction of transcription of lcaA. lcaB. lcaC. lcaD. and lcaE on the insert of pMJ6 are shown. The asterisks on pMJ20 and pMJ26 indicate frameshift mutations of lcaB and lcaE, respectively.

Because additional genetic information is required for leucocin A production, regions adjacent to the lcaAB operon (FIG. 2) were cloned. It was previously reported that the producer strain UAL187-22 contains plasmids pLG7.6 and pLG9.2 of 7.6 and 9.2 MDa, respectively (Hastings and Stiles, 1991). Restriction analysis of plasmid DNA from UAL187-22 revealed that the actual sizes of pLG7.6 and pLG9.2 were 18 and 21 kb, respectively. To localize the lcaAB genes, Southern analysis of plasmid DNA with the 1-kb DraI-HpaI fragment as probe detected a 12.3 kb HindIII fragment that was cloned into pUC118 to give pMJ4. Subclones of this fragment into a shuttle vector gave pMJ6 and pMJ10 (FIG. 2).

Figure 3:
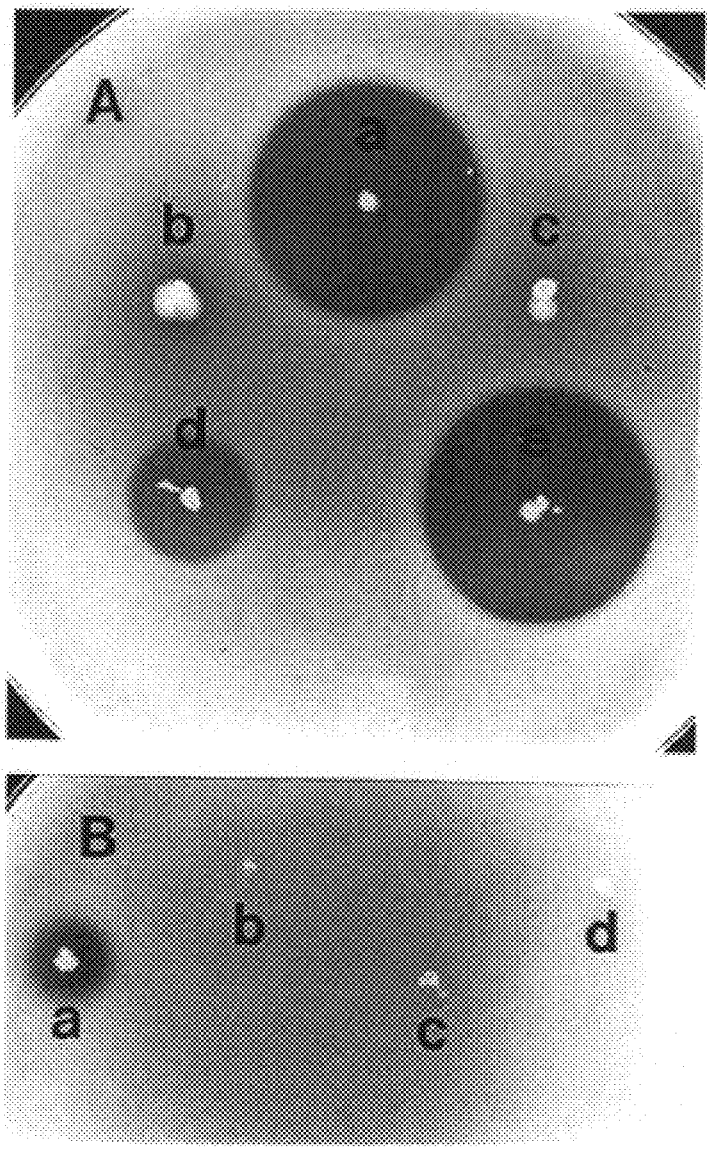
FIG. 3. Deferred inhibition of leucocin A transformants with *C. piscicola* LV17C as the indictor strain (A) and lactococcin A transformants with *L. lactis* IL1403 as the indicator strain (B). (A) a. *L. gelidum* UAL1877-22; b. *L. lactis* IL1403; c. *L. gelidum* UAL187-13; d. *L. lactis* IL1403 (pMJ6); e. *L. gelidum* UAL187013 (pMJ6). APT was used as solid medium. (B) a. *L. gelidum* UAL187-22)pMB553); b. *L. gelidum* UAL 187-13 (pMB553); c. *L. gelidum* UAL187-22; d. *L. geldum* UAL187-13. Glucose-M17 was used as solid medium.

Plasmids pMJ6 and pMJ10 were transformed into L. lactis IL1403 and screened for leucocin A production. Transformants containing pMJ6 but not pMJ10 inhibited the growth of the indicator strain C. piscicola LV17C. However, the zones of inhibition of these transformants were clearly smaller than those formed by Leuc. gelidum 187-22 (FIG. 3A). L. lactis has natural resistance to leucocin, therefore, the immunity phenotype to leucocin A could not be detected in L. lactis. Transformation of the bacteriocin-negative strain Leuc. gelidum UAL187-13 with pMJ6 resulted in several transformants containing deletion derivatives of pMJ6 that did not show production of the bacteriocin. A transformant of UAL187-13 which contained a plasmid with the expected size and restriction pattern of pMJ6 produced a zone of inhibition comparable to that formed by UAL187-22 (FIG. 3A). These results indicate that the genes responsible for the production of leucocin A are located on an 8-kb SacI-HindIII fragment of pLG7.6.

Nucleotide sequence analysis. Restriction analysis of pMJ6 revealed the location and orientation of the lcaAB operon on the 8-kb fragment (FIG. 2). The nucleotide sequence of the region upstream of the lcaAB operon was determined in both directions by the dideoxy-chain termination method. The nucleotide sequence in van Belkum and Stiles paper (1995) and partly in SEQ ID NO:3 shows a 4.3-kb segment located adjacent to the previously reported nucleotide sequence containing the lcaAB operon as well as part of this previously reported nucleotide sequence (Hastings et al. 1991). The start of an open reading frame (ORF) was identified 151 bases from, and on the opposite strand to, the start codon of lcaA. This ORF, designated lcaE, could encode a protein of 149 amino acids and is followed by a TAA stop codon. Immediately downstream of lcaE, a second ORF (lcaC) was found that contained 717 codons. The TAA stop codon of lcaC is immediately followed by an ORF that could encode a protein of 457 amino acids and has a TAG stop codon. All three ORFs are preceded by probable ribosomal binding sites. A possible promoter sequence was found upstream of lcae (van Belkum and Stiles, 1995). However, a putative promotor sequnce was also found within the lcaE gene. The sequence of its −35 (TGGACT) and −10 (TACAAT) regions closely resembles the consensus sequence of constitutive promoters found in other LAB (van de Guchte et al. 1992). The spacing of 16 and 19 bases between the −35 and −10 regions of these promotor seuquences agrees with that of the usual spacing found in LAB promoters. An imperfect inverted repeat was found 6 bases downstream of the stop codon of lcaD which has the characteristics of a possible rho-independent terminator. No other ORFs and palindromic structures were found in either strand in this 4.3-kb region.

Similarity of LcaC and LcaD to bacterial transport proteins. The hydrophobicity plot of the putative LcaC protein revealed that the N-terminal region contains several hydrophobic domains. A homology search with other amino acid sequences in the SwissProt database showed that LcaC belongs to the HlyB-like family of ABC transporters (Blight and Holland 1990; Higgins 1992). These proteins contain a highly conserved ATP binding domain in the C-terminal region and several membrane spanning domains in the N-terminal half of the sequence. Homology comparison of HlyB, which is involved in the secretion of hemolysin A, and LcaC revealed that 58% of the amino acids were similar when conserved residue substitutions are included and 27% were identical. However, LcaC has a much higher degree of homology with several other ABC transporters. ComA, a protein from Streptococcus pneumoniae that is required for competence induction for genetic transformation (Hui and Morrison 1991) shares 59% identity and 82% similarity with LcaC. Comparison of LcaC with LcnC, a protein that is implicated in the secretion of the lactococcal bacteriocin lactococcin A and possibly in the secretion of lactococcins B and M (Stoddard et al. 1992, van Belkum 1994), and PedD, which is involved in the production of pediocin PA-1 (Marugg et al. 1992), revealed 81% similarity and 57% identity, and 73% similarity and 51% identity at the amino acid level, respectively. The databank search showed further that LcaC was very homologous to SapT (82% similarity, 57% identity) and SapT (81% similarity, 58% identity), proteins that are encoded by DNA sequences linked to sakacin A and P, respectively. The highest score however, was found with MesC, a protein encoded in a DNA sequence linked to mesentericin Y that was nearly identical to LcaC with 99% similarity and 98% identity.

Analysis of the hydropathy profile of LcaD showed a largely hydrophilic protein with the exception of a strong hydrophobic region at the N-terminus. Homology search in the data bank revealed that LcaD is similar to LcnD, another protein that is essential for lactococcin production in L. lactis (Stoddard et al. 1992). LcaD showed 35% identity and 54% similarity to LcnD. Additional homologues of LcaD that were found were SspE (62% similarity, 32% identity), SapE (65% similarity, 35% identity) and MesY (96% similarity, 87% identity) whose genes are linked to the genetic determinants for sakacin A, P and mesentericin Y, respectively. Two other proteins that showed similarity with the LcaD protein were ComB from S. pneumoniae (Hui et al. 1995) with 61% similarity and 29% identity and the ORF1 protein encoded by Lactobacillus johnsonii (Fremaux et al.

1993). The ORF1 protein has similarity with the N- and C-termini of LcaD. The ORF1 protein is encoded by a 5' end truncated ORF of 540 bases located upstream of the bacteriocin operon responsible for lactacin F production (Fremaux et al. 1993).

The hydropathy profile of the putative protein LcaE showed a rather hydrophilic protein. Search of the databank revealed only similarity of LcaE to MesE, a protein encoded by a DNA sequence linked to mesentericin Y production. Functional and complementation analyses of LcaC and LcaD. To establish whether lcaE, lcaC and lcaD are essential for leucocin production, deletion and mutation derivatives of pMJ6 were constructed in E. coli (FIG. 2). Deletion of the BstEII-StuI fragment in lcaC resulted in plasmid pMJ17. Cells of Leuc. gelidum UAL187-13 containing this construct were immune to leucocin but bacteriocin was not produced. If we assume that the deletion had no polar effect on lcaD, the result would indicate that lcaC is involved in leucocin production. Two deletion constructs in lcaD were made, namely pMJ16 and pMJ18. In plasmid pMJ16 an EcoRV-BamHI fragment was deleted, whereas an EcoRV-HindIII fragment was deleted in pMJ18. A frame shift mutation in lcaE was made using the NsiI restriction site, giving plasmid pMJ26. Several attempts to introduce pMJ16, pMJ18 and pMJ26 into UAL187-13 were unsuccessful. When pMJ16 and pMJ17 were introduced into L. lactis IL1403, bacteriocin production was not detected. However, transformation of L. lactis IL1403 with pMJ26 did not affect leucocin production. These results indicate that LcaD, but not LcaE, is essential for leucocin production. Given the high degree of similarity between LcaC and LcaD of Leuc. gelidum and LcnC and LcnD of L. lactis, it was decided to determine whether the mutations in lcaC and lcaD could be complemented by the lactococcin A gene cluster in L. lactis IL1403 carrying pMB500 (Stoddard et al. 1992; van Belkum et al 1989). Plasmids pMJ3, pMJ16 and pMJ17 were used to transform IL1403(pMB500). Although the different plasmids contain the same replicon as pMB500, transformants can be selected for erythromycin resistance and pMB500 can be selectively retained by its own lactococcin production and resistance to kanamycin. However, leucocin production was not observed in these transformants, indicating that proper complementation by the lactococcin secretion apparatus was not possible. Only transformation of IL1403 (pMB500) with pMJ6 resulted in a zone of inhibition. In contrast, transformation of Leuc. gelidum UAL187-22 with plasmid pMB553, which carries the structural and immunity genes for lactococcin A showed a small zone of inhibition using L. lactis IL1403 as an indicator (FIG. 3B). Lactococcin A is only active against lactococci (Holo et al. 1991). No such zone of inhibition was observed when UAL187-13 was transformed with pMB553. Apparently, the leucocin secretion system is able to complement the lcnC and lcnD genes for the secretion of lactococcin A to a limited extent.

Example 6

Novel Bacteriocin Nucleotide and Amino Acid Sequences (Brochocin-C)

Brochothrix campestris ATCC 43754 isolated from soil as reported by Siragusa and Nettles Cutter ( ) to produce a broad spectrum bacteriocin. They did not characterize the bacteriocin and did not show that it is active against C. botulinum. We have now demonstrated that this is a two-component bacteriocin that is chromosomally produced and that the translation products of the two genes responsible for activity and an immunity gene (FIGS. 13, 14, 15 and 16). Biochemical and Genetic Characterization of Brochocin-C Brochocin-C is a strongly hydrophobic bacteriocin produced by Brochothrix campestris ATCC 43754 that is active against a broad spectrum of Gram-positive bacteria (Table 2 and 3). Crude brochocin-C was thermostable up to 121° C. for 15 min, pH stable from 2 to 9, and inactivated by proteolytic enzymes. The bacteriocin was purified, its nucleotide (SEQ ID NO:21) and amino acid sequence determined, and a site-specific 23-mer oligonucleotide probe was synthesized which hybridized to a 4.2-kb EcoRI genomic DNA fragment. The two components of the bacteriocin, brochocin A (nucleotide sequence herein referred to as SEQ ID NO:22 and amino acid sequence herein referred to as SEQ ID NO:23) and B (nucleotide sequence herein referred to as SEQ ID NO:24 and amino acid sequence herein referred to as SEQ ID NO:25), and their immunity gene (nucleotide sequence herein referred to as SEQ ID NO:26 and amino acid sequence herein referred to as SEQ ID NO:27) have been cloned separately and fused behind the signal peptide of divergicin A and produced in different hosts. Both Brochocin A and B contain a N-terminal leader peptide that gets cleaved after a double glycine motif to yield mature a bacteriocin and a leader peptide. This leader peptide bears significant homology to leader peptides of the class II bacteriocins of lactic acid bacteria.

Bacterial strains and plasmids: The bacterial strains and plasmids used in these studies are listed in Table 8. These include strains from the American Type Culture Collection (ATCC), Brochothrix strains from G. G. Greer isolated from meat at the Lacombe Research Centre and from our laboratory culture collection (UAL). All strains with the exception of Escherichia coli were stored at −70° C. in All Purpose Tween (APT) broth (Difco Laboratories Inc., Michigan) adjusted to pH 6.5, supplemented with 20% glycerol (v/v). Cultures for use in experimental studies were obtained by inoculation of frozen cells into APT broth at pH 6.5, and subcultured for two successive transfers at 25° C. after 18 to 24 h before being used. Growth experiments and (or) bacteriocin production from B. campestris were done in APT broth, Cooked Meat Medium (CMM; Difco), or semi-defined casamino acids medium (CAA), described by Hastings et al. (1991). CAA medium was used for the purification of the bacteriocin.

E. coli strains were stored at −70° C. in Luria-Bertani (LB) broth (Sambrook et al. 1989) supplemented with 40% glycerol (v/v). Inoculation of E. coli strains was done from frozen cultures into LB broth with ampicillin or erythromycin added to a final concentration of 200 mg/mL and propagated at 37° C. with shaking (250 rpm). Potential pUC118 recombinants were identified by the blue-white colour selection from growth on LB plates (1.5% w/v granulated agar) supplemented with ampicillin (200 mg/mL) and used with X-gal. (5-bromo-4-chloro-3-indolyl-β-D-galacto-pyranoside)

TABLE 8

Bacterial strains and plasmids

| Organism | Reference |
|---|---|
| Bacillus macerans ATCC 7048 | ATCC |
| B. cereus ATCC 14579 | ATCC |
| Brochothrix campestris ATCC 43754 | ATCC |
| B. campestris MT | This study |
| B. thermosphacta ATCC 11509 | ATCC |
| B. thermosphacta 141 | UAL |

TABLE 8-continued

Bacterial strains and plasmids

| | Reference |
|---|---|
| B. thermosphacta B1–B5, B7–B16 (inclusive) | GGG |
| Carnobacterium piscicola LV17 | Shaw |
| C. piscicola LV17A | Ahn and Stiles (1990n) |
| C. piscicola LV17B | Ahn and Stiles (1990b) |
| C. piscicola LV17C | Ahn and Stiles (1990b) |
| C. piscicola C2/8B | Quadri et al. (1994) |
| C. piscicola C2/8A | Quadri et al. (1994) |
| C. piscicola UAL26 | Burns (1987) |
| C. piscicola UAL26/8A | Ahn and Stiles (1990b) |
| C. piscicola UAL26/8B | Quadri et al. (1994) |
| C. divergens LV13 | Shaw |
| C. divergens 9/8A | Quadri et al. (1994) |
| C. divergens 9/8B | Quadri et al. (1994) |
| Clostridium bifermentans ATCC 19299 | ATCC |
| C. butyricum ATCC 8260 | ATCC |
| C. pasteurianum ATCC 6013 | ATCC |
| Enterococcus faecalis ATCC 19433 | ATCC |
| E. faecalis ATCC 7080 | ATCC |
| E. faecium ATCC 19434 | ATCC |
| E. durans ATCC 11576 | ATCC |
| Lactobacillus sake Lb706 | Schillinger |
| L. plantarum ATCC 4008 | ATCC |
| Lactococcus lactis ATCC 11454 | ATCC |
| L. lactis UAL 245 | UAL |
| L. lactis UAL 276 | UAL |
| Leuconostoc gelidum UAL 187 | Hastings et al. (1991) |
| L. gelidum UAL 187.13 | Hastings et al. (1991) |
| L. gelidum UAL 187.22 | Hastings et al. (1991) |
| L. mesenteroides ATCC 23386 | ATCC |
| L. mesenteroides Y105 | Cenatiempo |
| Listeria innocua ATCC 33090 | ATCC |
| L. monocytogenes Scott A | ATCC |
| L. monocytogenes I42 | UAL |
| L. monocytogenes ATCC 15313 | ATCC |
| Pediococcus acidilactici ATCC 8042 | ATCC |
| P. acidilactici PAC 1.0 | Vandenbergh |
| Staphylococcus aureus S6 | HPB |
| S. aureus S13 | HPB |
| Escherichia coli DH5α | BRL Laboratories Life Technologies Inc. |
| E. coli AP4.7 (DH5α containing pAP4.7) | This study |
| E. coli AP7.4–32 (DH5α containing pAP7.4) | This study |
| E. coli AP4.6–8 (DH5α containing pAP4.6) | This study |
| Plasmids | |
| pUC118 (3.2 kb; Amp$^R$; lac Z') | Vieira and Messing, (1982) |
| pGKV210 (4.4 kb; Em$^R$) | van der Vossen et al. (1985) |
| pAP4.7 (pUC118; 1.6 kb EcoRI - PstI fragment) | This study |
| pAP7.4 (pUC118; 4.2 kb EcoRI fragment) | This study |
| pAP4.6 (pUC118; 1.4 kb PstI fragment) | This study |
| pAP8.6 (pGKV210; 4.2 kb EcoRI fragment) | This study |

ATCC = American Type Culture Collection
BRL = Bethesda Research Laboratories Life Technologies Inc.
UAL = University of Alberta Food Microbiology culture collection
GGG = G. Gordon Greer (Lacombe Research Centre, Alberta, Canada)
HPB = Health Protection Branch (Ottawa, Ontario, Canada)
Shaw = B. G. Shaw (AFRC Institute of Food Research, Bristol, UK)
Vandenbergh = P. A. Vandenbergh (Quest International, Sarasota, US)
Burns = K. Burns (M. Sc. thesis, 1987, University of Alberta, Edmonton, AB)
Schillinger = U. Schillinger (Institute of Hygiene and Toxicology, Federal Research Centre for Nutrition, Karlsruhe, Germany)
Cenatiempo = Y. Cenatiempo (Institut de Biologie Moléculaire et d'Ingénierie Génétique, Centre National de la Recherche Scientifique, Université de Poitiers, France)

at final concentrations of each at 1.6 mg/mL. Erythromycin-resistant (Em$^R$) transformants of E. coli with pGKV210 were selected on either LB or YT (yeast extract, tryptone; Difco) agar with erythromycin (200 mg/mL).

Bacteriocin assays. Antagonistic bacteriocin activity against different indicator strains was determined by direct or deferred inhibition assays (Ahn and Stiles, 1990b). For direct inhibition tests, broth cultures were inoculated onto APT agar (1.5%) plates using a Cathra replicator, allowed to dry, and immediately overlayered with 7.5 mL of molten APT agar (0.75% agar) at 45° C., seeded with a 1% inoculum of the indicator strain. For deferred inhibition tests, inoculated cells were incubated at 25° C. for 15 to 18 h before being overlayered with the indicator strain as described above. In both instances, overlayered plates were placed in an anaerobic jar (BBL) filled with a 10% $CO_2$ and 90% $N_2$ atmosphere and incubated at 25° C. for 16 to 24 h before analyzing the results.

Bacteriocin activity of B. campestris ATCC 43754 was detected or quantified by the spot-on-lawn method (Ahn and Stiles, 1990b) against C. piscicola LV17C. Doubling dilutions (1:1) of cell supernatants (heat treated at 65° C. for 30 min) were prepared in sterile water and 10 or 20 mL of each dilution was spotted onto an APT plate freshly overlayered with the indicator lawn. Activity was determined by taking the reciprocal of the highest dilution which showed a distinct zone of inhibition of the indicator strain, and expressed as arbitrary activity units (AU) per mL.

Stability of brochocin-C. The effects of pH and heat treatment on the activity of crude brochocin-C were determined. Cultures grown in APT broth were centrifuged (8000×g for 15 min) and the supernatant was adjusted to pH 2 through 9 using either 5 N HCl or NaOH. The pH-adjusted supernatant was heated at 65° C. for 30 minutes before doing a spot-on-lawn assay. Heat stability of brochocin-C in pH-adjusted supernatant was determined by heating at 65° C. for 30 min, 100° C. for 15 min, or 121° C. for 15 min before testing the residual activity of each sample and comparing it with the activity in unheated supernatant. To test the effect of organic solvents on the activity of brochocin-C, preparations of brochocin-C partially purified by butanol extraction (see below) were diluted in either 0.1% trifluoroacetic acid (TFA), 95% ethanol, 100% methanol, or 100% acetonitrile to give an initial concentration of 10 AU/mL. Tubes were incubated at 25 and 4° C. for selected time intervals before a 10 mL aliquot of each treatment was removed and spotted onto a freshly overlayered lawn of C. piscicola LV17C. Sizes of the zones of inhibition were measured and compared to that at time zero for each treatment.

Plasmid curing. Overnight cultures of B. campestris were inoculated at $10^7$ cfu/mL into APT broth containing different concentrations of the curing agents novobiocin, acriflavin, and sodium-dodecyl sulphate (SDS) and grown at 25° C. for 24 h to determine the minimum inhibitory concentration of each.

The loss of bacteriocin production was determined from cultures grown in acriflavin by heating a 500 mL aliquot of the culture at 65° C. for 30 min and spotting it onto a lawn of C. piscicola LV17C. A negative control of sterile APT broth with the different concentrations of acriflavin was also spotted onto the indicator lawn to ensure that the acriflavin did not have an inhibitory effect on the indicator cells. Curing was attempted using a combination of acriflavin and elevated growth temperature (30° C.) using an inoculum of $10^4$ cfu/mL in APT broth with the selected acriflavin concentration. The culture was grown until turbidity was detected and then it was subcultured an additional 1 to 6 times at inocula of $10^3$ or $10^4$ cfu/mL in APT broth containing the same acriflavin concentrations. Dilutions of these cultures were made in sterile 0.1% peptone (Difco) water and plated onto APT plates. Plates were incubated in anaerobic jars at 25° C. for 2 d and replica-plated onto two other APT plates, allowed to grow for 2 d before overlayering one plate with *C. piscicola* LV17C and the other with *Listeria monocytogenes* 33090. Colonies showing a loss of bacteriocin production with both of the indicator strains were inoculated into APT broth for small-scale plasmid isolation (see below). The wild-type strain was also included in the small-scale plasmid isolations to serve as a positive control. Purification of brochocin-C. A flask containing five liters of sterile CAA medium (Hastings et al., 1991) with 2.5% glucose was inoculated with 2% of an overnight culture of *B. campestris* ATCC 43754, and grown at a constant pH of 6.7 with a Chemcadet (Cole-Parmer, Chicago, Ill.) by addition of filter-sterilized (0.22 mm) 2 M NaOH. Growth of the culture was monitored and stopped after 22 h of incubation at 25° C. Cells were removed from the culture broth by centrifugation at 8000×g for 20 min. The supernatant (approximately 5.5 liters) was extracted twice with 1.5 liters of n-butanol. The extract was diluted with water (approximately 1:1), concentrated on a vacuum evaporator at 35° C. and evaporated repeatedly to remove the last traces of butanol. The extract was suspended in water (approximately 150 mL), precipitated with 1.7 liters of cold (−60° C.) acetone and stored at 5° C. for 24 h. The precipitate was separated by centrifugation (10,000×g for 15 min), dissolved in 10 mL of 0.1% TFA and loaded onto a Sephadex G50 (Pharmacia) column (2.5×120 cm) that had been pre-equilibrated with 0.1% TFA. The column was washed with 0.1% TFA at a flow rate of approximately 0.6 mL/min. Absorbance of collected fractions was monitored at 220 nm. Fractions showing antimicrobial activity by spot-on-lawn assay were concentrated and lyophilized. The purity of the sample was confirmed by mass spectrum analysis and sodium-dodecyl sulphate polyacrylamide gel electrophoresis (SDS-PAGE).

SDS-PAGE. Brochocin-C preparations were examined on 20% poly-acrylamide gels with the buffer system described by Laemmli (1970) in 3M Tris-HCl. Electrophoresis was done at 20 mA constant current for 3 h. After electrophoresis, gels were fixed in 50% methanol, 10% acetic acid for 1 h and stained with Coomassie blue (Bio-Rad) or assayed for antimicrobial activity by overlayering with *C. piscicola* LV17C as the indicator strain by the method of Barefoot and Klaenhammer (1983).

Inhibition by brochocin-C. Partially purified preparations of brochocin-C were obtained by butanol extraction of supernatant fluids of an overnight culture of *B. campestris* ATCC 43754 grown in CAA medium with constant pH regulation at 6.7. All traces of butanol were removed by rotary evaporation. The partially purified bacteriocin was added to APT broth (pH 6.5) and to phosphate buffer (50 mM, pH 7.0) containing 10 cfu/mL of *C. piscicola* LV17C. The bacteriocin was added to give a final concentration of 100 AU/mL and the tubes were incubated at 25° C. Viable counts were determined by enumeration on APT agar at selected time intervals and cell lysis was checked by monitoring the optical density at 600 nm. For enumeration, cultures grown in APT broth and phosphate buffer were diluted in sterile 0.1% peptone water and 50 mM phosphate buffer (pH 7.0) respectively. Growth of the indicator strain without addition of bacteriocin was also included as a control.

Determination of the amino acid sequence and the amino acid content of brochocin-C. The N-terminal amino acid sequence of brochocin-C was determined by automated Edman degradation with a gas-phase sequencer (Applied Biosystems model 470A) with on-line phenylthiohydantoin-derivative identification by HPLC (Applied Biosystems model 120A chromatograph). The amino acid content of purified brochocin-C was determined by derivitization with phenylisothiocyanate on an Applied Biosystems 420A derivatizer and separation with a $C_{18}$ column by HPLC (Applied Biosystems model 130A chromatograph).

The mass spectrum of purified brochocin-C was measured by plasma desorption and fast atom bombardment (FAB).

DNA isolation, manipulation, and hybridization. Small-scale plasmid isolation of *B. campestris* was done by previously established methods (Ahn and Stiles, 1990b). Cells from an overnight culture grown in APT broth were recovered by centrifugation at 14,000×g for 5 min, washed once with cold 0.5% NaCl (500 mL), and resuspended in 100 mL of solution A (25% sucrose, 50 mM Tris-HCl, 5 mM EDTA, pH 8.0) containing lysozyme (10 mg/mL). After incubation for 1 h at 37° C., 200 mL of solution C (0.9% glucose, 3% SDS, 50 mM Tris-HCl, 5 mM EDTA, pH 8.0) containing 0.2 N NaOH was added and the tubes were gently inverted several times until the cell lysate cleared. Solutions of 2 M Tris-HCl, pH 7.0 (50 mL) and 5 M NaCl (70 mL) were added to the tubes and mixed by inversion. The DNA was extracted once with 3% NaCl-saturated phenol/chloroform and once with chloroform/isoamyl-alcohol (24:1), before overnight precipitation at −20° C. with 95% ethanol. Large-scale preparation of plasmid DNA was done by scaling up (100×) of the small-scale method using cells from 750 mL of an overnight culture grown in APT broth and purified by CsCl—ethidium bromide density gradient ultracentrifugation. The CsCl salt was removed by dialysis in 10 mM Tris-HCl, 1 mM EDTA (TE buffer, pH 8.0; Sambrook et al., 1989). Chromosomal DNA preparation of *B. campestris* was done as described by Quadri et al. (1994), but was resuspended in a final volume of 1 mL TE buffer. An equal volume of chloroform was added to preserve the DNA from bacterial contamination and to remove any residual proteins.

Plasmid and genomic DNA from *B. campestris* was digested with restriction enzymes compatible with the multiple cloning site (MCS) of pUC118 (Vieira and Messing, 1982). Restriction endonucleases from Boehringer-Mannheim (Dorval, Quebec, Canada), Promega (Madison, Wis.; Burlington, Ontario, Canada), and New England Biolabs (Mississauga, Ontario, Canada) were used as recommended by the suppliers. DNA fragments were separated in either 0.65% 40 mM Tris-acetate/1 mM EDTA (TAE) or 0.7% 90 mM Tris-borate/2 mM EDTA (TBE) agarose gels run at 8.5V/cm and blotted by the method of Southern (1975) onto Hybond N (Amersham Corp.) nylon membranes. Molecular weights of fragments were determined by multiple regression analysis based on mobility standards of EcoRI-HindIII digests of bacteriophage lambda (Promega).

For colony blots, Hybond N membrane was placed on top of the colonies, lifted off the plate, incubated for 6 to 8 h on a new LB-ampicillin plate, where necessary, to allow growth of the cells, and the colonies were lysed on the membrane in situ.

A degenerate 23-mer oligonucleotide probe, (APO-1; 5'-AAAGATATTGG(ATC)AAAGG(ATC)ATTGG-3') (SEQ ID NO:52) based on residues 8 to 15 of the amino acid sequence, was used to locate the brochocin-C structural gene (brcA) in both Southern and colony blot hybridizations. Oligonucleotides based upon derived nucleotide sequences were synthesized as needed (Department of Biological Sciences, University of Alberta, Edmonton, AB) on an Applied Biosystems 391 PCR Mate synthesizer, quantified, and used for hybridizations or as primers for nucleotide sequencing without further purification. DNA probes were radioactively end-labelled with [$\gamma^{32}$P]ATP (Amersham) with T4 polynucleotide kinase (PNK; Promega) or nonradioactively by random-primed labelling with digoxigenin-dUTP (Boehringer-Mannheim). A reaction volume of 10 mL of the labelled oligonucleotide mixture (6 mL distilled water, 1 mL 10× PNK buffer, 1 mL [1 pmol] APO-1 probe, 1 mL PNK, 1 mL [γ$^{32}$P]ATP) was added for every 3 mL of hybridization solution. The mixture was purified through a Sephadex G50 column to remove unincorporated ATP or added directly to the hybridization solution. Hybridizations were done at 37° C. overnight in hybridization solution containing 6×SSPE buffer, 5×Denhardt's Reagent (Sambrook et al., 1989) and 0.5% (v/v) SDS. After hybridization, two washes were done sequentially (25° C. for 25 min, 39° C. for 15 min) in 2×SSPE buffer, 0.1% SDS. Where necessary, probes were stripped off membranes by washing at 95° C. for 2 min in 0.5% SDS and rehybridized. Autoradiograms were exposed 24 to 48 h before developing in a Fuji film processor.

Isolation of small-scale plasmid DNA from *E. coli* strains was performed by the lysis by boiling method and large-scale DNA preparation by alkaline lysis (Sambrook et al., 1989). Large-scale plasmid DNA was purified by equilibrium centrifugation at 49 000 rpm (Ti 70.1 rotor) for 20 h in a CsCl-ethidium bromide gradient and dialyzed in TE buffer. Cloning of the brcA gene. Genomic DNA was digested to completion with EcoRI. Fragments of 4.2 kb corresponding to the hybridization signal identified with APO-1 were excised from the gel and placed in 6,000 to 8,000 molecular weight cut-off Spectrapor (Los Angeles, Calif.) dialysis tubing. The DNA was electroeluted from the gel and into the tubing by electrophoresis at 200V for 20 min in 0.5% TBE buffer. The DNA was purified by extracting once with phenol/chloroform:isoamyl alcohol (24:1), once with chloroform:isoamyl alcohol, and precipitated with 2 volumes of 95% ethanol and one-tenth volume of 3 M sodium acetate (pH 5.2). The resulting fragments were cloned into the EcoRI site of the MCS in pUC118 using T4 DNA ligase (Promega) at 25° C. for 3 h in ligation buffer without polyethylene glycol and dithiothreitol. Colonies were screened by α-complementation (Vieira and Messing, 1982). Colony blots were done to discriminate the white colonies for the correct DNA insert. Small-scale plasmid isolations were done on presumptive positive clones and the plasmids were digested with TaqI. The clones were grouped into classes based on similarities in their restriction patterns. Clones were digested with EcoRI, blotted by the method of Southern (1975), and hybridized with APO-1 to confirm the presence of the brcA gene. The plasmid identified to carry the correct 4.2 kb insert in pUC118 was named pAP7.4. A smaller PstI fragment of 1.4 kb was further identified from this plasmid to hybridize to APO-1 and this was subcloned into pUC118 (Pap4.6).

Nucleotide sequencing of plasmid DNA: The plasmid pAP4.6 served as the initial template DNA for nucleotide sequencing by Taq DyeDeoxy Cycle sequencing on an Applied Biosystems 373A sequencer using the universal forward and reverse primers of pUC118. Site-specific 18-mer primers based on newly sequenced DNA were synthesized for further sequencing. The recombinant plasmid, pAP7.4, was used as the template DNA in subsequent sequencing runs to deduce the complete sequence of the structural gene (brcA), the regions flanking the structural gene, and for sequencing of the complementary strand.

Heterologous and homologous expression studies of brochocin-C. The 4.2 kb insert in pAP7.4 was subcloned into the EcoRI site of the shuttle vector pGKV210 to create the recombinant plasmid pAP8.6. This plasmid was subsequently used to transform selected strains by electroporation with a Gene-Pulser (Bio-Rad Laboratories Canada Ltd., Mississauga, ON) at 25 mFD and 200 ohms resistance.

TABLE 9

Inhibitory spectrum of *Brochothrix campestris* ATCC 43754 determined by direct and deferred antagonism on APT agar

| Indicator | Direct | Deferred |
|---|---|---|
| *Bacillus macerans* ATCC 7048 | ƒƒ | ƒƒ |
| *B. cereus* ATCC 14579 | ++ | +++ |
| *Brochothrix campestris* ATCC 43754 | ƒƒ | ƒƒ |
| *B. thermosphacta* B1 | ++ | ++++ |
| *B. thermosphacta* B2 | ++ | ++++ |
| *B. thermosphacta* B3 | ++ | ++++ |
| *B. thermosphacta* B4 | ++ | ++++ |
| *B. thermosphacta* B5 | ++ | ++++ |
| *B. thermosphacta* B7 | ++ | ++++ |
| *B. thermosphacta* B8 | ++ | ++++ |
| *B. thermosphacta* B9 | ++ | ++++ |
| *B. thermosphacta* B10 | ++ | ++++ |
| *B. thermosphacta* B11 | ++ | ++++ |
| *B. thermosphacta* B12 | + | ++++ |
| *B. thermosphacta* B13 | ++ | ++++ |
| *B. thermosphacta* B14 | + | ++++ |
| *B. thermosphacta* B15 | ++ | ++++ |
| *B. thermosphacta* B16 | + | ++++ |
| *B. thermosphacta* L90 | + | ++++ |
| *B. thermosphacta* NF4 | ++ | ++++ |
| *B. thermosphacta* C420 | + | ++++ |
| *B. thermosphacta* I41 | ++ | +++ |
| *Carnobacterium piscicola* LV17 | ++++ | ++++ |
| *C. piscicola* LV17A | ++++ | ++++ |
| *C. piscicola* LV17B | ++++ | ++++ |
| *C. piscicola* LV17C | ++++ | ++++ |
| *C. piscicola* C2/8B | ++++ | ++++ |
| *C. piscicola* C2/8A | ++++ | ++++ |
| *C. piscicola* UAL26 | +++ | ++++ |
| *C. piscicola* UAL26/8A | +++ | ++++ |
| *C. piscicola* UAL26/8B | ++++ | ++++ |
| *C. divergens* LV13 | +++ | ++++ |
| *C. divergens* 9/8A | +++ | ++++ |
| *C. divergens* 9/8B | +++ | ++++ |
| *Clostridium bifermentans* ATCC19299 | +++ | ++++ |
| *C. butyricum* ATCC 8260 | ND | +++ |
| *C. pasteurianum* ATCC 6013 | ND | +++ |
| *Enterococcus faecalis* ATCC 19433 | +++ | ++++ |
| *E. faecalis* ATCC 7080 | +++ | +++ |
| *E. faecium* ATCC 19434 | +++ | ++++ |
| *E. durans* ATCC 11576 | +++ | ++++ |
| *Lactobacillus sake* Lb706 | +++ | ++++ |
| *L. plantarum* ATCC 4008 | ƒƒ | ƒƒ |
| *Lactococcus lactis* ATCC 11454 | ƒƒ | + |
| *L. lactis* UAL 245 | + | + |
| *L. lactis* UAL 276 | ND | + |
| *Leuconostoc gelidum* UAL 187 | ++ | +++ |
| *L. gelidum* UAL 187.13 | + | ++ |
| *L. gelidum* UAL 187.22 | ++ | +++ |
| *L. mesenteroides* ATCC 23386 | ƒƒ | ƒƒ |
| *L. mesenteroides* Y105 | ƒƒ | ++ |
| *Listeria innocua* ATCC 33090 | ++ | +++ |
| *L. monocytogenes* Scott A | +++ | ++++ |
| *L. monocytogenes* UAL 42 | ++ | +++ |
| *L. monocytogenes* ATCC 15313 | + | ++ |
| *Pediococcus acidilactici* ATCC 8042 | + | ++ |
| *Staphylococcus aureus* S6 | ++ | ++ |
| *S. aureus* S13 | ++++ | ++++ |

++++ = zone of inhibition >20 mm
+++ = zone of inhibition 15 to 19 mm
++ = zone of inhibition 10 to 14 mm
+ = zone of inhibition 5 to 9 mm
ƒ = no inhibition zone
ND = not determined Example 7

Novel Bacteriocin Nucleotide and Amino Acid Sequences (Enterocin 900)

*Enterococcus faecium* 900 produces a chromosomally mediated broad spectrum bacteriocin. The forward operon is referred to as SEQ ID NO:28. The bacteriocin consists of 71 amino acids herein referred to as SEQ ID NO:30 and its nucleotide sequence is herein referred to as SEQ ID NO:29. This bacteriocin has activity against other strains of Enterococcus species as well as many other organisms as indicated in Tables 3 and 4.

Purification of Enterocin 900. For purification of the *Enterococcus faecium* BFE 900 bacteriocin the culture was grown in 2.5 l APT broth for 18 h at 30° C. The culture was was heated at 70° C. for 35 min to inactivate proteases and centrifuged at 10 000 rpm for 40 min. The supernatant was termed fraction I. Fraction I (2.5 l) was loaded onto an amberlite XAD-8 (Pharmacia) hydrophobic interaction chromatography column and the column was washed with 3 l of 0.05% trifluoroacetic acid (TFA), and 2 l of 20% ethanol (EtOH)+0.05% TFA. Bacteriocin was eluted with 2 l of 40% EtOH+0.05% TFA. The pH of the eluate was adjusted to pH 5.0 and the eluate was reduced to 47 ml at 37° C. in a rotary evaporator under vacuum. The resulting fraction (fraction II) was pH adjusted (pH 5.0) and loaded loaded onto a carboxymethyl-cellulose CM22 (Whatman Biochemicals, Maidstone, Kent, England) cation exchange column (34 cm, 1.3 cm I.D.) that was pre-equilibrated with 20 mM sodium acetate buffer pH 5.0 (SAB). The column was washed with 100 ml SAB and 60 ml volumes of SAB with 40, 80, and 120 mM NaCl added. Bacteriocin was eluted with 60 ml SAB with 200 mM NaCl added. The bacteriocin containing eluate was loaded onto a Sep Pak C18 reverse phase column (Waters) which was pre-equilibrated according to manufacturers instructions. The column was washed with 20 ml of distilled water and 10 ml of 40% ethanol. Bacteriocin was eluted with 10 ml of 70% ethanol, frozen overnight at −80° C. and subsequently freeze dried. The freeze dried protein was resuspended in 1.5 ml 0.05% TFA (fraction III) and purified using a Beckman System Gold HPLC. For HPLC purification 100 μl aliquots were applied to a $C_{18}$ reverse phase column (Waters Delta-Pak; 8×100 mm; 15 μm particle size; 3000 (30 nm) pore size; flow rate 1.0 ml/min; mobile phase, 0.05% TFA [A] and 95% ethanol in 0.05% TFA [B]). Bacteriocin was eluted by a gradient method (first 40% to 60% solvent B in 7 min and then 60 to 70% solvent B in 10 min). Fractions were monitored for $A_{218}$ and for activity against the indicator strain. The puritiy of the fraction was determined by tricine gel electrophoresis.

Bacteriocin activity of fractions I, II and III was determined by the critical dilution method described in section 2.1.1, using *Lactobacillus sake* DSM 20017 as indicator organism. Protein concentration of these fractions was determined by the dye binding method of Bradford (Bradford, 1976).

Protein sequencing. Protein sequencing was performed by Edman degradation on an automated sequencer. To determine whether the structural enterocin gene indeed resides on the chromosome an oligonucleotide probe based on the first 11 ahino acids of enterocin 900 was constructed and used to probe chromosomal DNA. The probe CF01 consisted of the following 32 nucleotides: GAA AAT GAT CAT (C/A)G(T/A) ATG CC(T/A) AAT GAA CT(T/A) AA (Seq. ID No. 54) and had a $T_M$ of 82° C. Chromosomal DNA was isolated by the methods of Quadri et al., 1994 and digested with the restriction enzymes EcoRI, PstI and HindIII before running on a 0.7% agarose gel. DNA was transferred to hybond membrane by Southern blotting as described in Sambrook et al. 1989. The probe CF01 was end labelled with $^{32}$P-[γ-ATP] and hybridized to the DNA as described by Sambrook et al. 1989. The probe hybridized to a 2.2 kbp HindIII fragment and a 6.5 kbp EcoRI/PstI fragment.

The 2.2kbp HindIII fragment was cloned into pUC118 contained in *E. coli* DH5α and sequenced. The nucleotide sequence analysis was performed by sequencing the DNA in both orientations by dideoxy-chain method of Sanger and associates (1977). DNA was sequenced by Taq Dye Deoxy Cycle sequencing on an Applied Biosystems DNA sequencer (Applied Biosystem, Foster City, Calif.).

Example 8

A Food-grade Plasmid pCD3.4

Large scale plasmid preparation from *C. divergens* LV13 was done as described for *C. piscicola* LV17A (Worobo et al., 1994). Other DNA manipulations were based on those described by Sambrook et al. (1989). Pfu DNA polymerase (Stratagene, LaJolla, Calif.), restriction endonucleases and T4 DNA ligase were obtained from Promega (Madison, Wis.), Bethesda Research Laboratories (Burlington, ON), Boehringer Mannheim (Dorval, PQ), New England Biolabs (Mississauga, ON) and used according to the suppliers' recommended procedures. Step-wise deletion derivatives for sequencing were prepared using the Erase-a-Base® system (Promega) and DNA fragment recovery was done using Geneclean II® (Bio 101 Inc., LaJolla, Calif.). Oligonucleotides prepared as sequencing and PCR primers were synthesized on an Applied Biosystems (model 391) PCR Mate synthesizer. Double stranded DNA was sequenced by Taq DyeDeoxy Cycle sequencing on an Applied Biosystems (model 373A) sequencer.

The nucleotide sequence is herein referred to as SEQ ID NO:14. From the nucleotide sequence and the restriction maps (FIG. 8) one of ordinary skill in the art can identify a variety of suitable locations for inserting other genes without undue experimentation. This plasmid can be use to insert genes for use in probiotics, meat, milk products, food or food products. The bacteriocin Divergicin A was derived from this plasmid (Worobo et al. 1995) and the signal peptide nucleotide sequence is used in other sections of this application is referred to as SEQ ID NO:19 and the corresponding amino acid sequence is SEQ ID NO:20.

Example 9

Methods for Testing Organisms for Preservation of Meat and Organisms that will Preserve Meat Bacterial cultures and identification of *Lb. sake* 1218. The lactic acid bacteria used in this study are listed in Table 1. *Lb. sake* 1218 is a sulfide-producing LAB isolated from modified atmosphere packaged pork stored at −1° C. (McMullen and Stiles, 1993). The strain was initially identified by McMullen and Stiles (1993) using standard techniques (Montel et al., 1991; Schillinger and Lucke, 1987), and its identity was confirmed in this study with the following biochemical and cultural tests: production of slime from sucrose; ability to grow on acetate agar (Cavett, 1963); reduction of tetrazolium (Wilkinson and Jones, 1977); final pH in La-broth (Reuter, 1970; Shaw and Harding, 1984); presence or absence of meso-diaminopimelic acid (Kandler and Weiss, 1986); sugar-fermentation pattern (Shaw and Harding, 1985); and lactic acid isomer determination by an enzymatic-UV method (Boehringer Mannheim, 1987). *Lb. sake* 1218 was tested for bacteriocinogenic activity against all of the *Leuc. gelidum* strains by direct and deferred inhibition tests (Ahn and Stiles, 1990a; Ahn and Stiles, 1990b).

Inhibition of *Lb. sake* 1218 by *Leuc. gelidum* strains in APT broth. Growth rates of *Leuc. gelidum* UAL187 and its variants were determined in pure culture at 2 and 25° C. in APT broth (Difco Laboratories Inc., Detroit, Mich.) containing 2% glucose, or in modified APT broth (mAPT) made according to Difco (Difco Manual, 1984) but containing 0.05 or 0.1% glucose inoculated at 4.2 to 4.3 log CFU/ml. Initial pH of APT broth was adjusted to 5.6 or 6.5. Competitive growth studies of *Leuc. gelidum* UAL187, UAL187-22 or UAL187-13 with *Lb. sake* 1218 were done in mAPT containing 0.1% glucose and initial pH adjusted to 5.6.

Inocula for all experiments were grown in APT broth at 25° C. for 18 h. Cells were washed three times by centrifugation at 16,000×g, washed with sterile, 0.1% peptone water and resuspended in peptone water at the desired cell density. Samples for bacterial enumeration were diluted in 0.1% peptone water and surface streaked onto M5 agar, consisting of tryptone (10 g/l), yeast extract (5 g/l), fructose (2.5 g/l), $KH_2PO_4$ (2.5 g/l), L-cysteine HCl (0.5 g/l), $MgSO_4.7H_2O$ (0.2 g/l), $MnSO_4.H_2O$ (0.05 g/l), calcium pantothenate (0.01 g/l), agar (20 g/l), Tween 80 (1 ml/l), and bromocresol green (0.1 g in 30 ml of 0.01 N NaOH) (20 ml/l) (Zunfiga et al., 1993). This medium differentiated the heterofermentative *Leuc. gelidum* colonies (white color) from homofermentative *Lb. sake* 1218 colonies (blue color). Representative colonies were checked by their phenotypic characteristics to determine the reliability of the differentiation (see below). MRS (Difco)-sorbic acid agar (Anon, 1987) was used for selective enumeration of *Lb. sake* 1218. Plates were incubated at 25° C. for 3 days. pH was determined in all samples. Antimicrobial activity of leucocin A in the supernatant was assayed by the spot-on-lawn method (Ahn and Stiles, 1990a; Ahn and Stiles, 1990b) with *Carnobacterium divergens* LV13 as the indicator strain. All experiments were done in duplicate.

Inoculation of beef samples. Sterile, lean slices of beef (surface area 20 $cm^2$) were excised aseptically from normal pH longissimus dorsi muscle as described by Greer and Jones, 1991. Beef slices were suspended from sterile clips and immersed for 15 sec in a bacterial suspension containing $10^5$ CFU/ml for *Leuc. gelidum* and $10^3$ CFU/ml for *Lb. sake*, and allowed to air dry at 25° C. for 15 min. This gave an inoculum of approximately $10^4$ CFU $cm^{-2}$ for *Leuc. gelidum* and $10^2$ CFU $cm^{-2}$ for *Lb. sake*. An equal number of beef slices was immersed in sterile, 0.1% peptone water for use as controls.

Beef storage. Three inoculated beef slices from each sample were placed in sterile Stomacher bags (Seward Medical, U.K.), enclosed in gas impermeable foil laminate bags (Printpac-UEB, Auckland, New Zealand) and vacuum packaged using a Captron III Packaging is System (RMF, Grandview, Mo.). Vacuum packaged beef samples were stored at 2° C. for 8 weeks and samples were removed for analysis after 0, 1, 2, 3, 4, 4.5, 5, 6 and 8 weeks of storage. Three or four independent trials were done for microbiological content and sensory analysis of each combination of bacterial inocula, except for meat inoculated with pure cultures of *Leuc. gelidum* UAL187, UAL187-22 and UAL187-13, for which only one trial was done.

Bacterial sampling and determination of antimicrobial activity on meat. At each sampling time, three beef slices from one package were homogenized separately in a Colworth Stomacher 400 (Baxter Diagnostics Corp., Canlab Division, Edmonton, AB Canada) in 90 ml of sterile 0.1% peptone water. Samples were diluted and surface plated onto MS or MRS-sorbic acid agar and incubated at 25° C. for 3 days. The reliability of detection of the Leuconostoc strain was checked by the ability to produce slime on APT agar containing 2% sucrose. An average of 8 colonies of each of the *Leuc. gelidum* variants was picked from M5 agar plates from meat samples analyzed after 3 or 8 weeks of storage. These colonies were grown in APT broth, and examined for purity by carbohydrate fermentation patterns (Shaw and Harding, 1985), some were also examined for plasmid profiles (Ahn and Stiles, 1990b) and for bacteriocin production by overlayering with the indicator strain. After enumeration, M5 plates were overlayered with soft APT agar (0.75% agar) containing 1% of an overnight culture of *C. divergens* LV13 or *Lb. sake* 1218 to determine antimicrobial activity by the deferred inhibition test.

Production of leucocin A during growth of the producer strain on beef was determined by a modification of the procedure described by Ruiz-Barba et al. (Ruiz-Barba et al., 1994). One beef slice was homogenized in 90 ml of 0.1% peptone water, heated in a boiling water bath for 15 min, cooled rapidly on ice and Ecentrifuged at 8,000×g for 15 min. Ammonium sulfate (Fisher Scientific; Fair Lawn, N.J.) was added to 70% saturation, stirred at 4° C. overnight and centrifuged at 20,000×g for 1 h at 0.5° C. The precipitate was resuspended in 1.5 ml of sodium phosphate buffer (50 mM, pH 7.0) and activity was determined by the spot-on-lawn method (Ahn and Stiles, 1990a; Ahn and Stiles, 1990b) using *C. divergens* LV13 as indicator. The presence of bacteriocin was confirmed by adding 10 μl of Pronase E (1 mg/ml; Sigma Chemical Co., St. Louis, Mo.) to appropriate samples of supernatant.

Sensitivity of *Lb. sake* 1218 to leucocin A. After 8 weeks of storage under vacuum at 2° C., one of the beef slices from each inoculum type was homogenized in 90 ml of sterile, 0.1% peptone water. From each sample, 75 μl of liquid was withdrawn and mixed with 7.5 ml of "soft" MRS-sorbic acid agar (0.75% agar) and plated on MRS-sorbic acid agar (1.5% agar) for selective growth of *Lb. sake* 1218. Supernatants of APT broth cultures of *Leuc. gelidum* UAL187 or UAL187-13 grown at 25° C. for 18 h were adjusted to pH 6.5 with 1 N NaOH and heated at 65° C. for 30 min. From these preparations, 20 μl of appropriate two-fold dilutions was spotted onto the *Lb. sake* 1218 indicator lawns to be tested for sensitivity to leucocin A. Plates were incubated anaerobically at 25° C. overnight and observed for zones of inhibition.

Sensory assessment of beef samples. Qualitative analysis of odor acceptability, based on detection of sulfur odors in vacuum packed beef samples, was done as described by McMullen and Stiles, 1994. An experienced five-member panel was used. Each packaged sample containing three slices of beef was filled with 200 ml helium, and 5 ml of headspace gas was withdrawn for sensory analysis through a "sticky nickel" (Mocon Modern Controls Inc., Minneapolis, Minn.) sampling port with a gas tight syringe (SGE, Mandel Scientific, Guelph, Ontario) equipped with a button lock. Acceptability was judged by absence or presence of sulfur odor. A sample was deemed spoiled if 50% or more of the panelists rejected the sample because of a sulfur odor.

Characterization and identification of *Lb. sake* 1218. The Gram-positive, rod-shaped, catalase- and oxidase-negative strain 1218 was classified as *Lb. sake* based on its following characteristics: no gas from glucose; growth on acetate agar; degradation of arginine; unable to reduce tetrazolium; absence of meso-diaminopimelic acid in the cell wall; production of D- and L-lactic acid isomers; final pH<4.15 in La-broth; and the following carbohydrate fermentation pattern: amygdalin (−), arabinose (+), cellobiose (−), fructose (+), glucose (+), inulin (−), inositol (−), lactose (−), maltose (−), mannitol (−), mannose (+), melezitose (−), melibiose (+), raffinose (−), ribose (+), salicin (−) and sucrose (+). No acids were produced from glycerol or pyruvate. The organism grew in the presence of 6.5% NaCl but not at 45° C. Preliminary experiments showed that *Lb. sake* 1218 produced strong sulfurous off odors when inoculated onto vacuum packaged beef, but not on beef stored under aerobic conditions. *Lb. sake* 1218 was not found to be bacteriocinogenic against any of the *Leuc. gelidum* variants when tested by deferred and spot-on-lawn techniques. MS agar did not give a reliable differentiation between the test strains. More reliable information was obtained from the counts on MRS-sorbic acid agar 45 to enumerate *Lb. sake* 1218.

Inhibition of *Lb. sake* 1218 by *Leuc. gelidum* strains in APT broth. At 25° C. the three isogenic variants of *Leuc. gelidum* UAL187 had identical doubling times of 3.85 h when grown as pure cultures or in combination with *Lb. sake* 1218. In MAPT with initial glucose concentrations of 0.05, 0.1 or 2% or initial pH values of 5.6 or 6.5 of the growth medium did not affect the growth rate of the *Leuc. gelidum* variants. At 2° C. the initial doubling times for *Leuc. gelidum* UAL187, UAL187-13 and UAL187-22 were similar, averaging 1.75 days; but after four to eight days of incubation the doubling time of *Leuc. gelidum* UAL187-22 increased to 3.15 days. This change in growth rate could not be attributed to glucose concentration or pH of the growth medium or whether *Leuc. gelidum* UAL187-22 was grown as pure culture or together with *Lb. sake* 1218.

*Lb. sake* 1218 grown in APT broth in mixed culture with *Leuc. gelidum* UAL187 or UAL187-22 at 25° C. was inhibited at the time (17 h) that antimicrobial activity was detected in the supernatant (FIG. 9). Growth of *Lb. sake* 1218 resumed after 21 h, coinciding with a decrease in antimicrobial activity, and reached a population of approximately $10^7$ CFU/ml after extended incubation of 100 h at 25° C. (FIG. 9). *Lb. sake* 1218 grew rapidly in pure culture or in mixed culture with *Leuc. gelidum* UAL187-13 (FIG. 9). Antimicrobial activity was not detected in these cultures.

Figure 10:
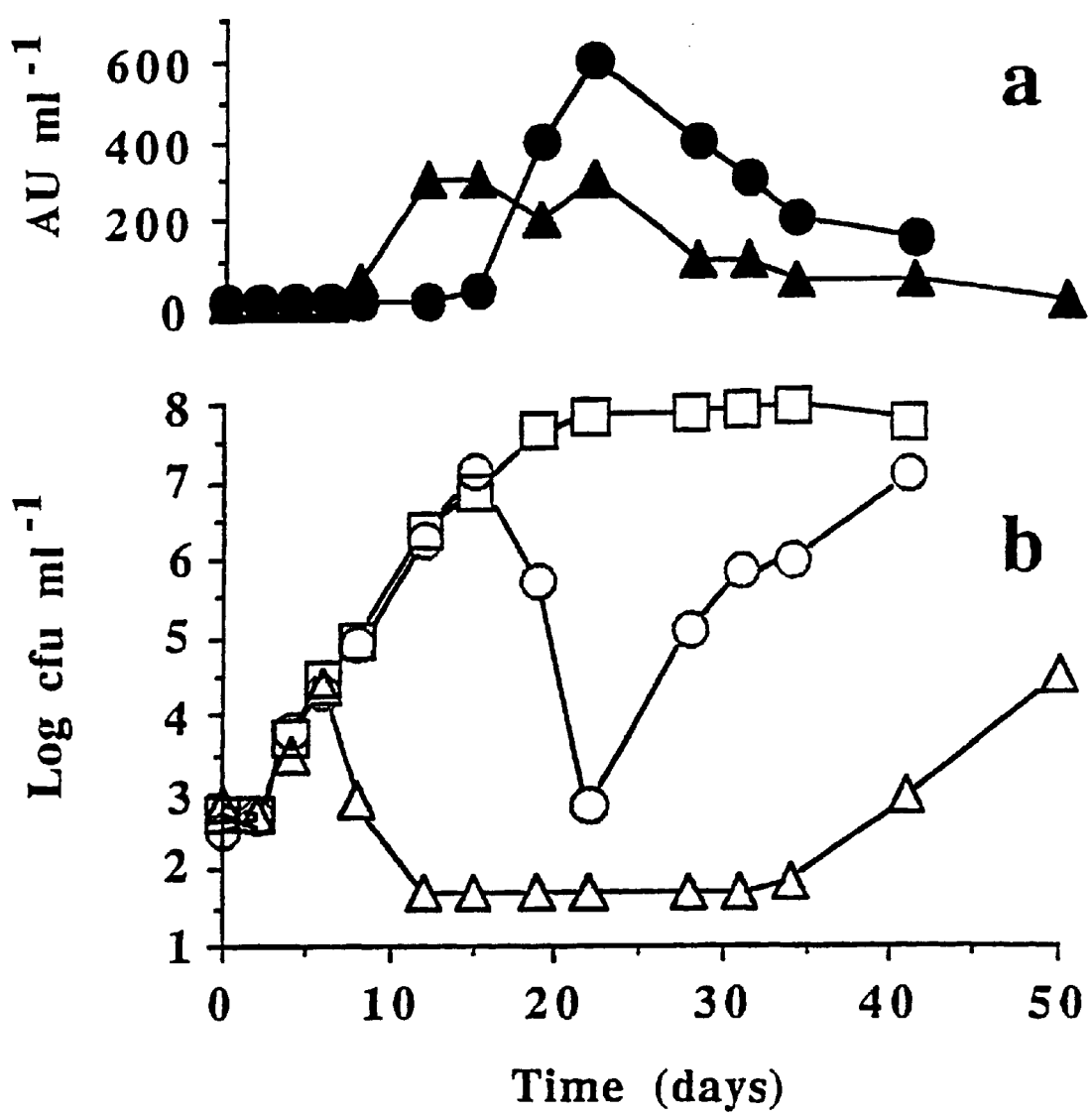
FIG. 10. Bacteriocin activity (a) and growth (b) of *Lactobacillus sake* 1218 in mixed culture with variants of *Leuconostoc gelidum* at 2° C. in mAPT with 0.1% glucose and the initial pH adjusted to 5.6. See FIG. 9 for definitions of symbols.

Growth of *Lb. sake* 1218 in APT broth at 2° C. was inhibited in mixed culture with *Leuc. gelidum* UAL187 after 8 d of incubation, coinciding with the time that antimicrobial activity was first detected in the supernatant (FIG. 10). The cell density of *Lb. sake* 1218 decreased to the minimum detection limit after 12 d of incubation, but growth resumed after approximately 30 to 35 d of storage (FIG. 10). *Lb. sake* 1218 grew rapidly at 2° C. in pure culture and in mixed culture with *Leuc. gelidum* UAL187-13 (FIG. 10). Antimicrobial activity was not detected in these cultures. *Lb. sake* 1218 in mixed culture with *Leuc. gelidum* UAL187-22 grew actively for the first 15 d of incubation; after which a rapid decline in cell counts of *Lb. sake* 1218 was observed, coinciding with the detection of antimicrobial activity (FIG. 10). After 22 days of incubation there was a loss of antimicrobial activity and *Lb. sake* 1218 resumed its growth. pH did not change more than 0.2 units from the initial value in any of the experiments done with MAPT.

Figure 11:
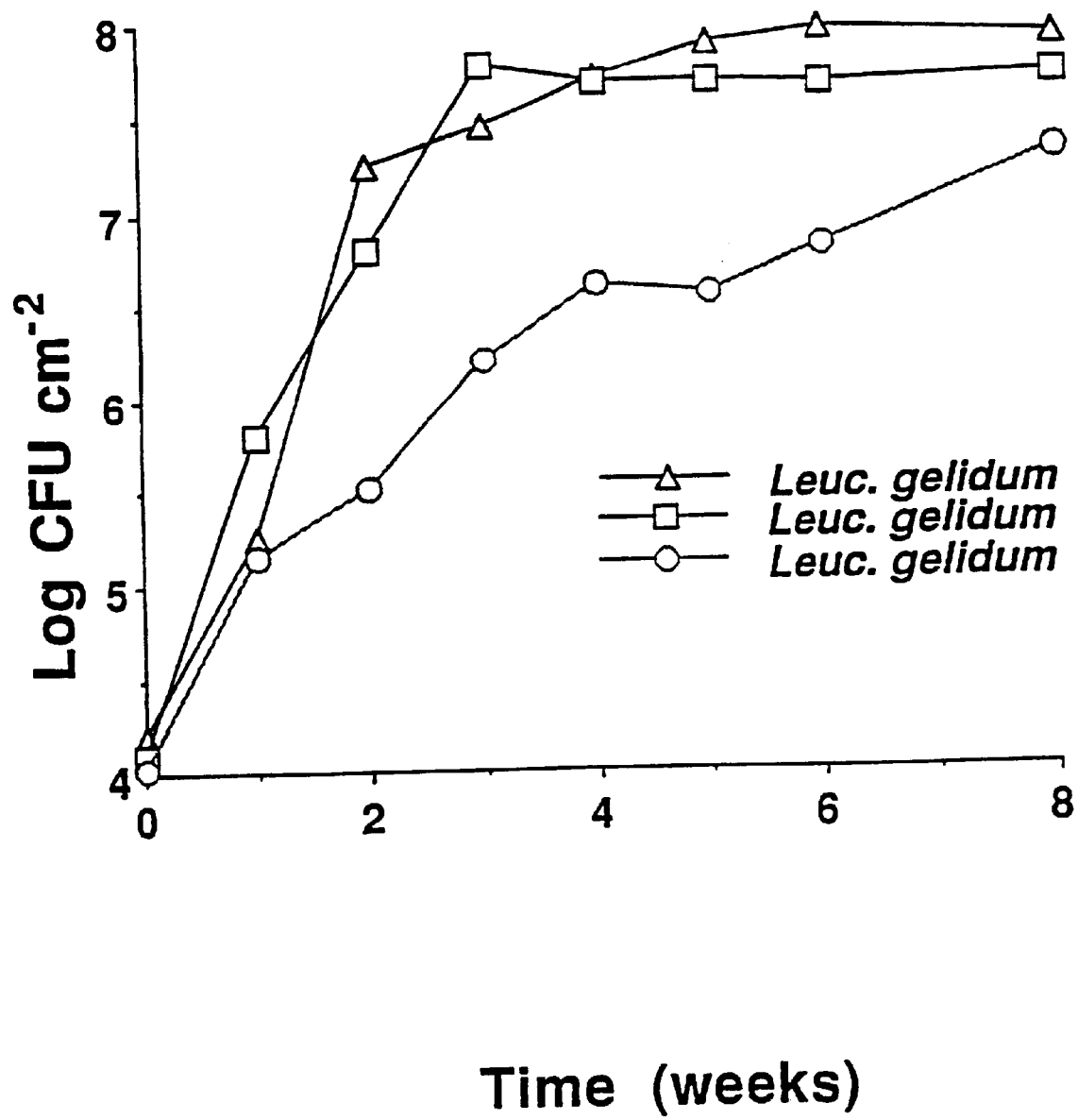
FIG. 11. $Log_{10}$ CFU of variants of *L. gelidum* grown in mixed culture with *L. sake* 1218 per square centimeter of vacuum-packaged beef stored at 2° C. (Δ), *L. gelidum* UAL187; (□), UAL-187-13; (○), UAL187-22. The data represent the means of three trials.
Figure 12:
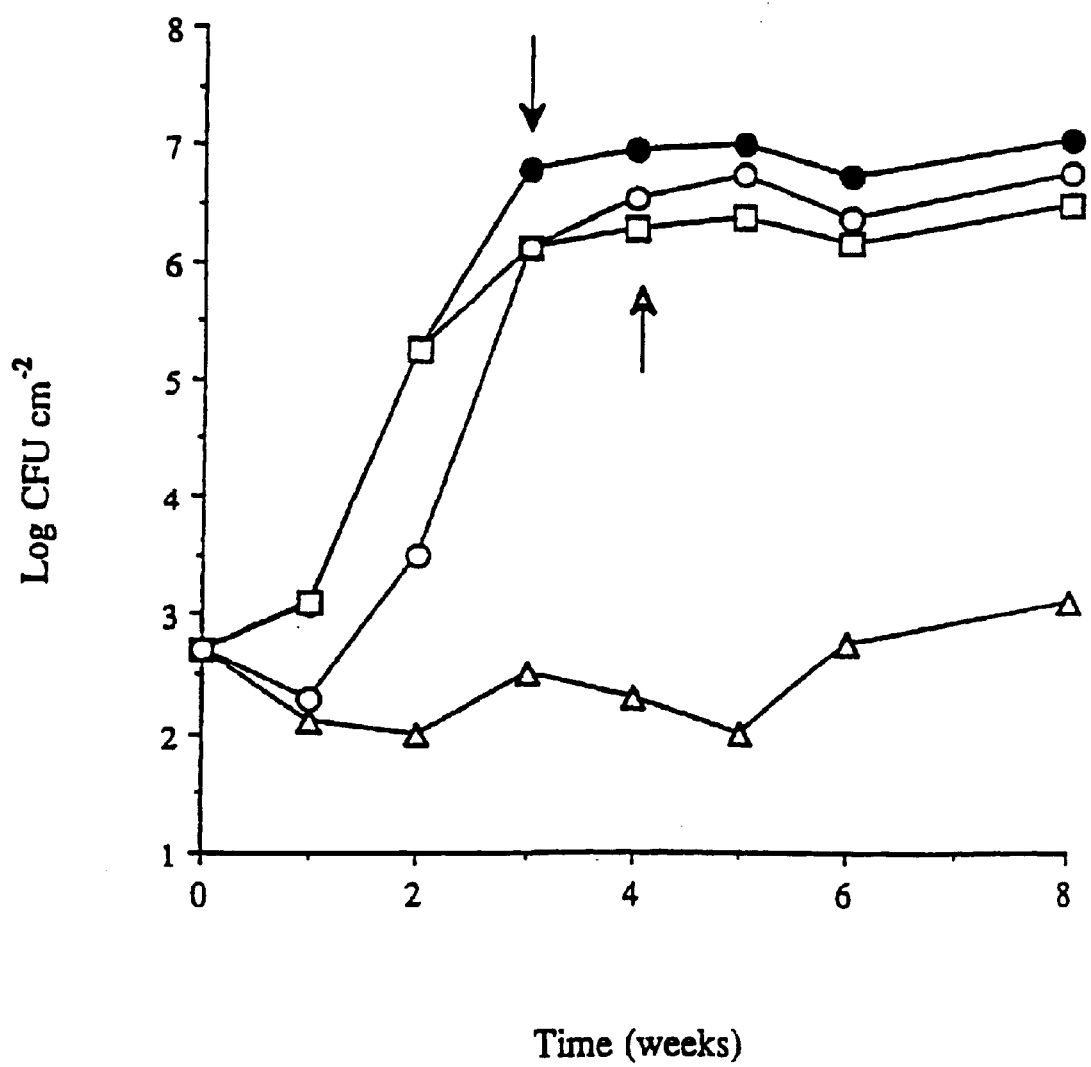
FIG. 12. $Log_{10}$ CFU of *L. sake* 1218 showing growth and survival in mixed culture with variants of *L. gelidum* per square centimeter of vacuum-packaged beef stored at 2° C. (●), *L. sake* 1218 alone; (Δ), *L. sake* with *L. gelidum* UAL187; (□), *L. sake* with UAL187-13; (○), *L. sake* with UAL187-22. The solid arrow indicates the sampling time at which a sulfide odor was first detected in samples inoculated with *L. sake* 1218; the open arrow indicates the sampling time at which a sulfide odor was first detected in samples inoculated with *L. sake* 1218 and *L. gelidum* UAL187-13 or UAL187-22. The data represent the means of three trials.
Figure 13:
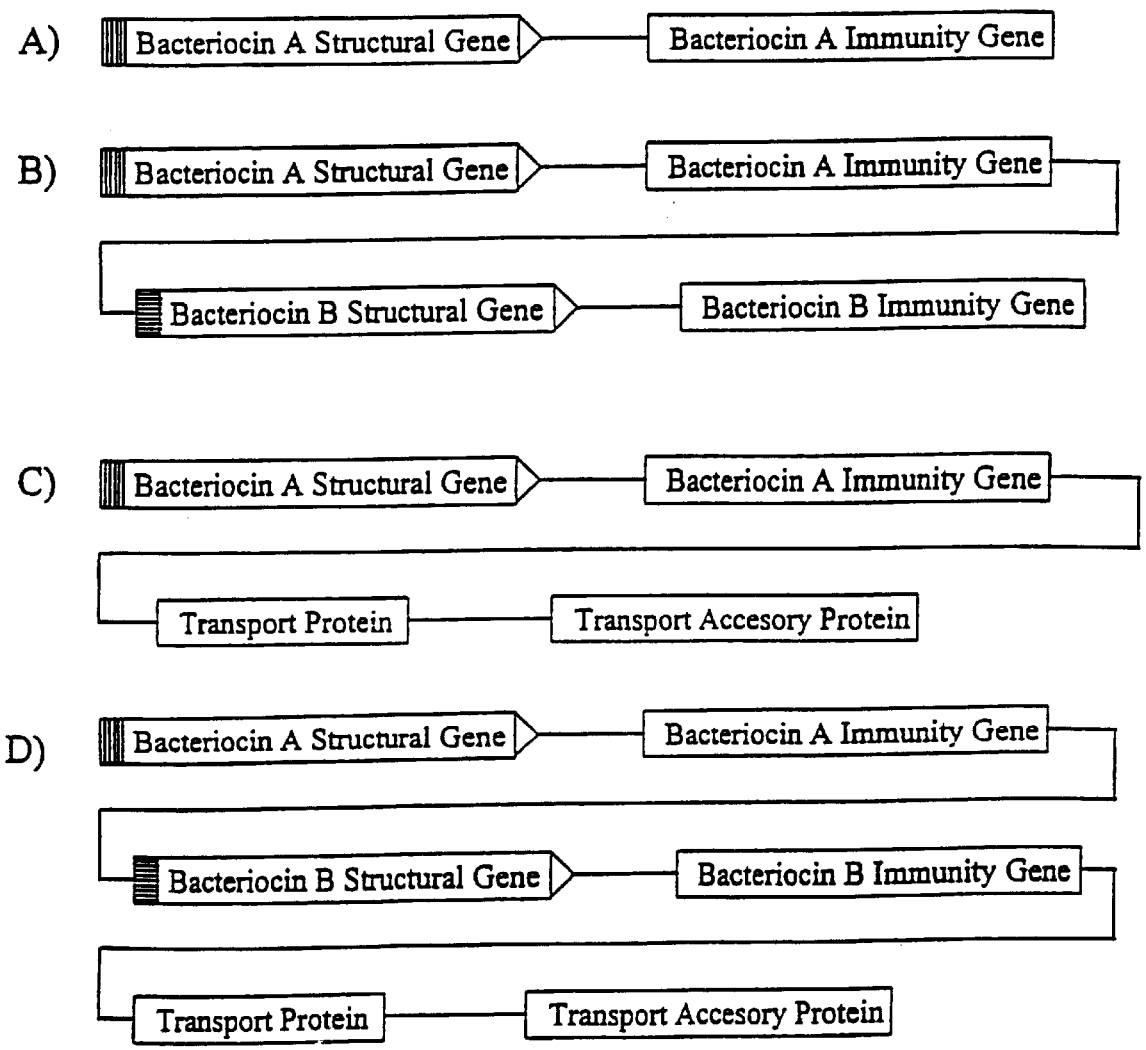
FIG. 13. The method of use of this invention is illustrated by the following schematics A-O. The signal peptide gene or leader peptide gene(s) is illustrated as vertical or horizontal hatching. As schematic A indicates, a signal or leader peptide is attached to a bacteriocin gene devoid of its natural leader peptide or signal peptide gene. A plasmid can contain a single bacteriocin with its immunity gene. The spacing between the structural gene and the immunity gene is not important and the immunity gene does not necessarily have to follow the structural gene providing the immunity gene is also expressed and prevents the bacteriocin from killing its host. As schematic B illustrates a plasmid can contain more than one copy of a bacteriocin or more than one type of bacteriocin. The vector can contain many bacteriocins. In scheme B, the leader or signal peptide genes can be different or the same providing that leader peptide or signal peptide is compatible with the transport system in the cell. If the transport system is not compatible with the leader then a transport system can also be introduced into the vector or plasmid (C) or (D). For multiple bacteriocins or proteins each structural gene needs to be attached to a leader or signal peptide.
Figure 14:
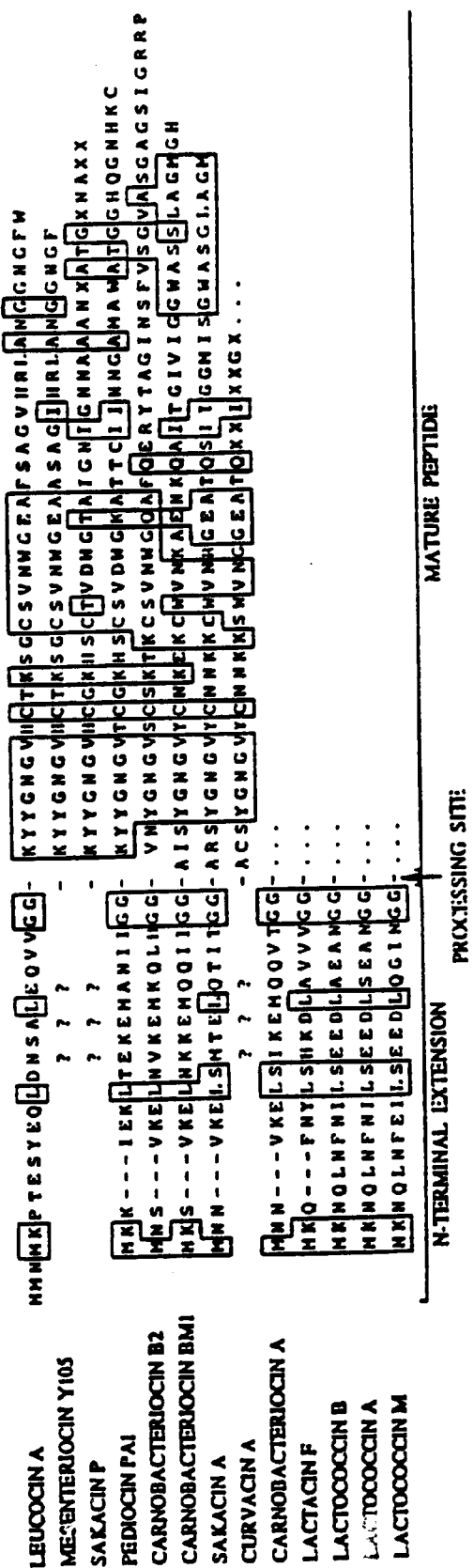
FIG. 14. Examples of other leader or signal peptides that could be used in this invention and names of other bacteriocins that could utilize these signal peptides or other signal or leader peptides included herein. The best host for a vector containing a bacteriocin gene with a leader or signal peptide gene attached is the organism from which the leader peptide was derived but other closely related organisms frequently also work with particular leader peptides. Additional information about these bacteriocins and leader peptides can be obtained from Quadri and associates (1994) or references therein. Comparisons of the sequence similarities is also provides. The vertical arrow indicates the cleavage site in the prebacteriocins.

Growth of bacteria and detection of bacteriocin on vacuum packaged beef. The data shown in FIG. 11 illustrate the growth of the three isogenic strains of *Leuc. gelidum* UAL187 inoculated as pure cultures or co-inoculated with *Lb. sake* 1218 on beef stored under vacuum at 2° C. *Leuc. gelidum* UAL187 and UAL187-13 again exhibited identical growth rates, while *Leuc. gelidum* UAL187-22 grew at a considerably slower rate. Growth and survival of *Lb. sake* 1218 alone or in mixed culture with the isogenic variants of *Leuc. gelidum* is shown in FIG. 12. *Lb. sake* 1218 grew rapidly as a pure culture on vacuum packaged beef producing a sulfurous odor within three weeks at 2° C. Pronounced inhibition of *Lb. sake* 1218 was observed in three out of four trials in which *Lb. sake* 1218 was co-inoculated with *Leuc. gelidum* UAL187 on meat. There was a delay of growth for 5 weeks with a 4 log lower count of *Lb. sake* 1218 after 8 weeks of incubation. In a fourth trial, there was a delay of two weeks before initiation of growth of *Lb. sake* 1218 and relatively low maximum count of $10^5$ to $10^6$ log CFU cm$^{-2}$ was observed. These data were not included in the means calculated for FIG. 12. Similar growth of *Lb. sake* 1218 but with approximately one log lower maximum count than in pure culture was observed when *Lb. sake* 1218 was co-inoculated with *Leuc. gelidum* UAL187-13. A slight delay in initiation of growth and a reduction of 0.5 to 1 log units in maximum count was observed when *Lb. sake* 1218 was co-inoculated with *Leuc. gelidum* UAL187-22. Comparison with pure culture studies indicated that growth of *Leuc. gelidum* UAL187 and its isogenic variants was not affected by the presence of *Lb. sake* 1218 in any trial. The identity of each variant of *Leuc. gelidum* was confirmed by comparison of plasmid profiles, carbohydrate fermentation patterns and slime production of colonies isolated after eight weeks of storage from each experiment.

The possibility that *Lb. sake* 1218 developed resistance to leucocin A during the trial with extended growth in the presence of *Leuc. gelidum* UAL187 was tested. Spot-on-lawn tests of isolates of *Lb. sake* 1218 were done after 8 weeks of storage. Results showed that *Lb. sake* 1218 was sensitive to 800 AU ml$^{-1}$ in heat treated supernatant of *Leuc. gelidum* UAL187 grown in APT. The same sensitivity was observed for isolates of *Lb. sake* 1218 grown as pure cultures or in mixed culture with *Leuc. gelidum* UAL187-22 or UAL187-13. Growth of *Lb. sake* 1218 with extended incubation was apparently due to loss of activity of leucocin A rather than development of resistant strains of *Lb. sake* 1218.

Antimicrobial activity that was sensitive to pronase E was demonstrated for extracts prepared from beef samples co-inoculated with *Leuc. gelidum* UAL187 and *Lb. sake* 1218. The antibacterial activity on the meat persisted from two up to eight weeks of storage, but the level of activity was near the lowest detectable limit and activity could not be detected on all samples that were tested. At least half of the trials were positive at each sampling time. Antimicrobial activity was also observed on beef co-inoculated with *Leuc. gelidum* UAL187-22 and *Lb. sake* 1218 after six weeks of storage. No activity was observed for beef co-inoculated with *Leuc. gelidum* UAL187-13 and *Lb. sake* 1218. *Leuc. gelidum* UAL187 and UAL187-22 retained their bacteriocinogenic potential at all storage intervals when tested for antagonistic activity by the deferred inhibition test.

Detection of spoilage of beef samples. *Leuc. gelidum* UAL187 completely inhibited sulfur-mediated spoilage of beef by *Lb. sake* 1218 for up to eight weeks, except in two of four trials, where spoilage was detected in samples taken at 4.5 weeks but not at 6 and 8 weeks of storage at 2° C. Spoilage produced by *Lb. sake* 1218 in the presence or absence of *Leuc. gelidum* UAL187-22 or UAL187-13 was detected within 3 to 4.5 weeks of storage and illustrated by arrows in FIG. 12. No spoilage was detected in beef samples inoculated with pure cultures of *Leuc. gelidum* UAL187, UAL187-22 or UAL187-13 and stored for up to eight weeks under vacuum at 2° C.

Preservation of Pork. Application of modified atmosphere packaging for retail marketing of pork cuts was studied. Experiments were designed to determine: (1) effects of storage conditions on keeping quality and the prevailing microflora on the meat cuts; (2) the potential to access distant markets with retail-ready cuts using this technology; and (3) the effect of inoculation of retail cuts with selected lactic acid bacteria (LAB) on keeping quality and the use of headspace gas analysis to monitor spoilage.

To examine the effects of storage conditions pork loin cuts prepared with two levels of initial bacterial load were packaged in three films of different gas transmission in an atmosphere containing 40% $CO_2$/60% $N_2$ and stored at −1, 4.4 and 10° C. Temperature was the overriding factor influencing storage life. Spoilage at each storage temperature could be attributed to the growth of different groups of bacteria and was influenced by package type. Storage life of pork cuts in packages with low oxygen transmission rates was 5 or 8 weeks at 4.4 or −1° C., respectively. Listeriae were detected as part of the prevalent microflora on samples stored at −1° C., but not on samples stored at 4.4 or 10° C. A total of 162 (30%) of LAB isolated from the meat samples produced inhibitory substances against a range of indicator strains.

Samples for studies to simulate storage conditions to access distant markets with retail-ready cuts of pork were packaged in 100% $CO_2$ in plastic film with extremely low gas transmission and stored at −1.5° C. for three weeks. Reference samples were held at −1.5° C. for the duration of the study. After transfer of samples to 4 and 7° C., samples remained acceptable for retail sale for 2 and 1 weeks, respectively. Appearance of the cuts was the main factor limiting storage life; however, confinement odor became a potential problem for consumer acceptance of the product with extended storage.

Studies of inoculated retail-ready cuts of pork packaged in 100% $CO_2$ and stored at 4° C. revealed that the type of bacteriocinogenic LAB affected the storage life of the meat. Sulphur odors were detected on meats inoculated with *Carnobacterium piscicola* LV17 or *Leuconostoc gelidum* UAL187 but not with *Lactobacillus sake* Lb706 using methods described for beef. Detection of sulfur compounds in the headspace gas at the time that the sensory panel detected off-odors, indicated that monitoring of these compounds is an objective measure of spoilage.

The studies demonstrated that there is good potential to apply modified atmosphere packaging technology to retail cuts of pork. With adequate temperature control, storage life can be extended for weeks beyond what is possible with aerobic packaging.

Assessment of the spoilage potential of selected strains of LAB is imperative before they can be exploited as biopreservatives for achieving a predictable storage life of retail-ready products.

Example 10

Method for Using Bacterocins for Treating Infections

For the treatment of animal or human diseases, purified or partially purified bacteriocins are used for topical application or internal use.

The bacterocins are purified or partially purified by a variety of methods including, without limitation, the methods described herein or those described by Henderson and associates (1992); Hechard and associates (1992); Hasting and associates (1991); Quadri and associates (1993) or Worobo and associates (1994) or may be able to be obtained commercially obtained commercially (Quest; Flavors & Food Ingredients Co., Rochester, N.Y.).

The formulations for delivery are similar to other bacterocins, and one of ordinary skill in the art can determine which formulation to use without undue experimentation. The concentration of bacterocin required for one of these formulations can be determined by comparing units/μg of a known bacterocin to the novel bacteriocin. The concentration of the novel bacteriocin should be set so that the concentration of the novel bacteriocin active units/ml is 0.1 to 10 times the activity of the control.

Example 11

Use of Organisms Containing Bacteriocin Genes to Preserve Food

To prevent food poisoning, milk products lactobacterium containing a Gram-negative bacteriocin (i.e. Colicin V) (these organisms could also contain other bacteriocins) can be added to the product. For yogurt, $10^8$ to $10^9$ lactobacillus bacteria are added to milk. To improve the shelf life of this product (0.01% to 100% of these organisms added could contain the desired plasmid). This same method can be used for protection of cheese but the host bacterium and number of organisms incoluated into the milk is dependent on the type of cheese, one of ordinary skill in the art can determine what type of organism to use.

Example 12

Treatment of Infections or Bacteria Disorders

For intestinal infections such as food poisoning due to particular organism (*E.coli*; Salmonella, etc.), an anti-diarrhea treatment contains $10^6$ to $10^8$ harmless organisms (i.e. lactobacillus strains) in a buffered solution, suitable to be administered orally. The organisms contain a bacteriocin, in a food-grade plasmid, that inhibit the growth of the common diarrhea-causing organisms (i.e. bacteriocins active against gram-negative organisms-Colicin V). These same organisms are also added to a buffered ointment suitable for vaginal administration.

References

Ahn, C., and M. E. Stiles. 1990. Plasmid-associated bacteriocin production by a strain of *Carnobacterium piscicola* from meat. Appl. Environ. Microbiol. 56:2503–2510.

Allison, G. E., Worobo, R. W., Stiles, M. E., and Klaenhammer, T. R. (1995b) Heterologous expression of the lactacin F peptides by *Carnobacterium piscicola* LV17 Appl Environ Microbiol. 61: 1371–1377.

Anon. 1987. de Man, Rogosa and Sharpe agar with sorbic acid (MRS-S agar). Int. J. Food Microbiol. 5:230–232.

Axelsson, L., A. Holck, S.-E. Birkland. T. Aukrust. and H. Blom. 1993. Cloning and nucleotide sequence of a gene from *Lactobacillus sake* Lb706 necessary for sakacin A production and ammunity. Appl. Environ. Microbiol 59:2868–2875.

Axelsson, L., and A. Holck. 1995. The genes involved in production of and immunity to sakacin A, a bacteriocin from *Lactobacillus sake* Lb706. J. Bacteriol. 177:2125–2137.

Barefoot, S. F., and T. R. Klaenhammer (1983). Detection and activity of lactacin B, a bacteriocin produced by *Lactobacillus acidophilus*. Appl. Environ. Microbiol. 45:1808–1815.

Birnboim, H. C., and Doly, J. (1979) A rapid alkaline extraction procedure for screening recombinant plasmid DNA. Nucleic Acids Res 7:1513–1523.

Blight, M. A., and I. B. Holland. (1990) Structure and function of haemolysin B, P-glycoprotein and other members of a novel family of membrane translocators. Mol Microbiol 4: 873–880.

Boehringer Mannheim. 1987. D(–)-Lactate dehydrogenase (D-LDH). Biochemica information, p. 45. Boehringer Mannheim Biochemicals, Indianapolis, Ind.

Borch, E. and Agerhem, H. (1992) Chemical, microbial and sensory changes during the anaerobic cold storage of beef inoculated with a homofermentative Lactobacillus sp. or a Leuconostoc sp. Int. J. Food Microbiol. 15, 99–108.

Borchert, T. V., and V. Nagarajan. 1991. Effect of signal sequence alterations on export of levansucrase in *Bacillus subtilis*. J. Bacteriol. 173:276–282.

Bukhtiyarova, M., Rongguang, Y., and Ray, B. (1994) Analysis of the pediocin AcH gene cluster from plasmid pSMB74 and its expression in a pediocin-negative *Pediococcus acidilactici* strain. Appl Environ Microbiol 60: 3405–3408.

Bureau Central de la CIE, 4, Avenue du Recteur Poincare, 75782 Paris Cedex 16, France.

Cao, G., A. Huhn, and R. E. Dalbey. 1995. The translocation of negatively charged residues across the membrane is driven by the electrochemical potential: evidence for an electrophoresis-like membrane transfer mechanism. EMBO J. 14:866–875.

Casadaban, M. C., and S. N. Cohen. 1980. Analysis of gene control signals by DNA fusion and cloning in *Escherichia coli*. J. Mol. Biol. 138:179–207.

Casadaban, M. J. (1976) Transposition and fusion of the lac genes to selected promoters in *Escherichia coli* using bacteriophage lambda and Mu. J Mol Biol 104: 541–555.

Cavett, J. J. 1963. A diagnostic key for identifying the lactic acid bacteria of vacuum packed bacon. J. Appl. Bacteriol. 26: 453–470.

Chehade, H., and Braun, V. (1988) Iron-regulated synthesis and uptake of colicin V. FEMS Microbiol 52: 177–182.

Chopin, A., Chopin, M.-C., Moillo-Batt, A., and Langella, P. (1984) Two plasmid-determined restriction and modification systems in *Streptococcus lactis*. Plasmid 11: 260–263.

CIE (1976) Commission Internationale de l'Eclairage. 18th Session, London, England. Sept. 1975. CIE Publication 36. Collins, M. D., Rodrigues, U., Ash, C., Aguirre, M., Farrow, J. A. E., Martinez-Murcia, A., Philiips, B. A., Williams, A. M. and Wallbanks, S. (1991) Phylogenetic analysis of the genus Lactobaci/lus and related lactic acid bacteria as determined by reverse transcriptase sequencing of 16S rRNA. FEMS Microbiol. Lett. 77, 5–12.

Dainty, R. H. and Mackey, B. M. (1992) The relationship between the phenotypic properties of bacteria from chill-stored meat and spoilage processes. J. Appl. Bacteriol. Symp. Suppi. 73, 103S–114S.

Diep, D. B., L. S. HCEvarstein, J. Nissen-Meyer, and I. F. Nes. 1994. The gene encoding plantaricin A, a bacteriocin from *Lactobacillus plantarum* C11, is located on the same transcription unit as an agr-like regulatory system. Appl. Environ. Microbiol. 60:160–166.

Difco Manual. 1984. 10th ed., p. 1071. Difco Laboratories Inc., Detroit, Mich.

Dinh, D., I. T. Paulsen, and M. H. Saier, Jr. 1994. A family of extracytoplasmic proteins that allow transport of large molecules across the outer membranes of Gram-negative bacteria. J. Bacteriol. 176:3825–3831.

Edwards, R. A., Dainty, R. H. and Hibbard, C. M. (1985) Putrescine and cadaverine formation in vacuum packed beef. J. Appl. Bacteriol. 58, 13–19. Egan, A F. (1983) Lactic acid bacteria of meat and meat products. Antonie van Leeuwenhoek 49.

Egan, A. F., Ford, A. L. and Shay, B. J. (1980) A comparison of *lMicrobacterium thermosphacta* and *lactobacilli* as spoilage organisms of vacuum-packaged sliced luncheon meats. J. Food Sci. 45 1745–1748.

Fath, F. J., and R. Kolter. 1993. ABC transporters: bacterial exporters. Microbiol. Rev. 57:995–1017.

Franke, C. M., Leenhouts, K. J., Haandrikman, A. J., Kok, J., Venema, G., and Venema, K. (1996) Topology of LcnD, a protein implicated in the transport of bacteriocins from *Lactococcus lactis*. J Bacteriol 178: 1766–1769.

Fremaux, C., Ahn, C., and Klaenhammer, T. R. (1993) Molecular analysis of the lactacin F operon. Appl Environ Microbiol 59: 3906–3915.

Fremaux, C., and T. R. Klaenhammer. 1994. Helveticin J, a large heat-labile bacteriocin from *Lactobacillus helveticus*, p. 397–418. In L. De Vuyst and E. J.

Gasson, M. J. 1983. Plasmid complements of *Streptococcus lactis* NCDO 712 and other lactic streptococci after proptoplast-induced curing. J.Bacteriol. 154:1–9.

Gilson, L., H. K. Mahanty, and R. Kolter. 1987. Four plasmid genes are required for colicin V synthesis, export, and immunity. J. Bacteriol. 169:2466–2470.

Gilson, L., H. K. Mahanty, and R. Kolter. 1990. Genetic analysis of an MDR-like export system: the secretion of colicin V. EMBO J. 9:3875–3884.

González, B., P. Arca, B. Mayo, and J. E. Suárez. 1994. Detection, purification, and partial characterization of plantaricin C, a bacteriocin produced by a *Lactobacillus plantarum* strain of dairy origin. Appl. Environ. Microbiol. 60:2158–2163.

Graham, D. C., and McKay, L. L. (1985) Plasmid DNA in strains of *Pediococcus cerevisiae* and *Pediococcus pentosaceus*. Appl Environ Microbiol 50: 532–534.

Greer, G. G., and S. D. M. Jones. 1991. Effects of lactic acid and vacuum packaging on beef processed in a research abattoir. Can. Inst. Food Sci. Technol. J. 24:161–168.

Greer, G. G. and Murray, A. C. (1991) Freezing effects on quality, bacteriology and retail case life of pork. J. Food Sci. 56, 891–894.

Greer, G. G., Dilts, B. D. and Jeremiah, L. E. (1993) Bacteriology and retail case life of pork after storage in carbon dioxide. J. Food Prot. 56, 689–693.

Héchard, Y. B. Dérijard, F. Letellier, Y. Cenatiempo. 1992. Characterization and purification of mesentericin Y105, an anti-*Listeria* bacteriocin from *Leuconostoc mesenteroides*. Journal of General Microbiology. 138:2725–2731.

Hanna. M. O., Savell, J. W., Smith. G. C., Purser, D. E., Gardner. F. A. and Vanderzant, C. (1983) Effect of growth of individual meat bacteria on pH. color and odor of aseptically prepared vacuum-packaged round steaks. J. Food Prot. 42. 216–221.

Hastings, J. W., M. Sailer, K. Johnson, K. L. Roy, J. C. Vederas, and M. E. Stiles. 1991. Characterization of leucocin A-UAL 187 and cloning of the bacteriocin gene from *Leuconostoc gelidum*. J. Bacteriol. 173:7491–7500.

Hastings, J. W. and Stiles, M. E. (1991) Antibiosis of *Leuconostoc gelidum* isolated from meat. J. Appl. Bacteriol. 70, 127–134.

Hastings, J. W., Sailer, M., Johnson, K., Roy, K. L., Vederas, J. C., and Stiles, M. E. (1991) Characterization of leucocin A-UAL 187 and cloning of the bacteriocin gene from *Leuconostoc gelidum*. J Bacteriol 173: 7491–7500.

Håvarstein, L. S., D. B. Diep, and I. F. Nes. 1995. A family of bacteriocin ABC transporters carry out proteolytic processing of their substrates concomitant with export. Mol. Microbiol. 16:229–240.

Håvarstein, L. S., H. Holo, and I. F. Nes. 1994. The leader peptide of colicin V shares consensus sequences with leader peptides that are common among peptide bacteriocins produced by Gram-positive bacteria. Microbiology 140:2383–2389.

Henderson, J. T., A. L. Chopko, and P. D. van Wassenaar. 1992. Purification and primary structure of pediocin PA-1 produced by Pediococcus acidilactici PAC-1.0. Arch. Biochem. Biophys. 295:5–12.

Higgins, C. F. (1992) ABC transporters: from microorganisms to man. Annu Rev Cell Biol 8: 67–113.

Holo, H, Nilssen, O. and Nes, I. F. (1991) Lactococcin A, a new bacteriocin from Lactococcus lactis subsp. cremoris: isolation and characterization of the protein and its gene. J Bacteriol 173: 3879–3887.

Holo, H., and I. F. Nes. 1989. High-frequency transformation, by electroporation fo Lactococcus lactis subsp. cremoris grown with glycine in osmotically stabilized media. Appl. Environ. Microbiol. 55:3119–3123.

Hui, F. M., and D. A. Morrison. 1991. Genetic transformation in Streptococcus pneumoniae: nucleotide sequence analysis shows comA, a gene required for competence induction, to be a member of the bacterial ATP-dependent transport family. J. Bacteriol. 173:372–381.

Hui, F. M., L. Zhou, and D. A. Morrison. 1995. Competence for genetic transformation in Streptococcus pneumoniae: organization of a regulatory locus with homology to two lactococcin A secretion genes. Gene 153:25–31.

Izard, J. W., and D. A. Kendall. 1994. Signal peptides: exquisitely designed transport promoters. Mol. Microbiol. 13:765–773.

Jarchau, T., Chakraborty, T., Garcia, F., and Goebel, W. (1994) Selection for transport competence of C-terminal polypeptides derived from Escherichia coli hemolysin: the shortest peptide capable of autonomous HlyB/HlyD-dependent secretion comprises the C-terminal 62 amino acids of HlyA. Mol Gen Genet 245: 53–60.

Joerger, M. C., and T. R. Klaenhammer. 1990. Cloning, expression, and nucleotide sequence of the Lactobacillus helveticus 481 gene encoding the bacteriocin helveticin J. J. Bacteriol. 172:6339–6347.

Jung, G. (1991) in Nisin and Novel Lantibiotics. Jung, G., and Sahl, H.-G. (eds). Leiden:Escom, pp1–34.

Kandler, O., and O. Weiss. 1986. Regular, nonsporeforming Gram-positive rods, p. 1208–1260. In: P. H. A. Sneath, M. E. Mair, N. S., Sharpe, and J. G. Holt (ed.), Bergey's manual of systematic bacteriology, vol. 2. Williams and Wilkins, Baltimore, Md.

Klaenhammer, T. R. 1993. Genetics of bacteriocins produced by lactic acid bacteria. FEMS Microbiol. Rev. 12:39–85.

Kuipers, O. P., H. S. Rollema, W. M. de Vos, and J. Siezen. 1993. Biosynthesis and secretion of a precursor of nisin Z by Lactococcus lactis, directed by the leader peptide of the homologous lantibiotic subtilin from Bacillus subtilis. FEBS Lett. 330:23–27.

Laemmli, U. K. (1970). Cleavage of structural proteins during the n-7 assembly of the head of bacteriophage T4. Nature (London) 227:680–685.

Lee, C., P. Li, H. Inouye, E. R. Brickman, and J. Beckwith. 1989. Genetic studies on the inability of β-galactosidase to be translocated across the Escherichia coli cytoplasmic membrane. J. Bacteriol. 171:4609–4616.

Leer, R. J., J. M. van der Vossen, M. van Giezen, J. M. van Noort, and P. H. Pouwels. 1995. Genetic analysis of acidocin B, a novel bacteriocin produced by Lactobacillus acidophilus. Microbiology 141:1629–1635.

Leisner, J., G Greer, B. Dilts, M. Stiles. 1994. Effect of growth of selected lactic acid bacteria on storage life of beef stored under vacuum and in air.

Leisner, J., G. Greer, and M. Stiles. 1996. Control of beef spoilage by a sulfide-producing lactobacillus sake strain with bacteriocinogenic leuconostoc gelidum UAL187 during anaerobic storage at 2° C.

Lewus, C. B., Kaiser, A. and Montville. T. (1991) Inhibition of food-borne bacterial pathogens by bacteriocins from lactic acid bacteria isolated from meat. Appl. Environ., Uicrobiol. 57. 1683–1688.

Li, P., J. Beckwith, and H. Inouye. 1988. Alteration of the amino terminus of the mature sequence of a periplasmic protein can severely affect protein export in Escherichia coli. Proc. Natl. Acad. USA 85:7685–7689.

Mandel, M., and A. Higa. 1970. Calcium dependent bacteriophage DNA infection. J. Mol. Biol. 53:159–162.

Marugg, J. D., C. F. Gonzalez, B. S. Kunka, A. M. Ledeboer, M. J. Pucci, M. Y. Toonen, S. A. Walker, L. C. M. Zoetmulder, and P. A. Vandenbergh. 1992. Cloning, expression, and nucleotide sequence of genes involved in production of pediocin PA-1, a bacteriocin from Pediococcus acidilactici PAC1.0. Appl. Environ. Microbiol. 58:2360–2367.

McMullen, L. M., and M. E. Stiles. 1993. Microbial ecology of fresh pork stored under modified atmosphere at −1, 4.4 and 10° C. Int. J. Food Microbiol. 18:1–14.

McMullen, L. M., and M. E. Stiles. 1994. Quality of fresh retail pork cuts stored in modified atmosphere under temperature conditions simulating export to distant markets. Meat Sci. 38:163–177.

Montel, M.-C., R. Talon, J. Fournaud, and M.-C. Champomier. 1991. A simplified key for identifying homofermentative Lactobacillus and Carnobacterium spp. from meat. J. Appl. Bacteriol. 70: 469–472.

Muriana, P. M., and T. R. Klaenhammer. 1991. Cloning, phenotypic expression, and DNA sequence of the gene for Lactacin F, an antimicrobial peptide produced by Lactobacillus spp. Appl. Environ. Microbiol. 173:1779–1788.

Pearson, W. R., and D. J. Lipman. 1988. Improved tools for biological sequence comparison. Proc. Natl. Acad. Sci. USA 85:2444–2448.

Pugsley, A. P. 1993. The complete general secretory pathway in Gram-negative bacteria. Microbiol. Rev. 57:50–108.

Quadri, L. E. N., K. L. Roy, J. C. Vederas, and M. E. Stiles. 1996. J. Bacteriol. submitted.

Quadri, L. E. N., M. Sailer, K. L. Roy, J. C. Vederas, and M. E. Stiles. 1994. Chemical and genetic characterization of bacteriocins produced by Carnobacterium piscicola LV17B. J. Biol. Chem. 269:12204–12211.

Quadri, L. E. N., M. Sailer, M. Terebiznek, K. L. Roy, J. C. Vederas, and M. E. Stiles. 1995. Characterization of the protein conferring immunity to the antimicrobial peptide carnobacteriocin B2 and expression of carnobacteriocins B2 and BM1. J. Bacteriol. 177:1144–1151.

Randall, L. L., and S. J. S. Hardy. 1986. Correlation of competence for export with lack of tertiary structure of the mature species; a study in vivo of maltose binding protein in *E. coli*. Cell 46:921–928.

Renerre. M. and Montel, M-C. (1986) Inoculation of steaks with Lacrobacillus species and effect on colour and microbial counts. Proceedings of the 3'nd meeting of European Meat Research Workers, pp. 213–216.

Reuter, G. 1970. Laktobazillen und eng verwandte Mikroorganismen in Fleisch und Fleischerzeugnissen 2. Mitteilung: Die charakterisierung der isolierten Laktobazillenstamme. Fleischwirtsch. 50: 954–962.

Rottlander, E., and Trautner, T. A. (1970) Genetic and transfection studies with *Bacillus subtilis* phage SP50. J Mol Biol 108: 47–60.

Ruhr, E., and Sahl, H.-G. (1985) Mode of action of the peptide antibiotic nisin and influence on the membrane potential of whole cells and on cytoplasmic and artificial membrane vesicles. Antimicrob Agents Chemother 27: 841–845.

Ruiz-Barba, J. .L., D. P. Cathcart, P. J. Warner, and R. Jiménez-Diaz. 1994. Use of *Lactobacillus plantarum* LPCO10, a bacteriocin producer, as a starter culture in Spanish-style green olive fermentations. Appl. Environ. Microbiol. 60:2059–2064.

Sahl, H.-G. (1991) In Nisin and novel lantibiotics. Jung, G. and Sahl, H.-G. (eds). Leiden. Escom, pp.347–358.

Sambrook, J., Fritsch, E. F., and Maniatis, T. (1989) Molecular Cloning: A Laboratory Manual, 2nd. ed. Cold Spring Harbor, N.Y.: Cold Spring Harbor Laboratory Press.

Sanger, F., S. Nicklen, and A. R. Coulson. 1977. DNA sequencing with chain-termination inhibitors. Proc. Natl. Acad. Sci. USA 74:5463–5467.

SAS Institute (1985) SAS User's Guide: Statistics. SAS Institute, Inc. Cars. NC.

Schägger, H., and von Jagow, G. (1987) Tricine-sodium dodecyl sulfate-polyacrylamide gel electrophoresis for the separation of proteins in the range from 1 to 100 kDa. Biochem 166: 368–379.

Schillinger, U. and Lucke, F.-K. (1987) Lactic acid bacteria on vacuum-packed meat and their influence on storage life. Fleischwirtsch. 67, 1244–1'48.

Schillinger, U., and F.-K. Lücke. 1987. Identification of lactobacilli from meat and meat products. Food Microbiol. 4:199–208.

Schillinger. U. and Lucke, F.-K. (1989) Antibacterial activity of *Lacrobacillus sake* isolated from meat Appl. Environ. Microbiol. S5, 1901–1906.

Shaw, B. G., and C. D. Harding. 1984. A numerical taxonomic study of lactic acid bacteria from vacuum packed beef, pork, lamb and bacon. J. Appl. Bacteriol. 56: 25–40.

Shaw, B. G., and C. D. Harding. 1985. Atypical lactobacilli from vacuum packaged meats: Comparison by DNA hybridization, cell composition and biochemical tests with a description of *Lactobacillus carnis* sp. nov. System. Appl. Microbiol. 6:291–297.

Shay, B. J. and Egan, A. F. (1981) Hydrogen sulphide production and spoilage of vacuum-packed beef by a Lactobacillus In: T. A. Roberts, G. Hobbs, J. H. B. Christian and N. Skovgaard (editors), Psychrotrophic Microorganisms in Spoilage and Pathogenicity. Academic Press. New York. pp. 241–251.

Simonen, M., and I. Palva. 1993. Protein secretion in Bacillus species. Microbiol. Rev. 57:109–137.

Siragusa and Nettles Cutter ( ) ????

Smith, G. C., Hall, L. C. and Vanderzant, C. (1980) Inoculation of beef steaks with Lactobacillus species before vacuum packaging. 11. Effect on meat quality characteristics. J. Food Prot. 43, 842–849.

Southern, E. M. (1975). Detection of specific sequences among DNA fragments separated by gel electrophoresis. J. Mol. Biol. 98:503–517.

Stiles, M. E. and Hastings, J. W. (1991) Bacteriocin production by lactic acid bacteria: potential for use in meat preservation. Trends Food Sci. Technol. 2, 247–251.

Stoddard, G. W., Petzel, J. P.,van Belkum, M. J., Kok, J., and McKay, L. L. (1992) Molecular analyses of the lactococcin A gene cluster from *Lactococcus lactis* subsp. *lactis* biovar. diacetylactis WM4. Appl Environ Microbiol 58: 1952–1961.

Studier, F. W., and Moffat, B. (1986) Use of bacteriophage T7 RNA polymerase to direct selective high level expression of cloned genes. J Mol Biol 189: 113–130.

Tabor, S., and Richardson, C. C. (1985) A bacteriophage T7 RNA polymerase promoter system for controlled exclusive expression of specific genes. Proc Natl Acad Sci USA 82: 1074–1078.

Terzaghi, B. E., and Sandine, W. E. (1975) Improved medium for lactic streptococci and their bacteriophages. Appl Microbiol 29:807–813.

Tichaczek, P. S., R. F. Vogel, and W. P. Hammes. 1994. Cloning and sequencing of sakP encoding sakacin P, the bacteriocin produced by *Lactobacillus sake* LTH 673. Microbiology 140:361–367.

Van Belkum, M. J., B. J. Hayema, R. E Jeeninga, J. Kok, and G. Venema. 1991. Organization and nucleotide sequences of two lactococcal bacteriocin operons. Appl. Environ. Microbiol. 57:492–498.

Van Belkum, M. J., J. Kok, and G. Venema. 1992. Cloning, sequencing, and expression in *Escherichia coli* of lcnB, a third bacteriocin determinant from the lactococcal bacteriocin plasmid p9B4–6. Appl. Environ. Microbiol. 58:572–577.

van Belkum, M. J. 1994. Lactococcins, bacteriocins of *Lactococcus lactis*, p. 301–318. In L. De Vuyst and E. J. Vandamme (ed.), Bacteriocins of Lactic Acid Bacteria: Microbiology, Genetics and Applications. Blackie Academic & Professional, Glasgow.

van Belkum, M. J., and Stiles, M. E. (1995) Molecular characterization of genes involved in the production of the bacteriocin leucocin A from *Leuconostoc gelidum*. Appl Environ Microbiol 61: 3573–3579.

van Belkum, M. J., Hayema, B. J., Geis, A., Kok, J., and Venema, G. (1989) Cloning of two bacteriocin genes from a lactococcal bacteriocin plasmid. Appl Environ Microbiol 55: 1187–1191.

van Belkum, M. J., Hayema, B. J., Jeeninga, R. E., Kok, J., and Venema, G. (1991a) Organization and nucleotide sequences of two lactococcal bacteriocin operons. Appl Environ Microbiol 57: 492–498.

Van Belkum, M. J., J. Kok, and G. Venema. 1992. Cloning, sequencing, and expression in *Escherichia coli* of lcnB, a third bacteriocin determinant from the lactococcal bacteriocin plasmid p9B4–6. Appl. Environ. Microbiol. 58:572–577.

van Belkum, M. J., Kok, J., Venema, G., Holo, H., Nes, I. F., Konings, W. N., and Abee, T. (1991b) The bacteriocin lactococcin A specifically increases the permeability of lactococcal cytoplasmic membranes in a voltage-independent, protein-mediated manner. J Bacteriol 173: 7934–7941.

van de Guchte, M., J. Kok, and G. Venema. 1992. Gene expression in *Lactococcus lactis*. FEMS Microbiol. Rev. 88:73–92.

Van de Guchte, M., J. M. B. M. van der Vossen, J. Kok, and G. Venema. 1989. Construction of a lactococcal expression vector: expression of hen egg white lysozyme in *Lactococcus lactis* subsp. *lactis*. Appl. Environ. Microbiol. 55:224–228.

van der Meer, J. R., Rollema, H. S., Siezen, R. J., Beerthuyzen, M. M., Kuipers, O. P., and de Vos, W. M. (1994) Influence of amino acid substitutions in the nisin leader peptide on biosynthesis and secretion of nisin by *Lactococcus lactis*. J Biol Chem 269: 3555–3562.

Van der Vossen, J. M. B. M., D.van der Lelie, and G. Venema. 1987. Isolation and characterization of *Streptococcus cremoris* WG2-specific promoters. Appl.Environ. Microbiol. 48:2452–2457.

van der Vossen, J. M. B. M., J. Kok, and G. Venema (1985). Construction of cloning, promoter-screening, and terminator-screening shuttle vectors for *Bacillus subtilis* and *Streptococcus lactis*. Appl. Environ. Microbiol. 50:540–542.

Vandamme (ed.), Bacteriocins of lactic acid bacteria: microbiology, genetics, and applications. Chapman and Hall, Ltd. London.

Venema, K., Dost, M. H. R., Beun, P. A. H., Haandrikman, A. J., Venema, G., and Kok, J. (1996) The genes for secretion and maturation of lactococcins are located on the chromosome of *Lactococcus lactis* IL1403. Appl Environ Microbiol 62: 1689–1692.

Venema, K., Kok, J., Marugg, J. D., Toonen, M. Y., Ledeboer, A. M., Venema, G., and Chikindas, M. L. (1995) Functional analysis of the pediocin operon of *Pediococcus acidilactici* PAC1.0: PedB is the immunity gene and PedD is the processing enzyme. Mol Microbiol 17: 515–522.

Vieira, J., and J. Messing (1982). The pUC plasmids, an M13mp7-derived system for insertion mutagenesis and sequencing with synthetic universal primers. Gene 19:259–268.

Vieira, J., and J. Messing. 1987. Production of single-stranded plasmid DNA. Methods Enzymol. 153:3–11.

Von Heijne, G. 1986. Net N-C charge imbalance may be important for signal sequence function in bacteria. J. Mol. Biol. 192:287–290.

Wandersman, C., and Delepelaire, P. (1990) TolC, an *Escherichia coli* outer membrane protein required for hemolysin secretion. Proc Natl Acad Sci USA 87: 4776–4780.

Wilkinson, B. J., and D. Jones. 1977. A numerical taxonomic survey of Listeria and related bacteria. J. Gen. Microbiol. 98: 399–421.

Worobo, R. W., T. Henkel, M. Sailer, K. L. Roy, J. C. Vederas, and M. E. Stiles. 1994. Characteristics and genetic determinant of a hydrophobic peptide bacteriocin, carnobacteriocin A, produced by *Carnobacterium piscicola* LV17A. Microbiology 140:517–526.

Worobo, R. W., M. J. van Belkum, M.Sailer, K. L.Roy, J. C. Vederas, and M. E. Stiles. 1995. A signal peptide secretion-dependent bacteriocin from *Carnobacterium divergens*. J.Bacteriol. 177:3143–3149.

Zhang, F., Greig, D. I., and Ling, V. (1993) Functional replacement of the hemolysin A transport signal by a different primary sequence. Proc Natl Acad Sci USA 90: 4211–4215.

Zhang, F., Yin, Y., Arrowsmith, C. H., and Ling, V. (1995a) Secretion and circular dichroism analysis of the C-terminal signal peptides of HlyA and LktA. Biochemistry 34: 4193–4201.

Zhang, L. H., M. J. Fath, H. K. Mahanty, P. C. Tai, and R. Kolter. 1995b. Genetic analysis of the colicin V secretion pathway. Genetics 141:25–32.

Zúñiga, M., I. Pardo, and S. Ferrer. 1993. An improved medium for distinguishing between homofermentative and heterofermentative lactic acid bacteria. Int. J. Food Microbiol. 18:37–42.

TABLE I

Bacterial strains and plasmids

| Bacterial Strain or plasmid | Relevant Characteristics[a] | Reference or source |
|---|---|---|
| Strains | | |
| *C. divergens* | | |
| LV13 | Leucocin A sensitive indicator strain | Shaw[c] |
| | Carnobacteriocin sensitive indicator strain dvn+ dvi+ (containing pCD3.4),CbnB2$^S$ (NCFB 2855) | NCFB[b] |
| AJ | Dvn$^S$ DbnB2$^r$ | laboratory isolate |
| *C. piscicola* | | |
| LV17C | Bac$^-$, plasmidless mutant derived from *C. piscicola* Lv 17B Dvn$^S$ DbnB2$^S$, plasmidless | Ahn & Stiles (1990), |
| LV17A | cbnA (containing pCp49), Bac$^+$Dvn$^S$ | Ahn & Stiles (1990), |
| LV17B | Bac$^+$, containing pCP40 cbnB2 and cbnBMI (containing pCP40) | Ahn & Stiles (1990), |
| UAL26 | Dvn$^S$ DbnB2$^S$, Bcn$^+$, plasmidless, Bac$^+$Dvn$^S$ | Abn & Stiles (1990), Shaw[c] |
| *Lactococcus lactis* subsp. *lactis* | | |
| MG1363 | Dvn$^r$, plasmidless | Gasson (1983) |
| IL 1403 | Dvn$^r$DvnB2$^r$, plasmidless | Chopin et al (1984), |
| *Lb. sake* | | |
| 1218 | Sulfide producing spoilage organism | L. McMullen, U. of Alberta |
| *L. gelidum* | | |
| UAL 187 | bac$^+$ wildtype strain with 5.0, 7.6 and 9.2 MDa plasmids | Hastings & Stiles (1991) |

TABLE I-continued

Bacterial strains and plasmids

| Bacterial Strain or plasmid | Relevant Characteristics[a] | Reference or source |
| --- | --- | --- |
| UAL 187-22 | bac+ strain with 7.6 and 9.2 MDa plasmids | Hastings & Stiles (1991) |
| UAL 187-13 | bac− strain with 9.2 MDa plasmid | Hastings & Stiles (1991) |
| *E. Coli* | | |
| DH5α | F−endA1 hsdRI7 ($r_k$−$m_k$+)supE44 thi-1 1-recA1 gyrA96 relA1(argF-lacZYA)U169 f80dlacZ__M15 | BRL Life Techonologies Inc. |
| MH1 | MC1061 derivative; araD139 lacX74 galU galK hsr hsm+ strA | Casadaban & Cohen (1930), |
| MV1193 | Δ(lac proAB) rpsL thi endA spcB15 hsdR4 Δ(srl-recA) 306::Tn10(tetr) F[traD36 proAB+ lac$^q$ lacZΔM15] | |
| LQ5.21 | *E.coli* MV1193 containing pLQ5.21 | Quadri et al (1994) |
| LQ7.2 | *E.coli* MV1193 containing pLQ7.2 | Quadri et al (1994) |
| Plasmids | | |
| pCD3.4 | dvn+, dvi+ (divergicin A producer), 3.4 kb | Worobo et al (1995) |
| pCD4.4 | pCD3.4 containing 1.0-kb EcoRI Cm$^r$ gene of pGS30; Cm$^r$dvn$^+$dvi$^+$,4.4kb | Worobo et al (1995) |
| pCD40 | 61-kb plasmid conferring Bac+ Imm+ phenotype | Ahn & Stiles (1990) |
| pGKV210 | Em$^r$,4.4kb | van der Vossen et al (1987) |
| pGKV259 | Em$^r$ Cm$^r$ 5.0 kb | Van der Vossen (1987) |
| pGS30 | pUC7 containing 1.0-kb PstI Cm$^r$ gene of pC194; Cm$^r$, 3.7 kb | G. Venema[d] |
| pJH6.1F | pUC118 containing 2.9-kb HpaII fragment from pLG7.6, Amp$^r$, 6.1 kb | Hastings et al (1991) |
| pJKM05 | 528-bp HindIII-XbaI cbnB2, cbiB2 PCR product in pUC118, Ampr | McCormick et al (1996) |
| pJKM07 | 266-bp EcoRI-HindIII fragment of pJKM05 in pUC118 | McCormick et al (1996) |
| pJKM08 | 262-bp EcoRI fragment of pJKM05 in pUC118 | McCormick et al (1996) |
| pJKM14 | pMG36e containing divergicin A signal peptide fused to carnobacteriocin B2 structural gene and also containing carnbacteriocin B2 immunity gene, cbnB2+, cbiB2+, Emr | McCormick et al (1996) |
| pJKM16 | 335-bp SacI-EcoRI fragment from pJKM14 cloned in pUC118 | McCormick et al (1996) |
| pKM1 | pUC7 containing 1.3-kb pstI Km$^r$ gene of pUB110; Km$_r$, 3.7 kb | G. Venema[d] |
| pLG7.6 | Lca-Imm+, 18 kb | Hasting & Stiles (1991) |
| pLQ5.21 | pUC118 containing a 1.9-kb HindIII fragment of pCP40 | Quadri et al (1995) |
| pLQ7.2 | pUC118 containing a 4.0-kb EcoRI-PstI genomic fragrnent from *C. piscicola* LV17C | Quadri et al (1995) |
| pLQ24 | pCaT containing 16-kb insert from pCP40, cbnB2+, cbiB2+, Cmr, 24.5 kb | Quadri et al (1995) |
| pMB500 | Km$^r$, 18.2 kb; specifying lactococcins A and B | van Belkum et al (1989) |
| pMB553 | Em$^r$, 18.2 kb; specifying lactococcin A | van Belkum et al (1989) |
| pMG36c | expression vector, Em$^r$, 3.6 kb | van Belkum et al (1989) van de Guchte et al (1989) |
| pMJ1 | pGKV210 containing 2.9-kb HpaII fragment from pJH6.1F, Em$^r$, 6.8 kb | van Belkum & Stiles (1995) |
| pMJ3 | pGKV210 containing 1-kb HpaI-DraI fragment from pJH6.1F, Em$^r$, 5.4 kb | van Belkum & Stiles (1995) |
| pMJ4 | pUC118 containing 123-kb HindIII fragment from pLG7.6, Amp$^r$, 15.5 kb | van Belkum & Stiles (1995) |
| pMJ6 | pMG36e containing the 8-kb SacI-HindIII fragment from pMJ4. EmT, 11.6 kb | van Belkum & Stiles (1995) |
| pMJ10 | pMG36e containing the 7.9-kb HindlII-Nrulfragment from pMJ4, Em$^r$, 11.4 kb | van Belkum & Stiles (1995) |
| pMJ16 | EcoRV-BamHI deletion derivative fo pMJ6, Em$^r$, 10.6 kb | van Belkum & Stiles (1995) |
| pMJ17 | BstE11-Sta-I deletion derivative of pMJ6. Em$^r$m, 10.6 kb | van Belkum & Stiles (1995) |
| pMJ18 | EcoRV-HindlII deletion derivative of pMJ6, Em$^r$, 8.7 kb | van Belkum & Stiles (1 995) |
| pMJ20 | Frameshift mutation in ClaI site of pMJ3, Em$^r$, 5.4 kb | van Belkum & Stiles (1995) |
| pMJ26 | Frameshift mutation in NsiI site of pMJ6, Em$^r$, 11.6 kb | van Belkum & Stiles (1995) |

TABLE I-continued

Bacterial strains and plasmids

| Bacterial Strain or plasmid | Relevant Characteristics[a] | Reference or source |
|---|---|---|
| pRW19e | pMG36e containing 514-bp EcoRV-AccI fragment; dvn+,dvi+, Emr | McCormick et al (1996) |
| PRW5.6 | pGKV259 containing 514-bp EcoRV-AccI fragment; Em$^r$dvn$^+$dvi$^+$, 5.6 kb | Worobo et al (1995) |
| pRW6.0 | pGKV259 containing divergicin signal peptide fused to alkaline phosphatase | Worobo et al (1995) |
| pUC118 | 3.2-kb cloning vector, Amp$^R$, lacZ | Veira & Messing (1987) |
|  | IacZ$^r$ Ampr, 3.2 kb | Veira & Messing (1986) | dvn+,divergicin A structural gene; dvi+,divergicin A immunity gene; cbnB2+, carnobacteriocin B2 structural gene; cbiB2+, carnobacteriocin B2 immunity gene; Dvns, divergicin A sensitivee; Dvnr, divergicin A resistant; CbnB2s, carnobacteriocin B2 sensitive; CbnB2r, carnobacteriocin B2 resistant; Bcn+, bacteriocin producer (unnamed); Ampr, ampicillin resistant; Cmr, chloroamphenicol resistant; Emr, erythromycin resistant.
[b]NCFB, National Collection of Food Bacteria, Reading, United Kingdon.
[c]Supplied by Dr. B. G. Shaw, Institute for Food Research, Langford, Bristol, UK.
[d]Strain from the laboratory of G. Venema, Department of Genetics, University of Groningen. Haren, The Netherlands.

TABLE 2

Spectrum of of Antibiotic Activity of a Variety of Purified Bacteriocins expressed as the Number of strains inhibited/Number of strains tested

| | | Bacteriocin | | | | | | | | |
|---|---|---|---|---|---|---|---|---|---|---|
| | | cbn 26 | | cbn A | | cbn B | | Leu A | | Broch C | |
| Genus of Strains tested | | 1AU | 8AU | 1AU | 8AU | 1AU | 8AU | 1AU | 8AU | 1AU | 8AU |
| Bacillus | vegetative cells | 2/5 | 5/5 | 2/5 | 2/5 | 2/5 | 2/5 | 2/5 | 2/5 | 1/5 | 4/5 |
|  | spores | 5/5 | 5/5 | 0/5 | 0/5 | 0/8 | 0/8 | 0/8 | 1/8 | 3/8 | 3/8 |
| Clostridia | vegetative cells | 3/8 | 6/8 | 0/8 | 0/8 | 0/8 | 0/8 | 0/8 | 1/8 | 3/8 | 3/8 |
|  | spores | 0/7 | 4/7 | 0/7 | 0/7 | 0/7 | 0/7 | 0/7 | 0/7 | 1/7 | 1/7 |
| Staphylococcus | | 1/7 | 1/7 | 0/7 | 1/7 | 1/7 | 1/7 | 0/7 | 6/7 | 7/7 | 7/7 |
| Streptococcus | | 2/3 | 2/3 | 0/3 | 0/3 | 0/3 | 013 | 0/3 | 1/3 | 1/3 | 2/3 |
| Listeria | | 42/42 | 42/42 | 4/42 | 21/42 | 10/42 | 26/42 | 39/42 | 40/42 | 0/42 | 39/42 |
| G negative strains | | 0/29 | 0/29 | 0/29 | 0/29 | 0/29 | 0/29 | 0/29 | 0/29 | 0/29 | 0/29 |
| Brochothrix | | 14/14 | 14/14 | 0/14 | 0/14 | 0/14 | 0/14 | 0/14 | 0/14 | 13/14 | 13/14 |
| Carnobacteria | | 0/14 | 0/14 | 0/14 | 0/14 | 0/14 | 0/14 | 14/14 | 14/14 | 0/14 | 0/14 |
| Enterococcus | | 11/14 | 13/14 | 2/14 | 2/14 | 3/14 | 3/14 | 7/14 | 9/14 | 8/14 | 12/14 |
| Lactobacillus | | 15/17 | 16/17 | 0/17 | 1/17 | 0/17 | 0/17 | 1/17 | 1/17 | 3/17 | 8/17 |
| Lactococcus | | 8/8 | 8/8 | 0/8 | 0/8 | 0/8 | 0/8 | 0/8 | 0/8 | 0/8 | 3/8 |
| Leuconostoc | | 9/9 | 9/9 | 1/9 | 1/9 | 1/9 | 1/9 | 5/9 | 5/9 | 1/9 | 8/9 |
| Pediococcus | | 2/3 | 3/3 | 0/3 | 0/3 | 0/3 | 0/3 | 0/3 | 0/3 | 0/3 | 2/3 |

TABLE 3

Spectrum of of Antibiotic Activity of a Variety of Purified Bacteriocins expressed as the Number of strains inhibited/Number of strains tested

| | | Bacteriocin and Number of units used in the Assay | | | | | | | |
|---|---|---|---|---|---|---|---|---|---|
| | | Leu A | | Mesen Y105 | | cbn 26 Enterocin Brochocin | | Nisin | |
| Genus of Strains Tested | | 1AU | 8AU | 1AU | 8AU | 1AU | 8AU | 1AU | 8AU |
| Bacillus | vegetative cells | 2/5 | 2/5[a] | 3/5 | 5/5 | 3/5[p] | 5/5 | 5/5 | 5/5 |
|  | spores | 0/5 | 0/5 | 5/5[b] | 5/5[b] | 5/5 | 5/5 | 5/5 | 5/5 |
| Clostridia | vegetative cells | 0/8 | 1/8[c] | 0/8 | 1/8[d] | 4/8[q] | 6/8 | 7/8 | 8/8 |
|  | spores | 0/7 | 0/7 | 0/7 | 0/7 | 1/7 | 4/7[r] | 5/7 | 7/7 |
| Staphylococcus | | 1/7[e] | 1/7[e] | 1/7[cf] | 7/7[cf] | 1/7 | 7/7 | 3/7 | 7/7 |
| Streptococcus | | 0/3 | 0/3 | 0/3 | 3/3[g] | 2/3 | 2/3 | 1/3 | 2/3 |
| Listeria | | 39/42[h] | 40/42[t] | 36/42[h] | 42/42 | 42/42 | 42/42 | 42/42 | 42/42 |
| Brochothrix | | 0/14 | 0/14 | 0/14 | 0/14 | 14/14 | 14/14 | 14/14 | 14/14 |
| Carnobacteria | | 12/19[j] | 18/19[k] | 17/19[j] | 19/19 | 19/19 | 19/19 | 19/19 | 19/19 |

TABLE 3-continued

Spectrum of of Antibiotic Activity of a Variety of Purified Bacteriocins expressed as the Number of strains inhibited/Number of strains tested

| | Bacteriocin and Number of units used in the Assay | | | | | | | |
|---|---|---|---|---|---|---|---|---|
| | Leu A | | Mesen Y105 | | cbn 26 Enterocin Brochocin | | Nisin | |
| Genus of Strains Tested | 1AU | 8AU | 1AU | 8AU | 1AU | 8AU | 1AU | 8AU |
| Enterococcus | 7/14[l] | 9/14[l] | 3/14[l] | 9/14[l] | 14/14 | 14/14 | 12/14 | 14/14 |
| Lactobacillus | 1/17[m] | 1/17[m] | 1/17[m] | 1/17[m] | 15/17 | 16/17[s] | 16/17 | 17/17 |
| Lactococcus | 0/8 | 0/8 | 0/8 | 1/8[n] | 8/8 | 8/8 | 4/8 | 6/8[t] |
| Leuconostoc | 5/9 | 5/9 | 5/9 | 6/9[o] | 9/9 | 9/9 | 9/9 | 9/9 |
| Pediococcus | 0/3 | 0/3 | 0/3 | 0/3 | 2/3 | 3/3 | 3/3 | 3/3 |

Notes for table 3.
[a]No inhibition against *B. cereus* ATCC14579, HPB384, HPB948.
[b]Small, cloudy zone
[c]*C. pasterianum* ATCC6013.
[d]*C. bifermentans* ATCC19299
[e]All inhibited *S. aureus* S13
[f]Except S13, inhibition zones of other indicators were small, cloudy.
[g]Inhibition to *S. sanguis* ATCC10556 was stronger than others
[h]Both had no inhibition to *L. monocytogenes* L10501, L10507, L028, while Y105 had no activity to *L. monocytogenes* L10506, L10526, *L. innocua* L10200 either.
[i]No inhibition to LI0501, LI0507
[j]Both were inactive to *C. piscicola* ATCC43225, *C. mobile* ATCC49516.
[k]No inhibition to ATCC49516 Leu A did not inhibit *C. piscicola* LV17, LV17B, LV17C, LVC2/8B
[l]Both had no inhibition to *E. faecalis* ATCC33186, *faecium* ATCC 19434, HPB956, ENSAIA631, Leu A inhibited *E. faecalis* HPB390, while Y105 did not.
[m]Only active to *L. sake* 20017
In direct and deferred antagonism test, Y105 was active to *L. confusus* ATCC10881
[n]Small zone against *L. garviae* ATCC43921
[o]Inhibit *L. paramesenteriodes* DSM20288
Other 5 inhibited indicators were the same to Leu A and Mesen Y105
[p]*B. cereus*, APB384, HPB948
[q]ATCC19401, ATCC25784, ATCC7995
[r]ATCC25784, ATCC19401, ATCC6013
[s]*Lb. plantarum*, BFE905
[t]UAL245, ATCC11454

TABLE 4

Spectrum of of Antibiotic Activity of a Variety of Purified Bacteriocins expressed as the Number of strains inhibited/Number of strains tested

| | | Bacteriocin Tested | | | | | | | | | |
|---|---|---|---|---|---|---|---|---|---|---|---|
| | | Mesent Y105 | | Pedi PA-1 | | Quest | | Nisin | | Enterocin 900 | |
| Genus of Strains tested | | 1AU | 8AU | 1AU | 8AU | 1AU | 8AU | 1AU | 8AU | 1AU | 8AU |
| Bacillus | vegetative cells | 3/5 | 5/5 | 2/5 | 2/5 | 1/5 | 2/5 | 5/5 | 5/5 | 0/5 | 2/5 |
| | spores | 5/5 | 5/5 | 0/5 | 0/5 | 0/5 | 0/5 | 5/5 | 5/5 | 0/5 | 0/5 |
| Clostridia | vegetative cells | 0/8 | 1/8 | 0/8 | 0/8 | 0/8 | 0/8 | 7/8 | 8/8 | 2/8 | 3/8 |
| | spores | 0/7 | 0/7 | 0/7 | 0/7 | 0/7 | 0/7 | 5/7 | 7/7 | 0/7 | 0/7 |
| Staphylococcus | | 1/7 | 7/7 | 0/7 | 1/7 | 0/7 | 1/7 | 3/7 | 7/7 | 1/7 | 1/7 |
| Streptococcus | | 0/3 | 3/3 | 0/3 | 0/3 | 0/3 | 0/3 | 1/3 | 2/3 | 0/3 | 0/3 |
| Listeria | | 36/42 | 42/42 | 39/42 | 40/42 | 38/42 | 40/42 | 42/42 | 42/42 | 39/42 | 39/42 |
| G negative strains | | 0/29 | 0/29 | 0/29 | 0/29 | 0/29 | 0/29 | 0/29 | 0/29 | 0/29 | 0/29 |
| Brochothrix | | 0/14 | 0/14 | 0/14 | 0/14 | 0/14 | 0/14 | 14/14 | 14/14 | 0/14 | 0/14 |
| Carnobacteria | | 17/19 | 19/19 | 7/19 | 7/19 | 5/19 | 7/19 | 19/19 | 19/19 | 1/19 | 7/19 |
| Enterococcus | | 3/14 | 9/14 | 7/14 | 11/14 | 1/14 | 7/14 | 12/14 | 14/14 | 5/14 | 8/14 |
| Lactobacillus | | 1/17 | 2/17 | 1/17 | 2/17 | 1/17 | 2/17 | 16/17 | 17/17 | 2/17 | 5/17 |
| Lactococcus | | 0/8 | 1/8 | 0/8 | 0/8 | 0/8 | 0/8 | 4/8 | 6/8 | 4/8 | 4/8 |
| Leuconostoc | | 5/9 | 6/9 | 4/9 | 5/9 | 1/9 | 3/9 | 9/9 | 9/9 | 1/9 | 1/9 |
| Pediocuccus | | 0/3 | 0/3 | 0/3 | 2/3 | 0/3 | 0/3 | 3/3 | 3/3 | 0/3 | 0/3 |

TABLE 5

Bacteriocin production by Strains of Carnobacterium

| Producer strains | Indicator strains[a] | | | | | |
|---|---|---|---|---|---|---|
| | LV17C | | | LV13 | | |
| | MG36e | RW19e | JKM14 | MG36e | RW19e | JKM14 |
| *C. piscicola* | | | | | | |
| LV17C.MG36e | 0 | 0 | 0 | 0 | 0 | 0 |
| LV17C.RW19e | 30 | 0 | 30 | 0 | 0 | 0 |
| LV17C.JKM14 | 7 | 6 | 0 | 20 | 20 | 0 |
| *C. divergens* | | | | | | |
| LV13.MG36e | 23 | 0 | 23 | 0 | 0 | 0 |
| LV13.RW19e | 26 | 0 | 29 | 0 | 0 | 0 |
| LV13.JKM14 | 24 | 6 | 24 | 19 | 19 | 0 |

[a]zones of inhibition were determined by the deferred antagonism assay and measurements indicate the diameter of the zone of inhibition (cm).

---

What is claimed:

1. A method for inhibiting the growth of susceptible bacteria in an environment, comprising:
   providing a microorganism comprising a secretion vector that encodes a plurality of different bacteriocins heterologous to said microorganism, said secretion vector comprising:
   a first polynucleotide encoding a bacteriocin;
   a second polynucleotide encoding a bacteriocin processing peptide operable in said microorganism, operably linked to said polynucleotide encoding said bacteriocin;
   wherein at least one of said first polypeptide and said second polypeptide is heterologous to said microorganism; and
   a promoter operable in said host cell, operably linked to said polynucleotide encoding said bacteriocin; and
   applying said microorganism to said environment in an amount sufficient to inhibit the growth of susceptible bacteria.

2. A method for inhibiting the growth of susceptible bacteria comprising providing a microorganism that expresses heterologous DNA encoding a brochocin peptide, and applying said microorganism to susceptible bacteria in an amount sufficient to inhibit the growth of the susceptible bacteria, wherein said microorganism comprises a secretion vector that comprises a first polynucleotide that encodes brochocin-C and a second polypeptide encoding a brochocin-C processing peptide and at least one additional third polypeptide that encodes a bacteriocin other than brochocin-C, wherein at least one of the first polypeptide and the second polypeptide are heterologous to the microorganism.

3. A method for inhibiting the growth of susceptible bacteria comprising providing a microorganism that expresses heterologous DNA encoding a brochocin peptide, and applying said microorganism to susceptible bacteria in an amount sufficient to inhibit the growth of the susceptible bacteria, wherein said microorganism that expresses heterologous DNA encoding a brochocin peptide comprises a secretion vector comprising a structural gene for brochocin-C, the signal peptide of a gene sequence encoding divergicin A, and immunity gene of brochocin-C.

* * * * *